(12) United States Patent
Hodges et al.

(10) Patent No.: US 9,346,865 B2
(45) Date of Patent: *May 24, 2016

(54) ANTIMICROBIAL PEPTIDES AND METHODS OF USE

(75) Inventors: Robert S. Hodges, Denver, CO (US); Yuxin Chen, Changchun (CN)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/588,990

(22) Filed: Aug. 17, 2012

(65) Prior Publication Data

US 2013/0035469 A1    Feb. 7, 2013

Related U.S. Application Data

(63) Continuation of application No. 11/721,915, filed as application No. PCT/US2005/045393 on Dec. 15, 2005, now Pat. No. 8,252,737.

(60) Provisional application No. 60/636,220, filed on Dec. 15, 2004.

(51) Int. Cl.
*A61K 38/00* (2006.01)
*C07K 14/47* (2006.01)

(52) U.S. Cl.
CPC ............. *C07K 14/4723* (2013.01); *A61K 38/00* (2013.01)

(58) Field of Classification Search
None
See application file for complete search history.

(56) References Cited

U.S. PATENT DOCUMENTS

| | | |
|---|---|---|
| 5,593,866 A | 1/1997 | Hancock et al. |
| 5,688,767 A | 11/1997 | Hancock et al. |
| 5,707,855 A | 1/1998 | Hancock et al. |
| 5,789,377 A | 8/1998 | Hancock et al. |
| 5,798,336 A | 8/1998 | Travis et al. |
| 5,877,274 A | 3/1999 | Hancock et al. |
| 6,040,435 A | 3/2000 | Hancock et al. |
| 6,057,291 A | 5/2000 | Hancock et al. |
| 6,172,185 B1 | 1/2001 | Hancock et al. |
| 6,191,254 B1 | 2/2001 | Falla et al. |
| 6,288,212 B1 | 9/2001 | Hancock et al. |
| 6,297,215 B1 | 10/2001 | Hancock et al. |
| 6,337,317 B1 | 1/2002 | Hancock et al. |
| 6,358,921 B1 | 3/2002 | Kondejewski et al. |
| 6,465,429 B1 | 10/2002 | Hancock et al. |
| 6,566,334 B1 | 5/2003 | McLaughlin et al. |
| 6,696,559 B1 | 2/2004 | Selsted |
| 6,747,007 B2 | 6/2004 | Hancock et al. |
| 6,818,407 B2 | 11/2004 | Hancock et al. |
| 6,872,806 B1 | 3/2005 | Kondejewski et al. |
| 6,884,776 B1 | 4/2005 | Nibbering et al. |
| 6,906,035 B2 | 6/2005 | Hancock et al. |
| 8,252,737 B2 | 8/2012 | Hodges et al. |
| 2002/0035061 A1 | 3/2002 | Krieger et al. |
| 2003/0021795 A1 | 1/2003 | Houston et al. |
| 2003/0228324 A1 | 12/2003 | Malcolm et al. |
| 2005/0277589 A1 | 12/2005 | Arranz |
| 2007/0244044 A1 | 10/2007 | O'Neil |
| 2008/0027006 A1 | 1/2008 | Tripet et al. |
| 2009/0005300 A1 | 1/2009 | Hodges et al. |
| 2010/0099614 A1 | 4/2010 | Hodges et al. |
| 2011/0028386 A1 | 2/2011 | Hodges et al. |

FOREIGN PATENT DOCUMENTS

| | | |
|---|---|---|
| WO | 91/19512 | 12/1991 |
| WO | 00/12528 | 3/2000 |
| WO | 02/40536 | 5/2002 |
| WO | 03/004383 | 6/2003 |
| WO | 2005/025607 | 3/2005 |
| WO | 2005/077103 | 8/2005 |
| WO | 2006/065977 | 6/2006 |
| WO | 2010/141760 | 12/2010 |

OTHER PUBLICATIONS

Zhang et al., Biochemistry, 1999, vol. 38, pp. 8102-8111.*
Hancock, Antimicrobial Agents Chemotherapy, 1999, 43(6), 1317-1325.*
Zhang et al., Biochemistry, 1999, 38, 8102-11.*
Hancock, Antimicrobial Agents Chemotherapy, 1999, 43(6), 1317-25.*
Hong et al., Biochem. Pharm., 1999, 58, 1775-80.*
European Supplemental Search Report, dated Nov. 22, 2012, corresponding to European Application No. 05854163.2 (filed Dec. 15, 2005), parent of the present application, 12 pp.
Hancock, R.E.W. (2001) "Cationic Peptides: Effectors in Innate Immunity and Novel Antimicrobials," The Lancet 1:156-164.
Hartmann et al. (2003) "Comparison of Reversed-Phase Liquid Chromatography and Hydrophilic Interaction/Cation-Exchange Chromatography for the Separation of Amphipathic α-Helical Peptides with L- and D-Amino Acid Substitutions in the Hydrophilic Face," J Chromatography 1009:61-71.

(Continued)

*Primary Examiner* — Karlheinz R Skowronek
*Assistant Examiner* — Roy Teller
(74) *Attorney, Agent, or Firm* — Sheridan Ross P.C.

(57) ABSTRACT

Disclosed herein are novel antimicrobial peptides with useful, improved, or superior properties such as antimicrobial activity, specificity, resistance to degradation desirable levels of hemolytic activity, and therapeutic index against a broad range of microorganisms including gram-negative and gram-positive bacteria and other organisms having a cellular or structural component of a lipid bilayer membrane. Also provided are methods of making and using such peptides to control microbial growth and in pharmaceutical compositions for treatment or prevention of infections caused by such microorganisms. Certain peptides result from structure-based rational design relating to antimicrobial peptide V681, with single D-/L-amino acid substitutions or charged residue substitutions in or near the center of the peptide on the nonpolar or polar face. Some peptides contain one or more (or all) amino acids in the D configuration. Compositions disclosed herein have useful clinical potential as antibiotics including broad spectrum antibiotics.

10 Claims, 15 Drawing Sheets

(56) References Cited

OTHER PUBLICATIONS

Prosecution history for related U.S. Appl. No. 11/721,915, filed Jun. 6, 2008, (downloaded Nov. 13, 2012), last document dated Apr. 26, 2012, 58 pp.
Canadian Examination Report, dated Jul. 16, 2012, for Canadian patent application No. 2,633,435, filed Dec. 15, 2005, a corresponding application, 3 pp.
Examination Report, dated Dec. 9, 2011, for European patent application No. 05854163.2, filed Dec. 15, 2005, a corresponding application, 4 pp.
International Search Report and Written Opinion, mailed Dec. 18, 2006, for International Application No. PCT/US05/45393, filed Dec. 15, 2005, related subject matter, common inventor, 5 pp.
Prosecution history for related U.S. Appl. No. 12/574,545, filed Oct. 6, 2009, (downloaded Apr. 16, 2012), last document dated Mar. 5, 2012, 55 pp.
Prosecution history for related U.S. Appl. No. 12/793,666, filed Jun. 3, 2010, (downloaded Nov. 15, 2012), last document dated Oct. 31, 2012, 53 pp.
Supplemental EP Search Report, dated May 22, 2012, corresponding to EP patent application No. EP 09819768 (filed Oct. 6, 2009), related application, common inventor, 13 pp.
International Search Report and Written Opinion for PCT/US09/59717, a related application, mailed Mar. 16, 2010, 11 pp.
International Search Report and Written Opinion, mailed Dec. 9, 2010, for related International Application No. PCT/US10/37308, filed Jun. 3, 2010, related subject matter, common inventor, 16 pp.
Al-Bakri et al. (2005) "Influence of Gentamicin and Tobramycin on Binary Biofilm Formation by Co-Cultures of *Burkholderia cepacia* and *Pseudomonas aeruginosa*," J. Basic Microbiol. 45(5):392-396.
Andreu et al. (1992) "Shortened Cecropin A-Melittin Hybrids," FEBS Lett. 296(2):190-194.
Andreu et al. (1998) "Animal Antimicrobial Peptides: An Overview," Biopolymers 47:415-433.
Avrahami et al. (2002) "Conjugation of a Magainin Analogue with Lipophilic Acids Controls Hydrophobicity, Solution Assembly, and Cell Selectivity," Biochemistry 41:2254-2263.
Baumann et al. (1974) "A Molecular Model of Membrane Excitability," J. Supremol Struct 2:538-557.
Bland et al. (2001) "All-D-Cecropin B: Synthesis, Conformation, Lipopolysaccharide Binding, and Antibacterial Activity," Molecular and Cellular Biochemistry 218:105-111.
Blondelle et al. (1991) "Hemolytic and Antimicrobial Activities of the Twenty-Four Individual Omission Analogues of Melittin," Biochemistry 30:4671-4678.
Blondelle et al. (1992) "Design of Model Amphipathic Peptides Having Potent Antimicrobial Activities," Biochemistry 31(50):12688-12694.
Blondelle et al. (1995) "Induced Conformational States of Amphipathic Peptides in Aqueous/Lipid Environments," Biophys. J. 68:351-359.
Blondelle et al. (1999) "Lipid-Induced Conformation and Lipid-Binding Properties of Cytolytic and Antimicrobial Peptides: Determination and Biological Specificity," Biochim. Biophys. Acta 1462:89-108.
Bodmann, K.F. (2005) "Current Guidelines for the Treatment of Severe Pneumonia and Sepsis," Chemotherapy 51:227-233.
Boman, H.G. (2003) "Antibacterial Peptides: Basic Facts and Emerging Concepts," Journal of Internal Medicine 254:197-215.
Bowman et al. (2006) "The structure and synthesis of the fungal cell wall," Bioessays 28:799-808.
Brogden, K.A. (2005) "Antimicrobial Peptides: Pore Formers or Metabolic Inhibitors in Bacteria," www.nature.com/reviews/micro 3:238-250.
Brown, A.E. (1990) "Overview of Fungal Infections in Cancer Patients," Semin Oncol 17(3):2-5.
Carver et al. (2003) "The Design of Jemboss: A Graphical User Interface to Emboss," Bioinformatics 19(14):1837-1843.

Chen et al. (2002) "Determination of Stereochemistry Stability Coefficients of Amino Acid Side-Chains in an Amphipathic $\alpha$-Helix," J. Peptide Res. 59:18-33.
Chen et al. (2003) "Temperature selectivity effects in reversed-phase liquid chromatography due to conformation differences between helical and non-helical peptides," Journal of Chromatography A 1010:45-61.
Chen et al. (2004) "Optimum Concentration of Trifluoroacetic Acid for Reversed-Phase Liquid Chromatography of Peptides Revisited," J. Chromatogr. A 1043:9-18.
Chen et al. (2005) "Rational Design of $\alpha$-Helical Antimicrobial Peptides with Enhanced Activities and Specificity/Therapeutic Index," The Journal of Biological Chemistry, 280(13):12316-12329.
Chen et al. (2006) "Comparison of Biophysical and Biologic Properties of $\alpha$-Helical Enantiomeric Antimicrobial Peptides," Chem Biol Drug Des 67:162-173.
Chen et al. (Apr. 2007) "Role of Peptide Hydrophobicity in the Mechanism of Action of $\alpha$-Helical Antimicrobial Peptides," Antimicrobial Agents and Chemotherapy, 51(4):1398-1406, American Society for Microbiology.
Chen et al. (2007) "Preparative reversed-phase high-performance liquid chromatography collection efficiency for an antimicrobial peptide on columns of varying diameters (1 mm to 9.4 mm I.D.)," J. Chromatogr A 1140:112-120.
Christensen et al. (1988) "Channel-Forming Properties of Cecropine and Related Model Compounds Incorporated into Planar Lipid Membranes," Proc. Nat. Acad. Sci. USA 85:5072-5076.
Chu-Kung et al. (cover date Dec. 2004) "Effect of Fatty Acid Conjugation on Antimicrobial Peptide Activity," University of California, 6 pp., Santa Barbara, CA.
Cribbs et al. (1997) "All-D-Enantiomers of Beta-Amyloid Exhibit Similar Biological Properties to All-L-Beta-Amyloids," J. Biol. Chem. 272:7431-7436.
Dathe et al. (1997) "Hydrophobicity, Hydrophobic Moment and Angle Subtended by Charged Residues Modulate Antibacterial and Hemolytic Activity of Amphipathic Helical Peptides," FEBS Lett. 403:208-212.
Dathe et al. (1996) "Peptide Helicity and Membrane Surface Charge Modulate the Balance of Electrostatic and Hydrophobic Interactions with Lipid Bilayers and Biological Membranes," Biochemistry 35:12612-12622.
Daum, G. (1985) "Lipids of mitochondria," Biochim. Biophys. Acta 822:1-42.
De Lucca et al. (2000) "D-Cecropin B: Proteolytic Resistance, Lethality for Pathogenic Fungi and Binding Properties," Medical Mycology 38:301-308.
Dennison et al. (2003) "Factors Determining the Efficacy of Alpha-Helical Antimicrobial Peptides," Protein Pept Lett 10(5):497-502.
Dennison et al. (2005) "Amphiphilic $\alpha$-Helical Antimicrobial Peptides and Their Structure/Function Relationships," Protein Pept Lett 12:31-39.
DeVaux et al. (1985) "Specificity of lipid-protein interactions as determined by spectroscopic techniques," Biochim. Biophys. Acta. 822:63-125.
Devine et al. (2002) "Cationic Peptides: Distribution and Mechanisms of Resistance," Curr. Pharm. Des. 8:703-714.
Dolan, J.W. (2002) "Temperature Selectivity in Reversed-Phase High Performance Liquid Chromatography," J. Chromatogr. A 965:195-205.
Duclohier et al. (1989) "Antimicrobial Peptide Magainin I from Xenopus Skin Forms Anion-Permeable Channels in Planar Lipid Bilayers," Biophys. J. 56:1017-1021.
Durden et al. (Sep. 1997) "Fungal Infections in HIV-Infected Patients,"Seminars Cutan Med Surg 16(3):200-212.
Ehrenstein et al. (1977) "Electrically Gated Ionic Channels in Lipid Bilayers," Q. Rev. Biophys. 10:1-34.
Eisenberg et al. (1982) "The Helical Hydrophobic Moment: A Measure of the Amphiphilicity of a Helix," Nature 299:371-374.
Elkin et al. (2003) "Pseudomonal Infection in Cystic Fibrosis: The Battle Continues," Exp. Rev. Anti. Infect. Ther. 1(4):609-618.
Elmquist et al. (2003) "In Vitro Uptake and Stability Study of *p*VEC and its All-D Analog," Biol. Chem. 384:387-393.

(56) References Cited

OTHER PUBLICATIONS

Gabriel et al. (Jun. 2007) "Infectious disease: Connecting innate immunity to biocidal polymers," Mater Sci Eng R Rep 57:28-64.

Ganz et al. (1994) "Defensins," Curr. Opin Immunol. 6:584-589.

Georgopapadakou et al. (Apr. 1994) "Human Mycoses: Drugs and Targets for Emerging Pathogens," Science 264:371-373.

Guo et al. (1986) "Prediction of Peptide Retention Times in Reversed-Phase High-Performance Liquid Chromatography. I. Determination of Retention Coefficients of Amino Acid Residues Using Model Synthetic Peptides," J. Chromatogr. 359:499-518.

Guo et al. (1986) "Prediction of Peptide Retention Times in Reversed-Phase High-Performance Liquid Chromatography. II. Correlation of Observed and Predicted Peptide Retention Times and Factors Influencing the Retention Times of Peptides," J. Chromatogr. 359:519-532.

Hamamoto et al. (2002) "Antimicrobial Activity and Stability to Proteolysis of Small Linear Cationic Peptides with D-Amino Acid Substitutions," Microbiol. Immunol. 46(11):741-749.

Hancock, R.E.W. (1997) "Peptide Antibiotics," Lancet 349:418-422.

Hancock et al. (1998) "Cationic Peptides: A New Source of Antibiotics," Trends Biotechnol. 16:82-88.

Hancock et al. (2002) "Role of Membranes in the Activities of Antimicrobial Cationic Peptides," FEMS Microbiol. Lett. 206:143-149.

Hodges et al. (Oct. 2004) "Monitoring the hydrophilicity/hydrophobocity of amino acid side-chains in the non-polar and polar faces of amphipathic α-helices by reversed-phase and hydrophilic interaction/cation-exchange chromatography," J Chromatography 1053:161-172.

Hoiby et al. (1990) "Cystic Fibrosis. 1. *Pseudomonas aeruginosa* Infection in Cycstic Fibrosis and its Management," Thorax 45:881-884.

Hong et al. (1999) "Effect of $_D$-Amino Acid Substitution on the Stability, the Secondary Structure, and the Activity of Membrane-Active Peptide," Biochem. Pharmacol. 58:1775-1780.

Jenssen et al. (Jul. 2006) "Peptide Antimicrobial Agents," Clin Microbial Rev 19(3):491-511.

Jiang et al. (published online Dec. 20, 2007) "Effects of Net Charge and the No. Of Positively Charged Residues on the Biological Activity of Amphipathic α-Helical Cationic Antimicrobial Peptides," Biopolymers 90(3):369-383.

Jiang et al. (2008) "Effects of Hydrophobicity on the Antifungal Activity of α-Helical Antimicrobial Peptides," Chem Biol Drug Des 72:483-495.

Jiang et al. (2009) "Effects of Net Charge and the Number of Positively Charged Residues on the Biological Activity of Amphipathic α-helical Cationic Antimicrobial Peptides," Peptides for Youth: The Proceedings of the 20$^{th}$ American Peptide Symposium, S. Del Valle et al. (eds.) pp. 561-562.

Jiang et al. (conference Jun. 7-12, 2009) "Effect of Net Positive Charge and Charge Distribution on the Polar Face of Amphipathic α-Helical Antimicrobial Peptides on their Biological and Biophysical Properties," in Peptides: Breaking Away, Proceedings of the Twenty-First American Peptide Symposium, edited by Michel Lebl, pp. 266-267, Bloomington, IN.

Jiang et al. (2011) "Rational Design of α-Helical Antimicrobial Peptides to Target Gram-negative Pathogens, *Acinetobacter baumannii* and *Pseudomonas aeruginosa*: Utilization of Charge, 'Specificity Determinants,' Total Hydrophobicity, Hydrophobe Type and Location as Design Parameters to Improve the Therapeutic Ratio," Chem Biol Drug Des 77:225-240.

Khaled et al. (1978) "Hydrogen-Deuterium Substitution and Solvent Effects on the Nitrogen-15 Nuclear Magnetic Resonance of Gramicidin S: Evaluation of Secondary Structure," Biochemistry 17(13):2490-2494.

Kiyota et al. (1996) "Design and Synthesis of Amphiphilic α-Helical Model Peptides with Systematically Varied Hydrophobic-Hydrophilic Balance and Their Interaction with Lipid- and Bio-Membranes," Biochemistry 35:13196-13204.

Kondejewski et al. (2002) "Optimization of Microbial Specificity in Cyclic Peptides by Modulation of Hydrophobicity within a defined Structural Framework," J. Biol. Chem. 277(1):67-74.

Kondejewski et al. (1999) "Dissociation of Antimicrobial and Hemolytic Activities in Cyclic Peptide Diastereomers by Systematic Alterations in Amphipathicity," J. Biol. Chem. 274(19):13181-13192.

Kontoyiannis et al. (2002) "Antifungal drug resistance of pathogenic fungi," Lancet 359:1135-1144.

Kovacs et al. (2006) "Determination of Intrinsic Hydrophilicity/Hydrophobicity of Amino Acid Side-Chains in Peptides in the Absence of Nearest-Neighbor or Conformational Effects," Biopolymers (Peptide Science) 84:283-297.

Kustanovich et al. (2002) "Structural Requirements for Potent Versus Selective Cytotoxicity for Antimicrobial Dermaseptin s4 Derivatives," J. Biol. Chem. 277:16941-16951.

Lee et al. (2003) "Structure-Activity Relationships of de novo Designed Cyclic Antimicrobial Peptides Based on Gramicidin S," Biopolymers (Peptide Science) 71:28-48.

Lee et al. (2004) "Effects of Single D-Amino Acid Substitutions on Disruption of β-Sheet Structure and Hydrophobicity in Cyclic 14-Residue Antimicrobial Peptide Analogs Related to Gramicidin S," J. Peptide Res. 63(2):69-84.

Lee et al. (2003) "A Novel Method to Measure Self-Association of Small Amphipathic Molecules: Temperature Profiling in Reversed-Phase Chromatography," J. Biol. Chem. 278:22918-22927.

Liu et al. (2002) "Effect of Variations in the Structure of a Polyleucine-Based α-Helical Transmembrane Peptide on Its Interaction with Phosphatidylcholine Bilayers," Biochemistry 41(29):9197-9207.

Liu et al. (2004) "Effect of Variations in the Structure of a Polyleucine-Based α-Helical Transmembrane Peptide on its Interaction with Phosphatidylethanolamine Bilayers," Biophys. J. 87:2470-2482.

Liu et al. (2004) "Effect of Variations in the Structure of a Polyleucine-Based α-Helical Transmembrane Peptide on Its Interaction with Phosphatidylglycerol Bilayers," Biochemistry 43(12):3679-3687.

Liu et al. (Mar. 24, 2006) "Toll-Like Receptor Triggering of a Vitamin D-Mediated Human Antimicrobial Response," Science, 311:1770-1773.

Lugtenberg et al. (1983) "Molecular Architecture and Functioning of the Outer Membrane of *Escherichia coli* and Other Gram-Negative Bacteria," Biochim. Biophys. Acta 737:51-115.

Lustig et al. (1996) "Alternative Splicing Determines the Binding of Platelet-Derived Growth Factor (PDGF-AA) to Glycosaminoglycans," Biochemistry 35:12077-12085.

Mant et al. (1993) "The Role of Amphipathic Helices in Stabilizing Peptide and Protein Structure," The Amphipathic Helix, Epand, R.M. ed., CTC Press, Boca Raton, FL, Chapter 3, pp. 39-64.

Mant et al. (2002) "Reversed-Phase Liquid Chromatography as a Tool in the Determination of the Hydrophilicity/Hydrophobicity of Amino Acid Side-Chains at a Ligand-Receptor Interface in the Presence of Different Aqueous Environments: II. Effect of Varying Peptide Ligand Hydrophobicity," J. Chromatogr. A 972(1):61-75.

Mant et al. (2002) "Reversed-Phase Liquid Chromatography as a Tool in the Determination of the Hydrophilicity/Hydrophobicity of Amino Acid Side-Chains at a Ligand-Receptor Interface in the Presence of Different Aqueous Environments: I. Effect of Varying Receptor Hydrophobicity," J. Chromatogr. A 972(1):45-60.

Mant et al. (2003) "Temperature Profiling of Polypeptides in Reversed-Phase Liquid Chromatography. I. Monitoring of Dimerization and Unfolding of Amphipathic α-Helical Peptides," J. Chromatogr. A 1009:29-43.

Mant et al. (2003) "Temperature Profiling of Polypeptides in Reversed-Phase Liquid Chromatography. II. Monitoring of Folding and Stability of Two-Stranded α-Helical Coiled Coils," J. Chromatogr. A 1009:45-59.

Mant et al. (Dec. 2009) "Intrinsic Amino Acid Side-Chain Hydrophilicity/ Hydrophobicity Coefficients Determined by Reversed-Phase High-Performance Liquid Chromato-graphy of Model Peptides: Comparison with Other Hydrophilicity/Hydrophobicity Scales," Biopolymers, 92(6):573-595.

(56) References Cited

OTHER PUBLICATIONS

Martineau et al. (Jul. 2007) "Neutrophil-mediated innate immune resistance to mycobacteria," The Journal of Clinical Investigation, 117(7):1988-1994.
Matsuzaki, K. (1999) "Why and How are Peptide-Lipid Interactions Utilized for Self Defense? Magainins and Tachyplesins as Archetypes," Biochim. Biophys. Acta 1462:1-10.
McInnes et al. (2000) "Development of the Structural Basis for Antimicrobial and Hemolytic Activities of Peptides Based on Gramicidin S and Design of Novel Analogs Using NMR Spectroscopy," J. Biol. Chem. 275(19):14287-14294.
McPhillips et al. (1986) *Modern Pharmacol*, $2^{nd}$ ed., Little, Brown and Co., Boston, Chapter 9, pp. 127-133.
Monera et al. (1995) "Relationship of SideChain Hydrophobicity and α-Helical Propensity on the Stability of the Single-Stranded Amphipathic α-Helix," J. Peptide Sci. 1:319-329.
Mootz et al. (1997) "The Tyrocidine Biosynthesis Operon of *Bacillus brevis*: Complete Nucleotide Sequence and Biochemical Characterization of Functional Internal Adenylation Domains," J. Bacteriol. 179(21):6843-6850.
Neu, H.C. (Aug. 21, 1992) "The Crisis in Antibiotic Resistance," Science 257.5073:1064-1073.
Obritsch et al. (2005) "Nosocomial Infections Due to Multidrug-Resistant *Pseudomonas aeruginosa*: Epidemiology and Treatment Options," Pharmacotherapy 25(10):1353-1364.
Oren et al. (1997) "A Repertoire of Novel Antibacterial Diastereomeric Peptides with Selective Cytolytic Activity," J. Biol. Chem. 272(23):14643-14649.
Oren et al. (1997) "Selective Lysis of Bacteria but Not Mammalian Cells by Diasteromers of Melittin: Structure-Function Study," Biochemistry 36(7):1826-1835.
Pierce, G.E. (2005) *Pseudomonas aeruginosa, Candida albicans*, and Device-Related Nosocomial Infections: Implications, Trends, and Potential Approaches for Control, J. Ind. Microbiol. Biotechnol. 32:309-318.
Pouny et al. (1992) "Interaction of Antimicrobial Dermaseptin and its Fluorescently Labeled Analogues with Phospholipid Membranes," Biochemistry 31:12416-12423.
Powers et al. (2004) "Structure-Activity Relationships for the β-Hairpin Cationic Antimicrobial Peptide Polyphemusin I," Biochim. Biophys. Acta. 1698:239-250.
Purcell et al. (1995) "Induction of amphipathic helical peptide structures in RP-HPLC,"Pept. Res. 8(3):160-170. (Abstract only).
Reddy et al. (2004) "Antimicrobial Peptides: Premises and Promises," Int. J. Antimicrob. Agents 24:536-547.
Salgado et al. (2001) "Membrane-Bound Structure and Alignment of the Antimicrobial β-Sheet Peptide Gramicidin S Derived from Angular and Distance Constraints by Solid-State $^{19}$F-NMR," J. Biomol. NMR 21:191-208.
Shai et al. (1996) "Diastereomers of Cytolysins, a Novel Class of Potent Antibacterial Peptides," J. Biol. Chem. 271(13):7305-7308.
Shai, Y. (1999) "Mechanism of the Binding, Insertion and Destabilization of Phospholipid Bilayer Membranes by α-Helical Antimicrobial and Cell Non-Selective Membrane-Lytic Peptides," Biochim. Biophys. Acta. 1462:55-70.
Sitaram et al. (1999) "Interaction of Antimicrobial Peptides with Biological and Model Membranes: Structural and Charge Requirements for Activity," Biochim. Biophys. Acta 1462:29-54.
Sitaram et al. (2002) "Host-Defense Antimicrobial Peptides: Importance of Structure for Activity," Curr. Pharm. Des. 8:727-742.
Speight, T. (1987) "Fundamentals of Clinical Pharmacology," Avery's Drug Treatment: Principles and Practice of Clinical Pharmacology and Therapeutics, $3^{rd}$ ed., Williams and Wilkins, Baltimore, Chapter I, p. 50-56.
Spilker, B. (1984) "Preliminary Considerations Relating to Study Design," Guide to Clinical Studies and Developing Protocols, Raven Press, Ltd., New York, Chapter 2, pp. 7-13.
Spilker, B. (1991) "Dosing Schedule," Guide to Clinical Trials, Raven Press, Ltd., New York, Chapter 14, pp. 93-101.
Steinberg et al. (1997) "Protegrin-1: A Broad-Spectrum, Rapidly Microbicidal Peptide with In Vivo Activity," Antimicrob. Agents Chemother. 41(8):1738-1742.
Tachi et al. (2002) "Positron-Dependent Hydrophobicity of the Antimicrobial Magainin Peptide Affects the Mode of Peptide-Lipid Interactions and Selective Toxicity," Biochemistry 41:10723-10731.
Tallarida et al. (1988) "Dose-Effect Graphs: Potency and Efficacy," Principles in General Pharmacology, Springer-Verlag, New York, Chapter 2, pp. 18-20.
Tossi et al. (2000) "Amphipathic, α-Helical Antimicrobial Peptides," Biopolymers 55:4-30.
Travis, J. (1994) "Reviving the Antibiotic Miracle," Science 264:360-362.
Van 'T Hof et al. (Apr. 2001) "Antimicrobial Peptides: Properties and Applicability,"Biol. Chem. 382:597-619.
Wade et al. (1990) "All-D Amino Acid-Containing Channel-Forming Antibiotic Peptides," Proc. Nat. Acad. Sci. USA 87:4761-4765.
Wakabayashi et al. (1999) "N-Acylated and D Enantiomer Derivatives of a Nonamer Core Peptide of Lactoferricin B Showing Improved Antimicribial Activity," Antimicrob. Agents Chemother. 43:1267-1269.
Wieprecht et al. (1997) "Peptide Hydrophobicity Controls the Activity and Selectivity of Magainin 2 Amide in Interaction with Membranes," Biochemistry 36:6124-6132.
Wieprecht et al. (1997) "Modulation of Membrane Activity of Amphipathic, Antibacterial Peptides by Slight Modifications of the Hydrophobic Moment," FEBS Lett. 417:135-140.
Zasloff, M. (1987) "Magainins, A Class of Antimicrobial Peptides from *Xenopus* Skin: Isolation, Characterization of Two Active Forms, and Partial cDNA Sequence of a Precursor," Proc. Nat. Acad. Sci. USA 84:5449-5453.
Zhang et al. (1999) "Influence of Proline Residues on the Antibacterial and Synergistic Activities of Alpha-Helical Antimicrobial Peptides with Enhanced Activities and Specificity/Therapeutic Index," Biochemistry 38:8102-8111.
Zhang et al. (1998) "Determinants of Recombinant Production of Antimicrobial Cationic Peptides and Creation of Peptide Variants in Bacteria," Biochem. Biophys. Res. Commun. 247:674-680.
Zhang et al. (2001) "Interaction of Cationic Antimicrobial Peptides with Model Membranes," J. Biol. Chem. 276(38):35714-35722.
Zhou et al. (1990) "Effect of Preferred Binding Domains on Peptide Retention Behavior in Reversed-Phase Chromatography: Amphipathic α-Helices," Pept. Res. 3(1):8-20.
Zhou et al. (1994) "α-Helical Propensities of Amino Acids in the Hydrophobic Face of an Amphipathic α-Helix," Protein Pept. Lett. 1(2):114-119.
Zilberstein et al. (1979) "Proton Electrochemical Gradient in *Escherichia coli* Cells and Its Relation to Active Transport of Lactose," Biochemistry 18(4):669-673.

* cited by examiner

ANTIMICROBIAL PEPTIDES AND METHODS OF USE

CROSS-REFERENCE TO RELATED APPLICATIONS

This application is a Continuation of U.S. application Ser. No. 11/721,915, filed Jun. 6, 2008, now U.S. Pat. No. 8,252,737, which is the U.S. National Stage of International Application No. PCT/US2005/045393, filed Dec. 15, 2005, which claims benefit of U.S. Provisional Application No. 60/636,220, filed Dec. 15, 2004, all of which are hereby incorporated by reference to the extent not inconsistent with the present disclosure.

STATEMENT ON FEDERALLY SPONSORED RESEARCH OR DEVELOPMENT

This invention was made with government support under contract number AI048717 awarded by the National Institutes of Health. The government has certain rights in the invention.

BACKGROUND OF THE INVENTION

The present invention broadly relates to novel antimicrobial peptides and methods of making and using such peptides to inhibit microbial growth and in pharmaceutical compositions for treatment or prevention of infections caused by a broad range of microorganisms including gram-positive and gram-negative bacteria.

The extensive clinical use of classical antibiotics has led to the growing emergence of many medically relevant resistant strains of bacteria (1,2). Moreover, only three new structural classes of antibiotics (the oxazolidinone, linezolid, the streptogramins and the lipopeptide-daptomycin) have been introduced into medical practice in the past 40 years. Therefore, the development of a new class of antibiotics has great significance. The cationic antimicrobial peptides could represent such a new class of antibiotics (3-5). Although the exact mode of action of the cationic antimicrobial peptides has not been established, all cationic amphipathic peptides interact with membranes and it has been proposed that the cytoplasmic membrane is the main target of some peptides, where peptide accumulation in the membrane may cause increased permeability and loss of barrier function (6,7). Therefore, the development of resistance to these membrane active peptides is less likely because this would require substantial changes in the lipid composition of cell membranes of microorganisms.

Two major classes of the cationic antimicrobial peptides are the α-helical and the β-sheet peptides (3,4,8,9). The β-sheet class includes cyclic peptides constrained in this conformation either by intramolecular disulfide bonds, e.g., defensins (10) and protegrins (11), or by an N-terminal to C-terminal covalent bond, e.g., gramicidin S (12) and tyrocidines (13). Unlike the β-sheet peptides, α-helical peptides are more linear molecules that mainly exist as disordered structures in aqueous media and become amphipathic helices upon interaction with the hydrophobic membranes, e.g., cecropins (14), magainins (15) and melittins (16). Concerning such peptides, we have explored certain factors that may be important in relation to antimicrobial activity.

The major barrier to the use of antimicrobial peptides as antibiotics is their toxicity or ability to lyse eukaryotic cells. This is perhaps not a surprising result if the target is indeed the cell membrane (3-6). To be useful as a broad-spectrum antibiotic, it is necessary to dissociate anti-eukaryotic activity from antimicrobial activity, i.e., increasing the antimicrobial activity and reducing toxicity to normal cells.

A synthetic peptide approach to examining the effect of changes, including small or incremental changes, in hydrophobicity/hydrophilicity, amphipathicity and helicity of cationic antimicrobial peptides can facilitate rapid progress in rational design of peptide antibiotics. Generally, only L-amino acids are the isomers found throughout natural peptides and proteins; D-amino acids are the isomeric forms rarely seen in natural peptides/proteins except in some bacterial cell walls. In certain circumstances, the helix-destabilizing properties of D-amino acids offer a potential systematic approach to the controlled alteration of the hydrophobicity, amphipathicity, and helicity of amphipathic α-helical model peptides (26).

Herein, we disclose the utilization of the structural framework of an amphipathic α-helical antimicrobial peptide, $V_{681}$ (28), to systematically change peptide amphipathicity, hydrophobicity and helicity by single D- or L-amino acid substitutions in the center of either the polar or nonpolar faces of the amphipathic helix. Peptide $V_{681}$ has been shown to have excellent antimicrobial activity and strong hemolytic activity (27,28) and thus served as a potentially useful candidate for our study. By introducing different D- or L-amino acid substitutions, we report here that hydrophobicity/amphipathicity and helicity have dramatic effects on the biophysical and biological activities and, utilizing this method, a significant improvement in antimicrobial activity and specificity can be achieved. In addition, high peptide hydrophobicity and amphipathicity can also result in greater peptide self-association in solution. Since we have developed a useful method to measure self-association of small amphipathic molecules, namely temperature profiling in reversed-phase chromatography (29,30), this technique was applied for the first time to investigate the influence of peptide dimerization ability on biological activities of α-helical antimicrobial peptides. The advantage of the invention will become apparent in the following description.

SUMMARY OF THE INVENTION

The present invention provides peptide compounds useful as antimicrobial agents and related methods. In embodiments of the invention, the antimicrobial peptides range in size from about 23 to about 26 amino acids in length joined by peptide bonds and have a core amino acid sequence of about 21 amino acids. The amino acids in the peptide compounds can be all in the L configuration, all in the D configuration or in a combination of D or L configurations. The peptides have potent antimicrobial activities and are useful against bacteria, fungi, viruses, and protozoa. The peptides are generally effective in the context of any organism having a cellular or structural component of a lipid bilayer membrane. These peptides are effective compounds for use in human and/or veterinary medicine, or as agents in agricultural, food science, or industrial applications.

Without wishing to be bound by a particular theory, from numerous structure/activity studies on both natural and synthetic antimicrobial peptides it is believed that a number of factors are important for antimicrobial activity. These are identified as including the presence of both hydrophobic and basic residues, an amphipathic nature that segregates basic and hydrophobic residues, and an inducible or preformed secondary structure (α-helical or β-sheet). Also without wishing to be bound by a particular theory, it is believed that by substituting different D-amino acids into the center of the hydrophobic face of an amphipathic α-helical model peptide, disruption of alpha-helical structure can occur. Different D-amino acids can disrupt α-helical structure to different degrees, whilst the destabilized structure can still be induced to fold into an α-helix in hydrophobic medium. An advantage of this method of single D- or L-amino acid substitutions at a specific site is that it provides an opportunity for greater understanding of the mechanism of action of these peptides.

It is recognized that regardless of the ultimate correctness of any mechanistic explanation or hypothesis, the compositions and methods of the invention can nonetheless be operative and useful.

For certain α-helical and β-sheet peptides, there have been attempts to delineate features responsible for anti-eukaryotic or toxic activities and for antimicrobial activities. High amphipathicity (17-20), high hydrophobicity (17, 20-22), as well as high helicity or β-sheet structure (20,23,24) may correlate with increased toxicity as measured by hemolytic activity. In contrast, antimicrobial activity may be less dependent on these factors, compared with hemolytic activity (17-21, 23-25). Here, specificity (or therapeutic index (TI) which is defined as the ratio of hemolytic activity and antimicrobial activity) for bacteria over erythrocytes could be increased in one of three ways: increasing antimicrobial activity, decreasing hemolytic activity while maintaining antimicrobial activity, or a combination of both, increasing antimicrobial activity and decreasing hemolytic activity.

The invention provides a method of treating a patient in need of therapy comprising administering to the patient a peptide compound of the invention. The invention provides a method of treating a microbial infection. In a particular embodiment, the microbial infection involves one or more of a bacterium, a virus, a fungus, or a protozoan. In a particular embodiment, the microbial infection involves one or more of each of those kinds of organisms, e.g. two different kinds of bacteria, and so forth.

In an embodiment, the invention provides a method for increasing antimicrobial activity of a peptide compound. In an embodiment, the invention provides a method for decreasing hemolytic activity of a peptide compound while maintaining antimicrobial activity or minimizing a reduction of antimicrobial activity. In an embodiment, the invention provides a method of increasing antimicrobial activity and decreasing hemolytic activity of a peptide compound while maintaining antimicrobial activity or minimizing a reduction of antimicrobial activity.

The inventors discovered the antimicrobial peptides disclosed herein based on the premise that controlled alteration of the hydrophobicity/hydrophilicity, amphipathicity and helicity of an alpha helical peptide would yield a peptide with useful or improved biological activity and specificity (e.g. improved therapeutic index). Exemplified herein are peptides derived from the 26-residue peptide sequence, Ac-KWKS-FLKTFKS-AVKTVLHTALKAISS-amide ($V_{681}$, SEQ ID NO: 1). The terms "derived from" or "derivative" are meant to indicate that the inventive peptides are the same or shorter than the $V_{681}$ peptide in size and have one or more amino acid residues substituted, or a combination of both; further variations are also described herein. The peptide compound $V_{681}$ was used as the framework to study the effects of peptide hydrophobicity/hydrophilicity, amphipathicity and helicity on biological activities, for example antimicrobial and hemolytic activities, by substituting one or more amino acid residues at certain locations. These locations can include points at or near the center of the polar and nonpolar faces of the amphipathic helix in addition to other locations. The peptide $V_{681}$ is disclosed in Zhang et al., 1999 and Zhang et al., 2001.

In an embodiment, the invention provides compositions and methods relating to a peptide selected from the group consisting of SEQ ID NOS:2, 4-14, and 16-25 and other peptides as disclosed herein, e.g. in the Examples. It is noted that SEQ ID NO:1, peptide V681, is exactly equivalent to SEQ ID NOS:3 and 15. See Table 1 which includes peptides with substitutions on the nonpolar face at position X=13 and on the polar face at position X=11. See also Table 2 which includes other peptide analogs.

TABLE 1

Summary of partial sequence listing information.

| SEQ ID NO: | Peptide Name | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|---|
| | Enantiomer* | L | L | L | L | L | L | L | L | L | L | L | L | L | L | L | L | L | L | L | L | L | L | L | L | L | L |
| 1 | V681 | K | W | K | S | F | L | K | T | F | K | S | A | V | K | T | V | L | H | T | A | L | K | A | I | S | S |
| 2 | $NL_L$ | K | W | K | S | F | L | K | T | F | K | S | A | $L_L$ | K | T | V | L | H | T | A | L | K | A | I | S | S |
| 3 | $NV_L$ | K | W | K | S | F | L | K | T | F | K | S | A | $V_L$ | K | T | V | L | H | T | A | L | K | A | I | S | S |
| 4 | $NA_L$ | K | W | K | S | F | L | K | T | F | K | S | A | $A_L$ | K | T | V | L | H | T | A | L | K | A | I | S | S |
| 5 | $NS_L$ | K | W | K | S | F | L | K | T | F | K | S | A | $S_L$ | K | T | V | L | H | T | A | L | K | A | I | S | S |
| 6 | $NK_L$ | K | W | K | S | F | L | K | T | F | K | S | A | $K_L$ | K | T | V | L | H | T | A | L | K | A | I | S | S |
| 7 | $NL_D$ | K | W | K | S | F | L | K | T | F | K | S | A | $L_D$ | K | T | V | L | H | T | A | L | K | A | I | S | S |
| 8 | $NV_D$ | K | W | K | S | F | L | K | T | F | K | S | A | $V_D$ | K | T | V | L | H | T | A | L | K | A | I | S | S |
| 9 | $NA_D$ | K | W | K | S | F | L | K | T | F | K | S | A | $A_D$ | K | T | V | L | H | T | A | L | K | A | I | S | S |
| 10 | $NS_D$ | K | W | K | S | F | L | K | T | F | K | S | A | $S_D$ | K | T | V | L | H | T | A | L | K | A | I | S | S |
| 11 | $NK_D$ | K | W | K | S | F | L | K | T | F | K | S | A | $K_D$ | K | T | V | L | H | T | A | L | K | A | I | S | S |
| 12 | NG | K | W | K | S | F | L | K | T | F | K | S | A | G | K | T | V | L | H | T | A | L | K | A | I | S | S |
| 13 | $PL_L$ | K | W | K | S | F | L | K | T | F | K | $L_L$ | A | V | K | T | V | L | H | T | A | L | K | A | I | S | S |
| 14 | $PA_L$ | K | W | K | S | F | L | K | T | F | K | $A_L$ | A | V | K | T | V | L | H | T | A | L | K | A | I | S | S |
| 15 | $PS_L$ | K | W | K | S | F | L | K | T | F | K | $S_L$ | A | V | K | T | V | L | H | T | A | L | K | A | I | S | S |
| 16 | $PV_L$ | K | W | K | S | F | L | K | T | F | K | $V_L$ | A | V | K | T | V | L | H | T | A | L | K | A | I | S | S |
| 17 | $PK_L$ | K | W | K | S | F | L | K | T | F | K | $K_L$ | A | V | K | T | V | L | H | T | A | L | K | A | I | S | S |
| 18 | $PL_D$ | K | W | K | S | F | L | K | T | F | K | $L_D$ | A | V | K | T | V | L | H | T | A | L | K | A | I | S | S |
| 19 | $PA_D$ | K | W | K | S | F | L | K | T | F | K | $A_D$ | A | V | K | T | V | L | H | T | A | L | K | A | I | S | S |
| 20 | $PS_D$ | K | W | K | S | F | L | K | T | F | K | $S_D$ | A | V | K | T | V | L | H | T | A | L | K | A | I | S | S |
| 21 | $PV_D$ | K | W | K | S | F | L | K | T | F | K | $V_D$ | A | V | K | T | V | L | H | T | A | L | K | A | I | S | S |
| 22 | $PK_D$ | K | W | K | S | F | L | K | T | F | K | $K_D$ | A | V | K | T | V | L | H | T | A | L | K | A | I | S | S |
| 23 | PG | K | W | K | S | F | L | K | T | F | K | G | A | V | K | T | V | L | H | T | A | L | K | A | I | S | S |

TABLE 1-continued

Summary of partial sequence listing information.

| SEQ ID NO: | Peptide Name | Amino Acid Position |  |  |  |  |  |  |  |  |  |  |  |  |  |  |  |  |  |  |  |  |  |  |  |  |
|---|---|---|---|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
| | Enantiomer | D | D | D | D | D | D | D | D | D | D | D | D | D | D | D | D | D | D | D | D | D | D | D | D | D | D |
| 24 | D-NK$_D$ | K | W | K | S | F | L | K | T | F | K | S | A | K | K | T | V | L | H | T | A | L | K | A | I | S | S |
| 25 | D-NA$_L$ | K | W | K | S | F | L | K | T | F | K | S | A | A$_L$ | K | T | V | L | H | T | A | L | K | A | I | S | S |
| 1 | D-V681 | K | W | K | S | F | L | K | T | F | K | S | A | V | K | T | V | L | H | T | A | L | K | A | I | S | S |

*L-enantiomer unless otherwise indicated in the Enantiomer column or subscript.

TABLE 2

Summary of partial sequence listing information.

| SEQ ID NO: | Peptide Name | Amino Acid Position |  |  |  |  |  |  |  |  |  |  |  |  |  |  |  |  |  |  |  |  |  |  |  |  |
|---|---|---|---|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
| | Enantiomer* | L | L | L | L | L | L | L | L | L | L | L | L | L | L | L | L | L | L | L | L | L | L | L | L | L | L |
| 1 | V681 | K | W | K | S | F | L | K | T | F | K | S | A | V | K | T | V | L | H | T | A | L | K | A | I | S | S |
| 27 | F9 to K9 | K | W | K | S | F | L | K | T | K | K | S | A | V | K | T | V | L | H | T | A | L | K | A | I | S | S |
| 28 | F5 to K5 | K | W | K | S | K | L | K | T | F | K | S | A | V | K | T | V | L | H | T | A | L | K | A | I | S | S |
| 29 | F9 to A$_D$9 | K | W | K | S | F | L | K | T | A$_D$ | K | S | A | V | K | T | V | L | H | T | A | L | K | A | I | S | S |
| 30 | F5 to A$_D$5 | K | W | K | S | A$_D$ | L | K | T | F | K | S | A | V | K | T | V | L | H | T | A | L | K | A | I | S | S |
| 31 | V13 to R13 | K | W | K | S | F | L | K | T | F | K | S | A | R | K | T | V | L | H | T | A | L | K | A | I | S | S |
| 32 | L6-A$_D$6, L21-A$_D$21 | K | W | K | S | F | A$_D$ | K | T | F | K | S | A | V | K | T | V | L | H | T | A | A$_D$ | K | A | I | S | S |
| 33 | L6-K$_L$6, L21-K$_L$21 | K | W | K | S | F | K | K | T | F | K | S | A | V | K | T | V | L | H | T | A | K | K | A | I | S | S |
| 34 | Remove K1 | | W | K | S | F | L | K | T | F | K | S | A | K | K | T | V | L | H | T | A | L | K | A | I | S | S |
| 35 | Remove K1, W2 | | | K | S | F | L | K | T | F | K | S | A | K | K | T | V | L | H | T | A | L | K | A | I | S | S |
| 36 | Remove S25, S26 | K | W | K | S | F | L | K | T | F | K | S | A | K | K | T | V | L | H | T | A | L | K | A | I | | | |
| 37 | Remove I24, S25, S26 | K | W | K | S | F | L | K | T | F | K | S | A | K | K | T | V | L | H | T | A | L | K | A | | | |
| 38 | non-polar face shuffle | K | I | K | S | AD | L | K | T | L | K | S | F | K | K | T | A | A | H | T | L | F | K | V | W | S | S |
| 39 | polar face shuffle | S | W | S | K | F | L | K | K | F | T | K | A | K | S | H | V | L | T | T | A | L | S | A | I | K | K |

*L-enantiomer unless otherwise indicated.

In a preferred embodiment, the molecule (peptide) is helical in a hydrophobic environment. We have used circular dichroism spectroscopy to monitor α-helical structure in 50% trifluoroethanol, a mimic of the hydrophobic environment of the cytoplasmic membrane.

In an embodiment, successful peptides that are helical analogs with the desired biological activities have very little alpha-helical structure in benign medium (a non-denaturing medium like 50 mM PO$_4$ buffer containing 100 mM KCl, pH 7) monitored by circular dichroism spectroscopy. In an embodiment, this structural property can have importance in one or more of several potential mechanisms, for example: a) decreasing dimerization of molecule in benign medium (measured as described herein); b) allowing the peptide to more easily penetrate through the cell wall to reach the membrane of the microbe. Furthermore, disruption of the α-helical structure in benign medium can still allow a positively-charged peptide to be attracted to the negatively-charged cell wall surface of the microbe (e.g. lipopolysaccharide), but the lack of structure can decrease the affinity of peptide for this surface which allows the peptide to more easily pass through the cell wall and enter the interface region of the membrane where the peptide is parallel to the surface of membrane. Here the peptide can be induced by the hydrophobic environment of the membrane into its alpha-helical structure. In this alpha-helical structure, we hypothesize that the non-polar face of the peptide can interact with the hydrophobicity of the membrane, and its polar and positively-charged groups on the polar face can interact with the negatively-charged groups of the phospholipids on the surface of the membrane.

In an embodiment, a peptide is net positively-charged and amphipathic/amphiphilic when in an alpha-helical structure. For example, the alpha-helical peptide has a non-polar face or hydrophobic surface on one side of the molecule and a polar and positively-charged surface on the other side of the molecule; i.e., the molecule is amphipathic. Amphipathicity of the molecule can be calculated as described herein.

Certain peptide analogs were studied by temperature profiling in RP-HPLC from 5° C. to 80° C., to evaluate the self-associating ability of the molecules in solution. The ability to self-associate can be another important parameter in understanding peptide antimicrobial and hemolytic activities. It was generally found that a high ability to self-associate in solution was correlated with weak antimicrobial activity and strong hemolytic activity of the peptides. Biological studies showed that strong hemolytic activity of the peptides generally correlated with high hydrophobicity, high amphipathicity and high helicity. In most cases, the D-amino acid substituted peptides possessed an enhanced average antimicrobial activity compared with L-diastereomers. As illustrated herein, the therapeutic index of V$_{681}$ was improved 90-fold and 23-fold against gram-negative and gram-positive bacteria, respectively (using geometric mean comparison). By replacing the central hydrophobic or hydrophilic amino acid residue on the nonpolar or the polar face of these amphipathic molecules with a series of selected D- and L-amino acids, we further demonstrate that this method can be used for the rational design of other antimicrobial peptides with enhanced activities.

The antimicrobial peptides exemplified in the present invention contain amino acid substitutions in at least one of the two positions selected from the group represented as a and b in the peptide sequence given as KWKSFLKTFKaA bKTVLHTALKAISS (SEQ ID NO: 40) wherein a and b are selected from the group consisting of L-leucine, D-leucine, L-valine, D-valine, L-alanine, D-alanine, glycine, L-serine, D-serine, L-lysine, and D-lysine (L,A,S,V,K in L- and D-enantiomeric form and G). Particularly preferred antimicrobial peptides are referred to herein as $NK_L$, $D-NK_D$, $NA_D$, and $D-NA_L$ and contain the following amino acid sequences. A most particularly preferred antimicrobial peptide is referred to herein as $D-NK_D$. In an alternative nomenclature, $D-NK_D$ can be referred to as $D-V13K_D$.

| Peptide name | Amino acid sequence (one letter code) |
| --- | --- |
| $NK_L$ | Ac-$K_L$-$W_L$-$K_L$-$S_L$-$F_L$-$L_L$-$K_L$-$T_L$-$F_L$-$K_L$-$S_L$-$A_L$-[$K_L$]-$K_L$-$T_L$-$V_L$-$L_L$-$H_L$-$T_L$-$A_L$-$L_L$-$K_L$-$A_L$-$I_L$-$S_L$-$S_L$-amide (SEQ ID NO: 6) |
| $D-NK_D$ | Ac-$K_D$-$W_D$-$K_D$-$S_D$-$F_D$-$L_D$-$K_D$-$T_D$-$F_D$-$K_D$-$S_D$-$A_D$-[$K_D$]-$K_D$-$T_D$-$V_D$-$L_D$-$H_D$-$T_D$-$A_D$-$L_D$-$K_D$-$A_D$-$I_D$-$S_D$-$S_D$-amide (SEQ ID NO: 24) |
| $NA_D$ | Ac-$K_L$-$W_L$-$K_L$-$S_L$-$F_L$-$L_L$-$K_L$-$T_L$-$F_L$-$K_L$-$S_L$-$A_D$-[$A_D$]-$K_L$-$T_L$-$V_L$-$L_L$-$H_L$-$T_L$-$A_L$-$L_L$-$K_L$-$A_L$-$I_L$-$S_L$-$S_L$-amide (SEQ ID NO: 9) |
| $D-NA_L$ | Ac-$K_D$-$W_D$-$K_D$-$S_D$-$F_D$-$L_D$-$K_D$-$T_D$-$F_D$-$K_D$-$S_D$-$A_D$-[$A_L$]-$K_D$-$T_D$-$V_D$-$L_D$-$H_D$-$T_D$-$A_D$-$L_D$-$K_D$-$A_D$-$I_D$-$S_D$-$S_D$-amide (SEQ ID NO: 25) |

Here a subscript D following an amino acid residue denotes that the residue is a D-amino acid residue; similarly a subscript L denotes an L-amino acid residue. In the peptide name, an initial D- (not subscripted) denotes all D-amino acids in the peptide except where specified (e.g. $D-NA_L$ denotes all D-amino acids with the exception of a single substitution of L-Ala in the center of the non-polar face specified by N). The boxed residues denote the differences at position 13 in the sequence which is in the center of the non-polar face (see FIG. 1).

In an embodiment, a peptide of the invention is integrated in a larger peptide or protein. In an embodiment, a peptide of the invention is covalently or non-covalently associated with another composition. In a particular embodiment, said another composition is a polymer.

The peptides disclosed have antimicrobial activity against a wide range of microorganisms including gram-positive and gram-negative bacteria. Detailed description of the microorganisms belonging to gram-positive and gram-negative bacteria can be found in Medical Microbiology (1991), $3^{rd}$ edition, edited by Samuel Baron, Churchill Livingstone, New York. Examples of potentially susceptible bacteria include, but are not limited to, *Escherichia coli, Salmonella typhimurium, Pseudomonas aeruginosa, Staphylococcus aureus, Staphylococcus epidermidis, Bacillus subtilis, Enterococcus faecalis, Corynebacterium xerosis*, and *Bacillus anthracis*. The antimicrobial activities of the inventive peptides have been demonstrated herein against the fore-mentioned gram-positive and gram-negative bacteria because it is well known in the art that these bacteria are considered as model organisms for either gram-negative or gram-positive bacteria and thus any biological activity demonstrated again these model organisms are accepted as an indication of that demonstrated activity against the entire family of gram-negative or gram-positive bacteria.

The antimicrobial peptides of the invention are useful as bactericides and/or bacteriostats for modification of infectivity, killing microorganisms, or inhibiting microbial growth or function and thus useful for the treatment of an infection or contamination caused by such microorganisms.

Also provided are therapeutic or otherwise active compositions suitable for human, veterinary, agricultural or pharmaceutical use, comprising one or more of the antimicrobial peptides of the invention and a suitable pharmaceutical carrier. Such therapeutic compositions can be formulated and administered as known in the art, e.g., for oral, parenteral or topical application for controlling and/or preventing infection by a wide range of microorganisms including gram-positive and gram-negative bacteria.

In an embodiment of the invention, in vitro antimicrobial activity of these peptides demonstrated herein is an accurate predictor of in vivo antimicrobial activity.

Pharmaceutical compositions contain a therapeutically effective amount of one or more of the antimicrobial peptides and a suitable carrier. A therapeutically effective amount of an antimicrobial peptide can be readily determined according to methods well known in the art. For example, the amount will vary depending on the severity of an infection, subject parameters such as the age and the size/weight of a subject with an actual or potential infection of a given microorganism, and the route of administration and the like.

The present invention relates to compositions comprising one or more antimicrobial peptides of the invention in a microbicidal effective amount and a pharmaceutically acceptable carrier. Such compositions may additionally comprise a detergent. The addition of a detergent to such peptide compositions is useful to enhance antibacterial characteristics of the peptides. Although any suitable detergent may be used, the presently preferred detergent is a nonionic detergent such as Tween 20 or 1% NP40. Such antimicrobial pharmaceutical compositions can be formulated and administered in ways, as understood in the art for use local or systemic injection, for oral or topical application. In an embodiment, the antimicrobial peptides of the present invention can comprise from 0.0001% to 50% by weight of such compositions.

It will be understood that a composition for application, e.g. by systemic injection, will contain an antimicrobial peptide in a therapeutically effective amount or a therapeutically effective amount of an antimicrobial peptide can be conjugated to another molecule with specificity for the target cell type. The other molecule can be an antibody, ligand, receptor, or other recognition molecule. In an embodiment, the choice of the peptide is made with consideration of immunogenicity and toxicity for an actually or potentially infected host, effective dose of the peptide, and the sensitivity of the target microbe to the peptide, as known in the art.

In an embodiment, the method of inhibiting the growth of bacteria using the peptides of the invention may further include the addition of one or more other antimicrobial agents (e.g. a conventional antibiotic) for combination or synergistic therapy. The appropriate amount of the peptide administered will typically depend on the susceptibility of a bacterium such as whether the bacterium is Gram negative or Gram positive, and will be easily discernable by one of ordinary skill in the art.

In an embodiment the invention also provides a composition that comprises the peptide, in an amount effective to kill a microorganism, and a suitable carrier. Such compositions may be used in numerous ways to combat microorganisms, for example in household or laboratory antimicrobial formulations using carriers well known in the art.

In an embodiment, the invention provides a peptide comprising SEQ ID NO:2. In an embodiment, the invention provides a peptide comprising a derivative of SEQ ID NO:1. In an embodiment, the invention provides a peptide selected from the group consisting of SEQ ID NO:2, 4-14, 16-25, and a derivative thereof. In an embodiment, a derivative comprises a substitution of at least one amino acid residue. In an embodiment, a derivative includes a substitution of at least one amino acid residue; excepting SEQ ID NO:1. In an embodiment, a derivative comprises a truncation of at least one residue from an end. In an embodiment, a derivative comprises a truncation of at least two residues from an end. In an embodiment, a substitution replaces a hydrophilic residue for a hydrophobic residue. In an embodiment, a substitution replaces a hydrophobic residue for a hydrophilic residue. In an embodiment, a substitution replaces a hydrophilic residue with a different hydrophilic residue. In an embodiment, a substitution replaces a hydrophilic residue with a different hydrophilic residue. In an embodiment, a substitution replaces a residue with a different residue having a similar property, e.g., a polar side chain, a positively charged side chain, a negatively charged side chain, etc. In an embodiment, a substitution replaces an L-residue with a D-residue. In an embodiment, a substitution replaces a D-residue with an L-residue. In an embodiment, all residues are D-residues.

In an embodiment, the invention provides a peptide comprising a sequence KWKSFLKTFKaAbKTVLHTALKAISS (SEQ ID NO:40) wherein a and b are selected from the group consisting of L-leucine, D-Leucine, L-valine, D-valine, L-alanine, D-alanine, glycine, L-serine, D-serine, L-lysine, and D-lysine. In an embodiment, the peptide excludes SEQ ID NO:1.

In an embodiment, the invention provides peptide compositions as described herein, including fragments thereof; wherein the fragment length comprises a continuous stretch of at least about 14, at least about 17, at least about 20, at least about 23, at least about 24, or at least about 25 amino acids. In an embodiment, the invention provides a peptide composition wherein said composition is at least about 70%, at least about 80%, at least about 90%, or at least about 95% homologous to a sequence of a peptide described herein. In an embodiment, the invention provides a nucleic acid capable of encoding a peptide described herein. In an embodiment, a peptide of the invention is intended to be exclusive of one or more of the following peptides: SEQ ID NO:1, SEQ ID NO:3, SEQ ID NO:15, and SEQ ID NO:26. In a particular embodiment, a peptide of the invention is exclusive of SEQ ID NO:1.

Where the peptides are to be used as antimicrobial agents, they can be formulated, for example, in buffered aqueous media containing a variety of salts and buffers. Examples of the salts include, but are not limited to, halides, phosphates and sulfates, e.g., sodium chloride, potassium chloride or sodium sulfate. Various buffers may be used, such as citrate, phosphate, HEPES, Tris or the like to the extent that such buffers are physiologically acceptable to the host that is being treated.

Various excipients or other additives may be used, where the peptides are formulated as lyophilized powders, for subsequent use in solution. The excipients may include various polyols, inert powders or other extenders.

"Therapeutically effective" as used herein, refers to an amount of formulation, composition, or reagent, optionally in a pharmaceutically acceptable carrier, that is of sufficient quantity to ameliorate the state of the patient or animal so treated. "Ameliorate" refers to a lessening of the detrimental effect of the disease state or disorder in the recipient of the therapy. In an embodiment, a peptide of the invention is administered to a subject in need of treatment.

Pharmaceutically acceptable carrier preparations for administration include sterile or aqueous or nonaqueous solutions, suspensions, and emulsions. Examples of nonaqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solutions, Ringer's dextrose, dextrose and sodium chloride, lactated Ringer's, or fixed oils. Active therapeutic ingredients are often mixed with excipients that are pharmaceutically acceptable and compatible with the active ingredients. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antioxidants, chelating agents, and inert gases and the like. The actual dosage of the peptides, formulations or compositions containing such peptides can depend on many factors, including the size/weight, age, and health of an organism, however, one of ordinary skill in the art can use the following teachings and others known in the art describing the methods and techniques for determining clinical dosages (Spiker B., Guide to Clinical Studies and Developing Protocols, Raven Press, Ltd., New York, 1984, pp. 7-13, 54-60; Spiker B., Guide to Clinical Trials, Raven Press, Ltd., New York 1991, pp. 93-101; C. Craig. and R. Stitzel, eds., Modern Pharmacology, 2d ed., Little, Brown and Co., Boston, 1986, pp. 127-133; T. Speight, ed., Avery's Drug Treatment: Principles and Practice of Clinical Pharmacology and Therapeutics, 3d ed., Williams and Wilkins, Baltimore, 1987, pp. 50-56; R. Tallarida, R. Raffa and P. McGonigle, Principles in General Pharmacology, Springer-Verlag, new York, 1988, pp. 18-20) to determine the appropriate dosage to use.

In an embodiment, the following dosages are used: generally in the range of about 0.001 mg/kg to about 100 mg/kg and preferably from about 0.001 mg/kg to about 1 mg/kg final concentration are administered per day to an adult in any pharmaceutically acceptable carrier.

In another embodiment, the present invention may be used as a food preservative or in treating food products to control, reduce, or eliminate potential pathogens or contaminants. A peptide of the invention may be used as a disinfectant, for use in or with any product that must remain microbial free or be within certain tolerances. In an embodiment, treatment with a peptide provides at least partial regulation of infection or contamination.

In an embodiment it is also possible to incorporate or distribute the peptides within materials, on devices, or on objects (e.g. on an accessible surface), where microbial growth or viable presence is undesirable, as a method of microbicidal or microbistatic inhibition of microbial growth by administering to the devices or objects a microbicidal or microbistatic effective amount of peptide. In an embodiment, such devices or objects include, but are not limited to, linens, cloth, plastics, latex fabrics, natural rubbers, implantable devices, surfaces, or storage containers.

In an embodiment, the invention provides a method of disinfecting a surface of an article, said method comprising the step of applying to said surface an effective amount of a composition comprising at least one microbial peptide of the invention. In an embodiment, the invention provides a disinfecting solution comprising at least one microbial peptide of the invention and optionally an acceptable carrier.

BRIEF DESCRIPTION OF THE DRAWINGS

FIG. 7 illustrates further peptide analogs including those generated by variations based on several techniques: the position of substitutions, nature of substitutions, multiple substitutions, truncations, and shuffling. FIG. 7A illustrates specific peptide sequences.

DETAILED DESCRIPTION OF THE INVENTION

Figure 1:
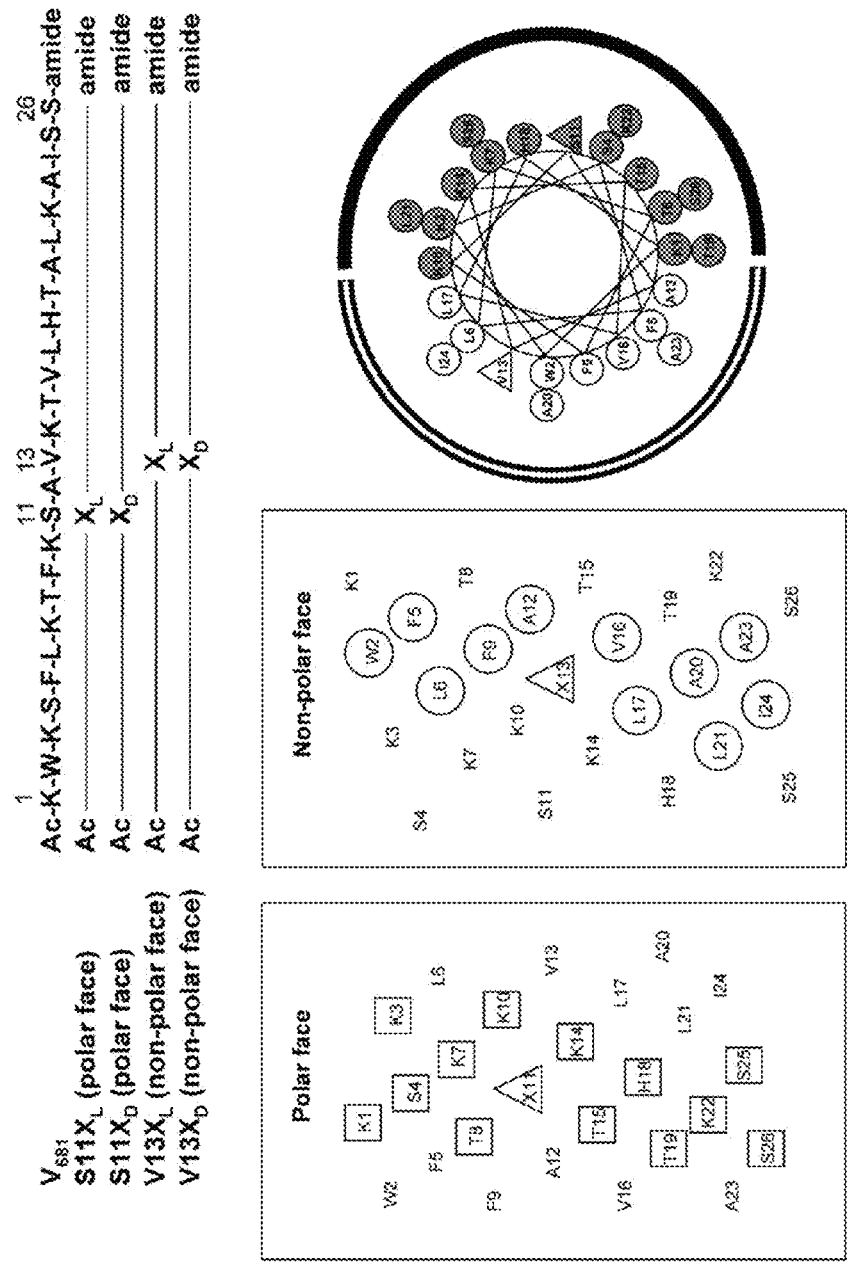
FIG. 1 illustrates the "host" peptide $V_{681}$ (SEQ ID NO:1) as a helical wheel/nets and the sequences of the synthetic peptide analogs used in the present studies. Shown are the polar/hydrophilic face (boxed residues) and non-polar/hydrophobic face (circled residues). The hydrophobic face is indicated as an open arc, whilst the hydrophilic face is shown as a solid arc in the helical wheel. The substitution sites are at position 11 (triangled) on the polar face and position 13 (triangled) on the non-polar face. In the peptide sequences, $X_L$ and $X_D$ denote the L- or D-substituting amino acids. P denotes the polar face and N denotes the non-polar face. Ac denotes $N_\alpha$-acetyl and amide denotes $C_\alpha$-amide. One-letter codes are used for the amino acid residues.

In general the terms and phrases used herein have their art-recognized meaning, which can be found by reference to standard texts, journal references and contexts known to those skilled in the art. The following definitions are provided to clarify their specific use in the context of the invention.

When used herein, the term "amino acid" is intended to refer to any natural or unnatural amino acid, whether made naturally or synthetically, including any such in L- or D-configuration. The term can also encompass amino acid analog compounds used in peptidomimetics or in peptoids. The term can include a modified or unusual amino acid or a synthetic derivative of an amino acid, e.g. diamino butyric acid and diamino propionic acid and the like.

The antimicrobial peptides of the invention are composed of amino acids linked together by peptide bonds. The peptides are in general in alpha helical conformation under hydrophobic conditions. Sequences are conventionally given from the amino terminus to the carboxyl terminus. Unless otherwise noted, the amino acids are L-amino acids. When all the amino acids are of L-configuration, the peptide is said to be an L-enantiomer. When all the amino acids are of D-configuration, the peptide is said to be a D-enantiomer.

The term "minimal inhibitory concentration" (MIC) refers to the lowest concentration of an antimicrobial agent (e.g., a peptide) required to prevent growth or otherwise modify a function of a microorganism under certain conditions, for example in liquid broth medium, and can be determined for a number of different microorganisms according to standard techniques well known in the art.

The term "minimal hemolytic concentration" (MHC) refers to the lowest concentration of an agent or peptide required to cause hemolysis of blood cells. MHC can be determined with red blood cells (RBC) from various species including human red blood cells (hRBC).

The term "therapeutic index" (TI) is the ratio of minimal hemolytic concentration (MHC) over minimal inhibitory concentration (MIC) of an antimicrobial agent. Larger values generally indicate greater antimicrobial specificity.

The term "stability" can refer to an ability to resist degradation, to persist in a given environment, and/or to maintain a particular structure. For example, a peptide property of stability can indicate resistance to proteolytic degradation and to maintain an alpha-helical structural conformation.

The following abbreviations are used herein: A, Ala, Alanine; M, Met, Methionine; C, Cys, Cysteine; D, Asp, Aspartic Acid; E, Glu, Glutamic Acid; F, Phe, Phenylalanine; G, Gly, Glycine; H, H is, Histidine; I, Ile, Isoleucine; K, Lys, Lysine; L, Leu, Leucine; N, Asn, Asparagine; P, Pro, Proline; Q, Glu, Glutamine; R, Arg, Arginine; S, Ser, Serine; T, Thr, Threonine; V, Val, Valine; W, Trp, Tryptophan; Y, Tyr, Tyrosine; RP-HPLC, reversed-phase high performance liquid chromatography; MIC, minimal inhibitory concentration; MHC, minimal hemolytic concentration; CD, circular dichroism spectroscopy; TFE, trifluoroethanol; TFA, trifluoroacetic acid; RBC, red blood cells; hRBC, human red blood cells.

The term "antimicrobial activity" refers to the ability of a peptide of the present invention to modify a function or metabolic process of a target microorganism, for example so as to at least partially affect replication, vegetative growth, toxin production, survival, viability in a quiescent state, or other attribute. In an embodiment, the term relates to inhibition of growth of a microorganism. In a particular embodiment, antimicrobial activity relates to the ability of an inventive peptide to kill at least one bacterial species. In a particular embodiment, the bacterial species is selected from the group consisting of gram-positive and gram-negative bacteria. In an embodiment, the term can be manifested as microbicidal or microbistatic inhibition of microbial growth.

The phrase "improved biological property" is meant to indicate that a test peptide exhibits less hemolytic activity and/or better antimicrobial activity, or better antimicrobial activity and/or less hemolytic activity, compared to the control peptide (e.g. $V_{681}$), when tested by the protocols described herein or by any other art-known standard protocols. In general, the improved biological property of the peptide is reflected in the therapeutic index (TI) value which is better that that of the control peptide.

The term "microorganism" herein refers broadly to bacteria, fungi, viruses, and protozoa. In particular, the term is applicable for a microorganism having a cellular or structural component of a lipid bilayer membrane. In specific embodiments, the membrane is a cytoplasmic membrane. Pathogenic bacteria, fungi, viruses, and protozoa as known in the art are generally encompassed. Bacteria can include gram-negative and gram-positive bacteria in addition to organisms classified in orders of the class Mollicutes and the like, such as species of the *Mycoplasma* and *Acholeplasma* genera. Specific examples of potentially sensitive gram-negative bacteria include, but are not limited to, *Escherichia coli, Pseudomonas aeruginosa, Salmonella, Hemophilus influenza, Neisseria, Vibrio cholerae, Vibrio parahaemolyticus* and *Helicobacter pylori*. Examples of potentially sensitive gram-positive bacteria include, but are not limited to, *Staphylococcus aureus, Staphylococcus epidermis, Streptococcus agalactiae*, Group A *streptococcus, Streptococcus pyogenes, Enterococcus faecalis*, Group B gram positive *streptococcus, Corynebacterium xerosis*, and *Listeria monocytogenes*. Examples of potentially sensitive fungi include yeasts such as *Candida albicans*. Examples of potentially sensitive viruses include measles virus, herpes simplex virus (HSV-1 and -2), herpes family members (HIV, hepatitis C, vesicular, stomatitis virus (VSV), visna virus, and cytomegalovirus (CMV). Examples of potentially sensitive protozoa include *Giardia*.

"Therapeutically effective" as used herein, refers to an amount of formulation, composition, or reagent in a pharmaceutically acceptable carrier or a physiologically acceptable salt of an active compound, that is of sufficient quantity to ameliorate the undesirable state of the patient, animal, material, or object so treated. "Ameliorate" refers to a lessening of the detrimental effect of the disease state or disorder, or reduction in contamination, in the receiver of the treatment.

The peptides of the invention have antimicrobial activity by themselves or when covalently conjugated or otherwise coupled or associated with another molecule, e.g., polyethylene glycol or a carrier protein such as bovine serum albumin, so long as the peptides are positioned such that they can come into contact with a cell or unit of the target microorganism. These peptides may be modified by methods known in the art provided that the antimicrobial activity is not destroyed or substantially compromised.

The invention may be further understood by the following non-limiting examples.

EXAMPLE 1

Derivatives of Peptide $V_{681}$ with Modified Activity

In the studies described hereinafter, the 26-residue peptide having the sequence Ac-KWKSFLKTFKS-AVKTVLHTAL-KAISS-amide ($V_{681}$, SEQ ID NO:1) was utilized as the framework to study the effects of peptide hydrophobicity/ hydrophilicity, amphipathicity and helicity by one or more amino acid substitutions in the center of the polar and nonpolar faces of the amphipathic helix on biological activities. These studies demonstrate i) the importance of the peptide self-association parameter in the de novo design of amphipathic α-helical antimicrobial peptides; ii) that disruption of α-helical structure in benign conditions by D-amino acid substitutions or substitutions of hydrophilic/charged L-amino acids on the non-polar face can dramatically alter specificity; and iii) that these substitutions enhance antimicrobial activity, decrease toxicity and improve antimicrobial specificity while maintaining broad spectrum activity for gram-negative and gram-positive bacteria.

Peptide $V_{681}$, a 26-residue amphipathic antimicrobial peptide with a polar and non-polar face (28), was selected as the native parent peptide in this study (FIG. 1). Its polar face consists of 14 residues: six lysine residues, one histidine, four serines, and three threonines. In contrast, the non-polar face consists of 12 residues: three alanines, two valines, three leucines, two phenylalanines, one isoleucine and one tryptophan residue. In this study, we chose D-/L-amino acid substitution sites at the center of the hydrophobic face (position 13) and at the center of the hydrophilic face (position 11) of the helix, such that these substitution sites were also located in the center of the overall peptide sequence. This was based on our previous model peptide studies (26,31,34) that demonstrated that these central location substitutions had the greatest effect on peptide secondary structure. To study the effects of varying hydrophobicity/hydrophilicity on peptide biological activities, in the design of $V_{681}$ analogs, five L-amino acids (Leu, Val, Ala, Ser, Lys) and Gly were selected out of the 20 natural amino acids as the substituting residues, representing a wide range of hydrophobicity. The hydrophobicity of these six amino acid residues decreases in the order Leu>Val>Ala>Gly>Ser>Lys (26). Based on the relative hydrophobicity of amino acid side-chains (26), leucine was used to replace the native valine on the non-polar face to increase peptide hydrophobicity and amphipathicity; alanine was selected to reduce peptide hydrophobicity/amphipathicity while maintaining high helicity; a hydrophilic amino acid, serine, was selected to decrease the hydrophobicity/amphipathicity of $V_{681}$ in the non-polar face; positively-charged lysine was used to decrease further peptide hydrophobicity and amphipathicity. In contrast, the same amino acid substitutions on the polar face would have different effects on the alteration of hydrophobicity/hydrophilicity and amphipathicity, since the native amino acid residue is serine on the polar face of $V_{681}$. As a result, on the polar face, leucine, valine and alanine were used to increase peptide hydrophobicity as well as decrease the amphipathicity of $V_{681}$, while lysine was selected to increase peptide hydrophilicity and amphipathicity. Previously, Kondejewski et al. (20, 35) and Lee et al. (25) successfully utilized D-amino acid substitutions to dissociate the antimicrobial activity and hemolytic activity of gramicidin S analogs. In the present study, D-enantiomers of the five L-amino acid residues were also incorporated at the same positions on the non-polar/polar face of $V_{681}$ to change not only peptide hydrophobicity/hydrophilicity and amphipathicity but, more importantly, disrupt peptide helical structure. Since glycine does not exhibit optical activity and has no side-chain, the Gly-substituted analog was used as a reference for diastereomeric peptide pairs.

Since most peptide analogs were made based on a single amino acid substitution in either the polar or nonpolar faces of $V_{681}$, peptides were divided into two categories, N-peptides (nonpolar face substitutions) and P-peptides (polar face substitutions). Each peptide was named after the substituting amino acid residue, e.g., the peptide analog with L-leucine substitution on the nonpolar face of $V_{681}$ is called $NL_L$. It is important to note that since the L-valine of the non-polar face and L-serine of the polar face are the original amino acid residues in the $V_{681}$ sequence (FIG. 1), peptide analogs $NV_L$ and $PS_L$ are the same peptide as $V_{681}$.

A control peptide (peptide C) designed to exhibit negligible secondary structure, i.e., a random coil, was employed as a standard peptide for temperature profiling during RP-HPLC to monitor peptide dimerization. As shown in the previous study (29), this 18-residue peptide, with the sequence of Ac-ELEKGGLEGEKGGKELEK-amide (SEQ ID NO:26) clearly exhibited negligible secondary structure, even in the presence of the strong alpha-helix inducing properties of 50% trifluoroethanol (TFE) and at the low temperature of 5° C. ($[\theta]_{222}$=−3,950).

To determine the secondary structure of peptides in different environments, circular dichroism (CD) spectra of the peptide analogs were measured under physiologically related pH and ionic strength (100 mM KCl, 50 mM aq. $PO_4$, pH 7 referred to as benign conditions) and also in 50% TFE to mimic the hydrophobic environment of the membrane. The native peptide, $V_{681}$, exhibited low alpha-helical content in benign conditions, i.e., $[\theta]_{222}$ of −12,900 compared to −27, 300 in 50% TFE, an increase in α-helical content from 45% to 94%, respectively (Table 3). From Table 3, in benign conditions, D-amino acid substituted peptides generally exhibited considerably less α-helical structure compared to their L-diastereomers. The negligible secondary structure characteristics of the D-peptides underlines the helix-disrupting properties of a single D-amino acid substitution, as demonstrated in our previous model α-helical peptide study (26). On the non-polar face, the native L-Val residue was critical in maintaining α-helical structure. Substitution of L-Val with less hydrophobic amino acids (L-Ala, Gly, L-Ser and L-Lys) dramatically decreased the α-helical structure ($NV_L$, $[\theta]_{222}$ of −12,900 to values ranging from −1,300 to −3,450 for $NS_L$, $NK_L$, NG and $NA_L$) (Table 3). Even the substitution with L-Ala, which is known to have the highest α-helical propensity of all 20 amino acids (34), could not stabilize the α-helical structure. This shows the importance of hydrophobicity on the non-polar face in maintaining the α-helical structure. In contrast, substitution with a more hydrophobic amino acid (L-Leu for L-Val) on the non-polar face significantly increased α-helical structure ($[\theta]_{222}$ for peptide $NL_L$ of −20,600 compared to peptide $NV_Q$ of −12,900). It is noteworthy that, on the non-polar face, the magnitude of the helical content of L-peptides in benign buffer was related to the hydrophobicity of the substituting amino acids, i.e., $NL_L$>$NV_L$>$NA_L$>$NS_L$, $NK_L$, again showing the importance of hydrophobicity on the non-polar face in maintaining the α-helical structure. Due to their helix-disruptive ability, on the non-polar face, the D-amino acid substitutions D-Val and D-Leu dramatically decreased α-helical structure in benign medium compared to their L-counterparts. However, whether L- or D-substitutions were made on the non-polar face, high helical structure could be induced by the hydrophobic environment of 50% TFE, a mimic of the membrane's hydrophobicity and α-helix inducing ability (Table 3). From Table 3, it is clear that, although D-amino acid substituted peptides were strongly induced into helical structure in 50% TFE, they were still generally less helical than the L-diastereomers, indicating that D-substitutions were still destabilizing of α-helical structure compared to their L-diastereomers in a hydrophobic environment.

non-polar face substitutions exhibited a greater range of molar ellipticity values in benign conditions than polar face analogs, demonstrating that the amino acid residues on the non-polar face of the helix played a more important role in peptide secondary structure than those on the polar face. As expected, Gly was destabilizing to α-helical structure whether on the non-polar or polar face due to its low α-helical propensity (34).

Figure 2:
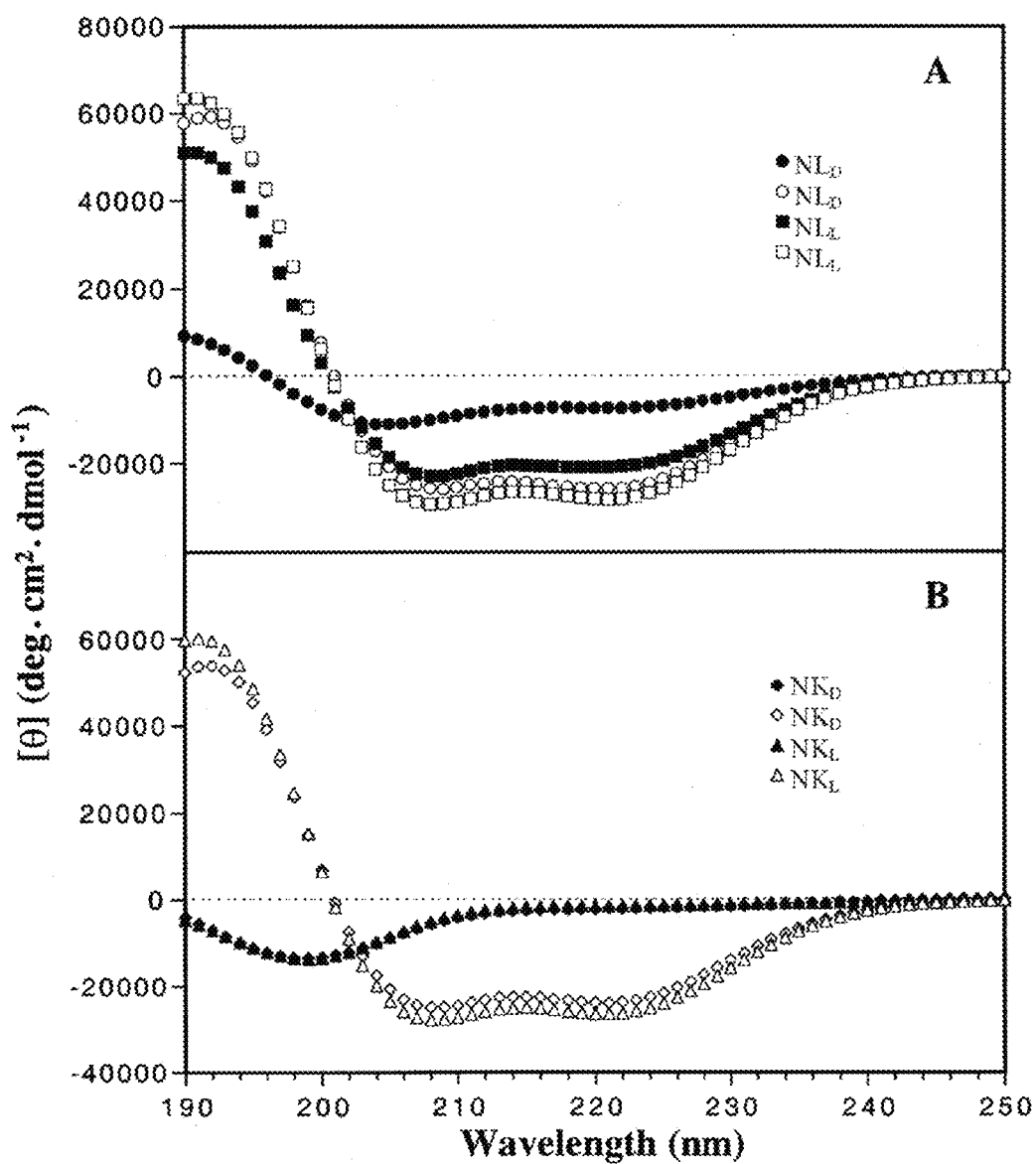
FIG. 2 illustrates graphical results of Circular dichroism (CD) spectra of peptides $NL_D$ and $NL_L$ (panel A) and peptides $NK_D$ and $NK_L$ (panel B) at pH 7 and 25° C., in 50 mM aq. $PO_4$ containing 100 mM KCl. In both Panel A and Panel B, solid symbols represent the CD spectra of peptide analogs in benign buffer without TFE, whilst open symbols represent CD spectra obtained in the presence of 50% TFE. The symbols used are: in Panel A, circle for $NL_D$ and square for $NL_L$; in Panel B, diamond for $NK_D$ and triangle for $NK_L$.

FIG. 2 shows the CD spectra of the most and the least hydrophobic substitutions on the non-polar face. In benign conditions, peptide $NL_D$ showed much less helical structure than $NL_L$ due to the helix-destabilizing ability of the D-amino

TABLE 3

Circular dichroism data of V681 peptide analogs.

| | Benign[b] | | | | 50% TFE[d] | | | |
|---|---|---|---|---|---|---|---|---|
| | $X_L$[e] | | $X_D$[e] | | $X_L$[e] | | $X_D$[e] | |
| Peptides[a] | $[\theta]_{222}$ | % helix[c] | $[\theta]_{222}$ | % helix[c] | $[\theta]_{222}$ | % helix[c] | $[\theta]_{222}$ | % helix[c] |
| NL | −20,600 | 71 | −7,350 | 25 | −28,250 | 98 | −25,750 | 89 |
| NV[f] | −12,900 | 45 | −2,800 | 10 | −27,300 | 94 | −26,000 | 90 |
| NA | −3,450 | 12 | −2,850 | 10 | −28,950 | 100 | −24,650 | 85 |
| NS | −1,300 | 4 | −1,700 | 6 | −27,550 | 95 | −22,200 | 77 |
| NK | −1,450 | 5 | −2,000 | 7 | −26,250 | 91 | −23,600 | 82 |
| NG | −2,250 | 8 | | | −24,350 | 84 | | |
| PL | −10,850 | 37 | −2,950 | 10 | −28,550 | 99 | −26,100 | 90 |
| PA | −13,600 | 47 | −3,050 | 11 | −27,600 | 95 | −27,300 | 94 |
| PS[f] | −12,900 | 45 | −2,800 | 10 | −27,300 | 94 | −26,000 | 90 |
| PV | −7,550 | 26 | −2,400 | 8 | −23,050 | 80 | −20,800 | 72 |
| PK | −5,950 | 21 | −2,500 | 9 | −27,350 | 94 | −27,800 | 96 |
| PG | −4,550 | 16 | | | −25,950 | 90 | | |

[a]Peptides are ordered by relative hydrophobicity to the native analog $V_{681}$ at 5° C. N denotes non-polar face; P denotes polar face (FIG. 1)
[b]The mean residue molar ellipticities, $[\theta]_{222}$, (deg.cm$^2$.dmol$^{-1}$) at wavelength 222 nm were measured at 25° C. in benign buffer (100 mM KCl, 50 mM PO$_4$ pH 7.0).
[c]The helical content (in percentage) of a peptide relative to the molar ellipticity value of the peptide $NA_L$ in 50% trifluoroethanol (TFE).
[d]The mean residue molar ellipticities (deg.cm$^2$.dmol$^{-1}$) at wavelength 222 nm were measured at 25° C. in the benign buffer diluted 1:1 (v/v) with trifluoroethanol (TFE).
[e]$X_L$ and $X_D$ denote the L- and D-substitutions, respectively.
[f]$NV_L$ and $PS_L$ are the same peptide, which is the native peptide $V_{681}$.

In this study, the L-substitutions on the polar face in benign medium had dramatically different effects on α-helical structure than the same substitutions on the non-polar face. For example, $NL_L$ ($[\theta]_{222}$ of −20,600) differed from $PL_L$ ($[\theta]_{222}$ −10,850), indicating that Leu stabilized α-helical structure on the non-polar face and destabilized α-helical structure on the polar face. Similarly, Val destabilized α-helical structure on the polar face; on the other hand, Ala and Ser destabilized helical structure on the non-polar face, whilst, Ala and Ser stabilized α-helical structure when substituted in the polar face, compared to the other amino acid substitutions. Taken together, even though Ala had the highest α-helical propensity of all amino acids (34), its α-helical propensity could not overcome the need for hydrophobicity on the non-polar face ($[\theta]_{222}$ for peptides $NA_L$, −3,450 and $NL_L$, −20,600); whereas, on the polar face, peptide $PA_L$ exhibited high helical structure in benign ($[\theta]_{222}$ −13,600) in contrast to peptide $PL_L$ ($[\theta]_{222}$ −10,850) (Table 3). It is noteworthy that Val and Leu substitutions on the polar face decreased the amphipathicity of the helix as well as increased the hydrophobicity; however, the lower helical content compared with the native $PS_L$ indicated that there should be a balance of amphipathicity and hydrophobicity to enhance the helical content. Similar to the substitutions on the non-polar face, all D-amino acid substitutions on the polar face were destabilizing to α-helical structure in benign medium; however, highly helical structure could be induced by adding 50% TFE. As shown in Table 3, acid; whilst, in 50% TFE, both peptides could be induced to a fully helical structure (FIG. 2, Panel A). In contrast, in benign condition, peptides $NK_L$ and $NK_D$ were random coils, due to the combined effects of decreasing hydrophobicity and amphipathicity by replacing the native L-Val to D-/L-Lys on the non-polar face; again, in 50% TFE, both of them were induced into highly helical structures, albeit that peptide $NK_L$ demonstrated slightly more helical content than peptide $NK_D$.

Next, we prepared the enantiomeric peptides of $V_{681}$ and analogs $NK_L$ and $NA_D$. Peptides $V_{681}$ and $NK_L$ contain all L-amino acids and D-$V_{681}$ and D-$NK_D$ contain all D-amino acids. In the case of $NA_D$ and D-$NA_L$, position 13 is D-alanine and L-alanine, respectively (Table 1). Thus, D-$V_{681}$, D-$NK_D$ and D-$NA_L$ are opposite in stereochemistry to the corresponding L-peptides, $V_{681}$, $NK_L$ and $NA_D$, respectively. A control peptide C designed to exhibit negligible secondary structure, i.e., a random coil, was employed as a standard peptide for temperature profiling during RP-HPLC to monitor peptide dimerization (53, 19, 29).

Figure 3:
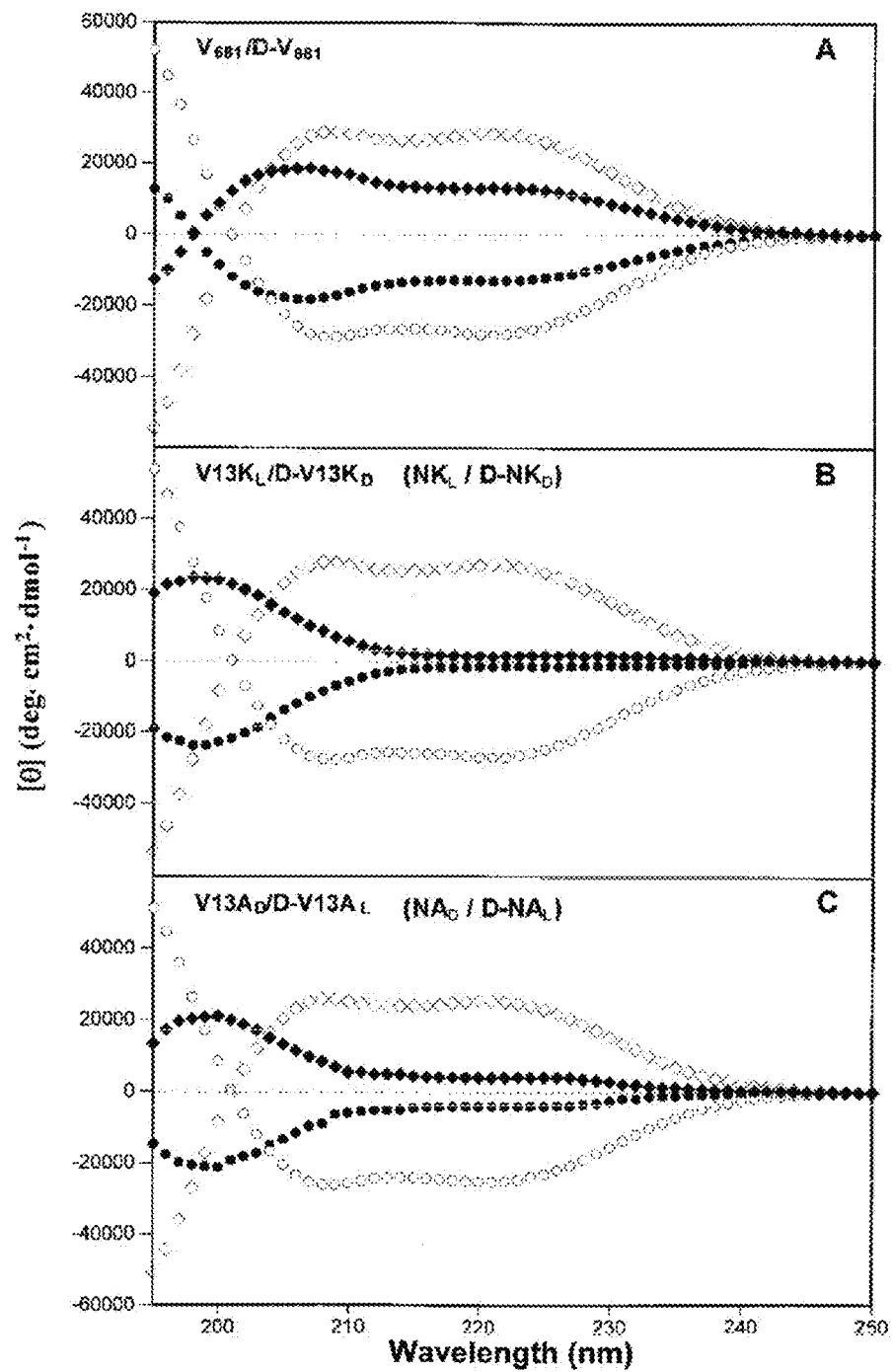
FIG. 3 shows graphical results of Circular dichroism (CD) spectra of peptides $V_{681}$ and D-$V_{681}$ (panel A), $NK_L$ and D-$NK_D$ (panel B) and peptides $NA_D$ and D-$NA_L$ (panel C) at pH 7.4 and 5° C., in 50 mM aq. potassium phosphate buffer (KP buffer) containing 100 mM KCl. In Panels A, B and C, solid symbols represent the CD spectra of peptide analogs in KP buffer without trifluoroethanol (TFE), whilst open symbols represent CD spectra obtained in the presence of 50% TFE; the symbols used are: circles for L-peptides $V_{681}$, $NK_L$ and $NA_D$ and diamonds for D-peptides D-$V_{681}$, D-$NK_L$ and D-$NA_L$.

To determine the secondary structure of the D-enantiomeric peptides in different environments, CD spectra of the peptide analogs were measured under benign conditions (100 mM KCl, 50 mM KH$_2$PO$_4$/K$_2$HPO$_4$, pH 7.4, referred to as KP buffer) and also in 50% trifluoroethanol (TFE) to mimic the hydrophobic environment of the membrane. As shown in FIG. 3, the parent peptide, $V_{681}$, was only partially helical in KP buffer; peptides $NK_L$ and $NA_D$ exhibited negligible secondary structure in KP buffer due to disruption of the nonpolar face of the helix by introducing a hydrophilic L-lysine residue into peptide $NK_L$ or a helix-disruptive D-alanine residue into peptide $NA_D$. However, in the presence of 50% TFE, all three L-peptides were fully folded α-helical structures with similar ellipticities and helicity (Table 4). As expected, the D-peptides showed spectra that were exact mirror images compared to their L-enantiomers, with ellipticities equivalent but of opposite sign both in benign KP buffer and in 50% TFE (Table 4).

TABLE 4

Biophysical data of peptide analogs.

| Peptide[a] | Hydrophobicity[b] | | Benign | | 50% TFE | | $P_A$[e] |
|---|---|---|---|---|---|---|---|
| | $t_{R5}$ (min) | $t_{R80}$ (min) | $[\theta]_{222}$[c] | % helix[d] | $[\theta]_{222}$[c] | % helix[d] | |
| $V_{681}$ | 96.6 | 88.8 | −13000 | 46 | −27950 | 99 | 7.2 |
| D-$V_{681}$ | 96.6 | 88.8 | 13050 | 46 | 28100 | 100 | 7.2 |
| $NA_D$ | 81.2 | 73.2 | −4000 | 14 | −25000 | 89 | 4.1 |
| D-$NA_L$ | 81.2 | 73.2 | 4000 | 14 | 25050 | 89 | 4.1 |
| $NK_L$ | 74.9 | 64.7 | −1400 | 5 | −27000 | 96 | 2.1 |
| D-$NK_D$ | 74.9 | 64.7 | 1500 | 5 | 26950 | 96 | 2.1 |

Peptide sequences are shown in Table 1.
Peptides are ordered by decreasing retention time ($t_R$) in RP-HPLC at pH 2 at temperatures of 5° C. and 80° C. which is a measure of overall hydrophobicity.
The mean residue molar ellipticities, $[\theta]_{222}$, (deg.cm².dmol⁻¹) at wavelength 222 nm were measured at 5° C. in benign conditions (100 mM KCl, 50 mM PO₄ pH 7.4) or in benign buffer containing 50% TFE by circular dichroism spectroscopy. The negative values in molar ellipticity denote the left-handed helices and the positive values denote the right-handed helices.
The helical content (in percentage) of a peptide relative to the molar ellipticity value of the peptide D-$V_{681}$ in the presence of 50% trifluoroethanol (TFE).
$P_A$ denotes the dimerization parameter of each peptide during the RP-HPLC temperature profiling, which is the maximal retention time difference of (($t_R^t$-$t_R^5$ for peptide analogs) − ($t_R^t$-$t_R^5$ for control peptide C)) within the temperature range, and ($t_R^t$-$t_R^5$) is the retention time difference of a peptide at a specific temperature (t) compared with that at 5° C.

Figure 4:
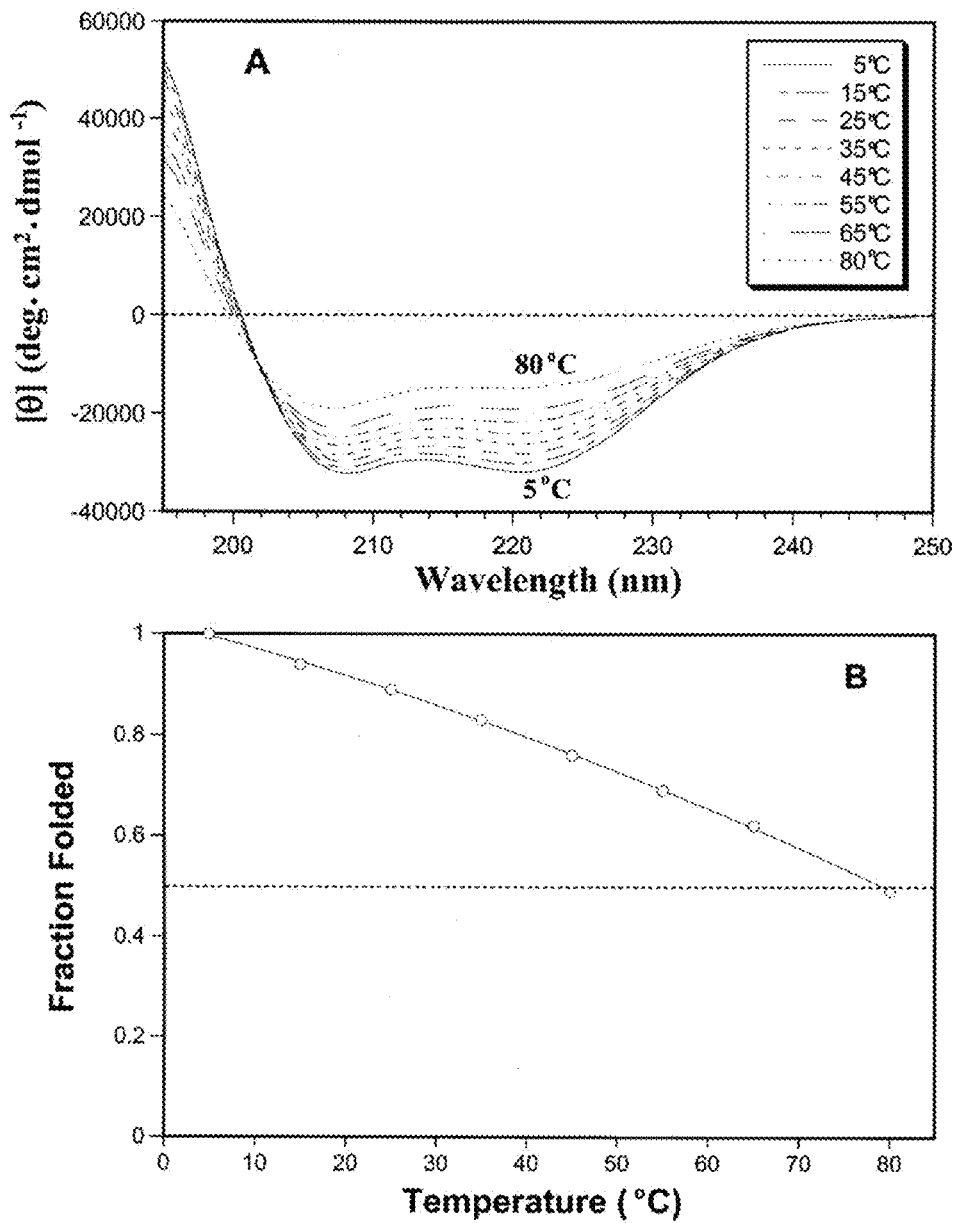
FIG. 4 illustrates the CD temperature denaturation profiles of peptide $V_{681}$. Panel A shows the change of $V_{681}$ helical conformation over the temperature range from 5° C. to 80° C. in the hydrophobic medium. The experiment was carried out in 0.05% aq. TFA (pH 2) in the presence of 50% TFE. CD spectra at different temperatures are shown as different lines in the figure; Panel B: shows the stability plot of peptide $V_{681}$ during CD temperature denaturation.

We next used temperature profiling during RP-HPLC to determine the self-association ability of the various analogs of $V_{681}$ which would occur through interaction of the nonpolar faces of these amphipathic α-helices. Using model amphipathic α-helical peptides with all 20 amino acid substitutions in the center of the non-polar face, we showed previously that the model amphipathic peptides were maximally induced into an α-helical structure in 40% TFE and that the stability of the α-helix during temperature denaturation was dependent on the substitution (26). In order to investigate the stability of $V_{681}$ in a hydrophobic environment, we carried out a temperature denaturation study in solution, as monitored by circular dichroism spectroscopy. We used 50% aqueous TFE in 0.05% TFA to mimic the hydrophobic conditions in the reversed-phase column since the hydrophobic environment of a reversed-phase column (hydrophobic stationary phase and the hydrophobic organic solvent in the mobile phase) could induce α-helical structure in a similar manner to TFE. FIG. 4, panel A shows the change of $V_{681}$ helical conformation over the temperature range from 5° C. to 80° C. in the hydrophobic medium. At 5° C., 50% TFE induced full α-helical structure of $V_{681}$. During the temperature denaturation, the helical content of $V_{681}$ decreased with increasing temperature but even at 80° C. $V_{681}$ remained significantly α-helical. FIG. 4, panel B shows the stability profile of $V_{681}$ with a transition temperature $T_m$ of 79.3° C., where $T_m$ is defined as the temperature when 50% of α-helical structure is denatured compared with the fully folded conformation of the peptide in 50% TFE at 5° C. These data support the view, that during temperature profiling in RP-HPLC, the peptides are fully helical at low temperatures such as 5° C. and can remain in the α-helical conformation at 80° C. in solution during partitioning in RP-HPLC. In addition, due to their hydrophobic preferred binding domains, the peptides will remain α-helical when bound to the hydrophobic matrix. Overall, these results indicate that $V_{681}$ is a very stable α-helical peptide in a hydrophobic environment, whether it is in solution (such as 50% TFE), under the conditions of RP-HPLC or in the hydrophobic environment of the membrane.

It is well documented that the formation of a hydrophobic binding domain due to peptide secondary structure can affect peptide interactions with reversed-phase matrices, this effect having been observed especially for amphipathic α-helical peptides (26, 36-39). Indeed, Zhou et al. (39) clearly demonstrated that, because of this preferred binding domain, amphipathic α-helical peptides are considerably more retentive than non-amphipathic peptides of the same amino acid composition. In addition, the chromatography conditions characteristic of RP-HPLC (hydrophobic stationary phase, nonpolar eluting solvent) are able to induce and stabilize helical structure in potentially helical polypeptides (39-41) in a manner similar to that of the helix-inducing solvent TFE. From FIG. 1, it can be seen that the substitution site at position 13, in the center of the nonpolar face of the helix, ensures a maximal effect on the intimate interaction of the substituting side-chain with the reversed-phase stationary phase; thus, any differences in effective hydrophobicity via amino acid substitutions in the preferred binding domain can be readily monitored through consequent differences in RP-HPLC retention time.

Figure 5:
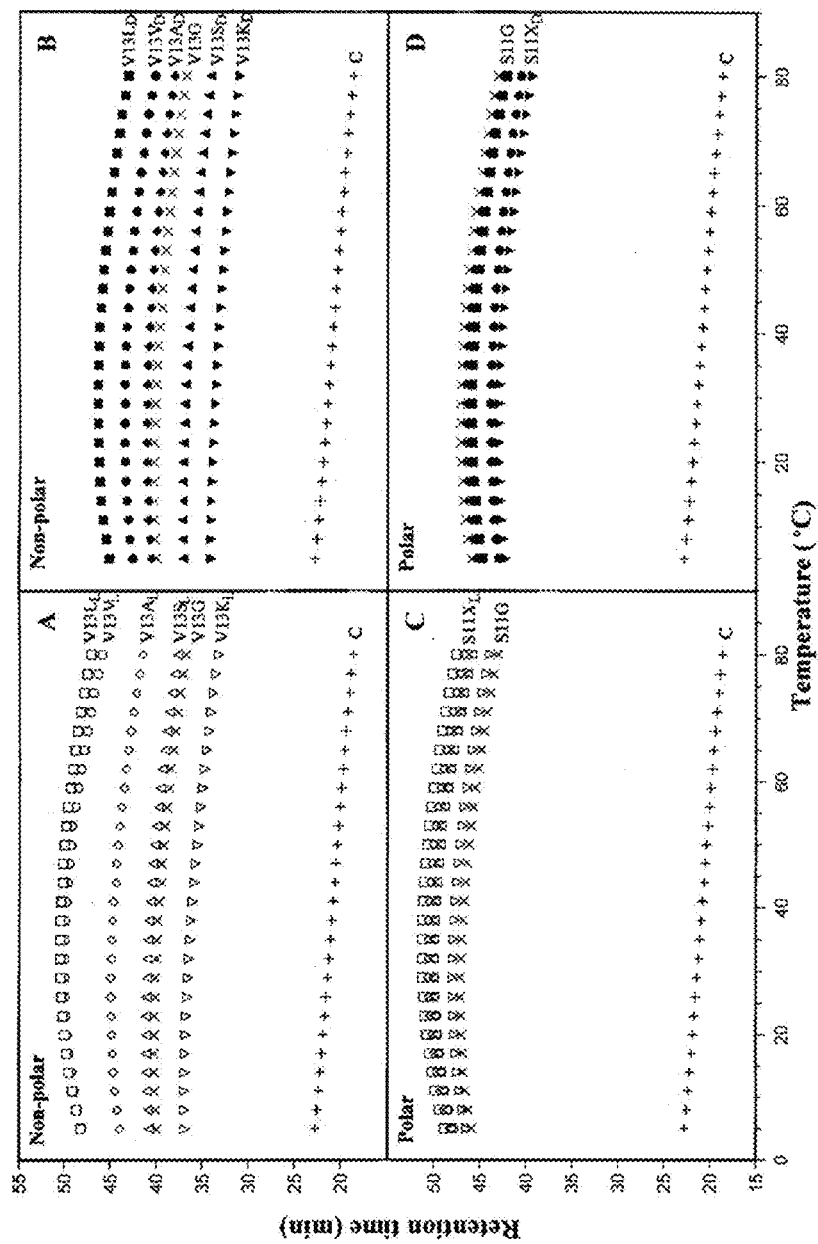
FIG. 5 illustrates the RP-HPLC temperature profiles of peptide $V_{681}$ and its analogs. Conditions: RP-HPLC, narrow-bore SB-$C_8$ column (150×2.1 mm ID; 5 μm particle size, 300 Å pore size), linear A-B gradient (1% acetonitrile/min) at a flow-rate of 0.25 ml/min, where eluent A is 0.05% aqueous TFA and eluent B is 0.05% TFA in acetonitrile. Retention data has been collected in 3° C. increments within the temperature range from 5° C. to 80° C. Open symbols represent the temperature profiles of L-amino acid substituted peptides on either the non-polar or polar face of $V_{681}$ (panels A and C); whereas solid symbols represent the temperature profiles of D-amino acid substituted peptides on either the non-polar or polar face of $V_{681}$ (panels B and D). In all panels, the substituting amino acids used in either the non-polar or polar face of $V_{681}$ are Val (circle), Leu (square), Ala (diamond), Ser (triangle), Lys (inverted triangle) and Gly (X). The temperature profile of the random coil control peptide (C1) is shown in the figure (+).
Figure 6:
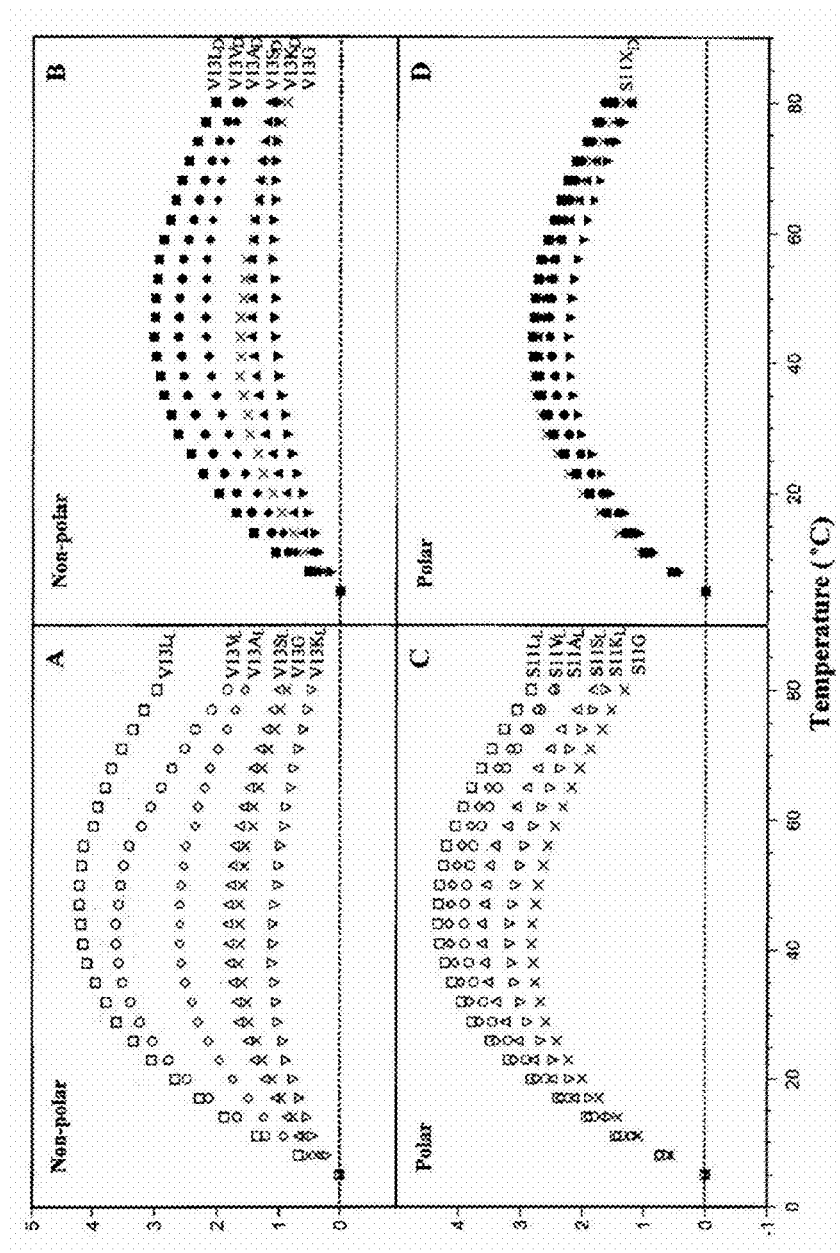
FIG. 6 illustrates the normalized RP-HPLC temperature profiles of peptide $V_{681}$ and its analogs. Temperature profiles normalized to retention behavior of random coil peptide C1. Column and conditions: see FIG. 4. The retention behavior of the peptides was normalized to that of the random coil peptide C1 through the expression ($t_R^t$-$t_R^5$ for peptides) minus ($t_R^t$-$t_R^5$ for C1), where $t_R^t$ are the retention times at a specific temperature of an antimicrobial peptide or the random coil peptide, and $t_R^5$ are the retention times at 5° C. Open symbols represent the temperature profiling of L-amino acid substituted peptides on either the non-polar or polar face of $V_{681}$ (panels A and C); whereas solid symbols represent D-amino acid substituted peptides on either the non-polar or polar face of $V_{681}$ (panels B and D). In all panels, amino acids used for substitution in either the non-polar or polar face of $V_{681}$ are Val (circle), Leu (square), Ala (diamond), Ser (triangle), Lys (inverted triangle) and Gly (X).

The retention time data for the peptides is shown in Table 5 which records retention times at 5° C., the maximal retention times and retention times at 80° C. during the temperature profiling. Temperatures of 5° C. and 80° C. were the lower and upper temperature limits of temperature profiling in RP-HPLC, representing dimerization of the peptides at 5° C. and the monomerization of peptides at 80° C. due to dissociation of the dimers. The maximal retention times represent the threshold points at which peptides transform from dimeric to monomeric form. The retention profiles from 5-80° C. are shown in FIG. 5. Among the non-polar face substituted peptides, peptides with more hydrophobic substitutions (whether L- or D-amino acid substitutions) were more retained during RP-HPLC, i.e., peptides were eluted in the order of Lys, Gly, Ser, Ala, Val and Leu (Table 5). In addition, on the non-polar face, the L-analogs were always more retained than the D-diastereomers (Table 5, FIG. 5). Since the aforementioned preferred binding domain of amphipathic helices is actually the non-polar face of the helix, D-peptides had a smaller preferred binding domain compared with L-diastereomers, due to the helix disruptive ability of D-amino acids, resulting in lower retention times during RP-HPLC. In contrast, on the polar face, the elution order of peptides was not correlated with the order of amino acid side-chain hydrophobicity, e.g., $PA_L$ and $PS_L$ were more retained than $PV_L$ (Table 5); $PS_D$ was the most retained peptide among the D-amino acid substituted analogs on the polar face (Table 5). Indeed, on the polar face, peptides $PL_L$ and $PA_L$, with the replacement of L-Ser by L-Leu or L-Ala, had increased overall hydrophobicity as revealed by higher retention times compared with $V_{681}$.

Although amino acid L-Val is much more hydrophobic than L-Ser, the observation that peptide $PV_L$ was less retained than the native peptide $V_{681}$ (with L-Ser at position 11 of the polar face) could be attributed to the helix-disrupting characteristics of the β-branched Val residue (also see Table 3). In contrast, at 80° C., $PV_L$ became better retained than $PS_L$. Due to the unfolding of the helical structure at high temperature, the side-chain hydrophobicity of the substituting amino acid in the peptide plays a more important role in the overall hydrophobicity. In a similar manner to the non-polar face substituted peptides, peptides with D-amino acids substituted into the polar face were dramatically less retained than their L-diastereomers. Due to the effect of the preferred binding domain, peptides with substitutions on the non-polar face had a greater retention time range than those with polar face substitutions, e.g., 11.31 min for the L-peptides with non-polar face substitutions versus 2.40 min for the L-peptides with polar face substitutions at 5° C., and 11.05 min versus 3.27 min for the D-peptides with non-polar or polar face substitutions, respectively, at 5° C. (Table 5).

Figure 8:
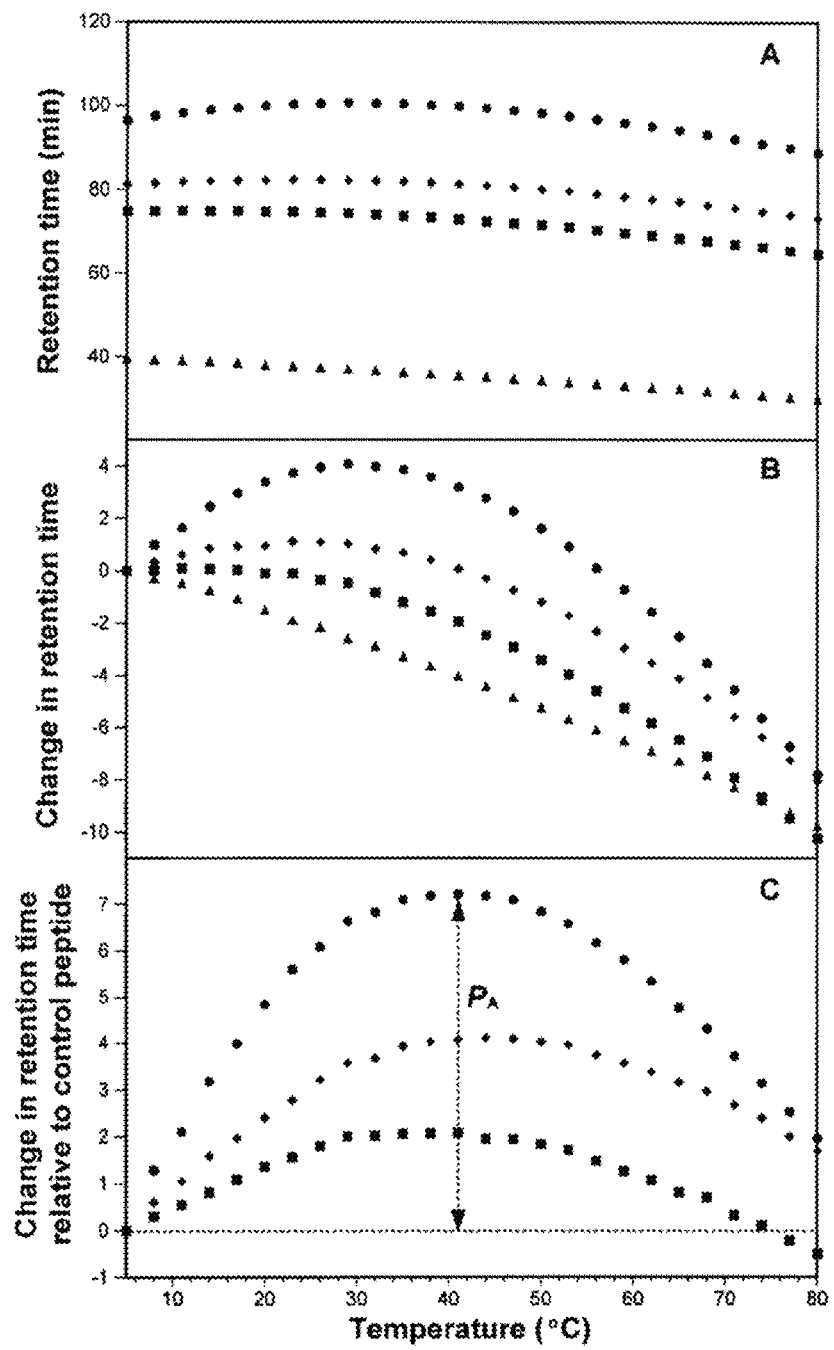
FIG. 8 illustrates the peptide retention behavior during RP-HPLC with increasing temperature. Column and conditions: RP-HPLC, SB-$C_8$ column (150×2.1 mm ID; 5 μm particle size, 300 Å pore size), linear A-B gradient (0.5% acetonitrile/min) at a flow-rate of 0.35 ml/min, where eluent A is 0.2% aqueous TFA and eluent B is 0.2% TFA in acetonitrile. The retention times of the peptides during the change of temperature are shown in Panel A. In Panel B, the retention time of peptides are normalized to 5° C. through the expression ($t_R^t$-$t_R^5$), where $t_R^t$ is the retention time at a specific temperature of an antimicrobial peptide or the random coil peptide, and $t_R^5$ is the retention time at 5° C. In Panel C, the retention behavior of the peptides was normalized to that of the random coil peptide C through the expression ($t_R^t$-$t_R^5$ for peptides) minus ($t_R^t$-$t_R^5$ for C). In Panels A, B and C, the symbols used are: circles for $V_{681}$ and D-$V_{681}$, diamonds for $NA_D$ and D-$NA_L$, squares for $NK_L$, D-$NK_D$ and triangles for random coil peptide C.

The ability of the D-peptides to self-associate was determined by RP-HPLC temperature profiling. FIG. 8A shows the change in RP-HPLC retention times of the three pairs of enantiomers and the control peptide C over a temperature range of 5° C. to 80° C. As expected, L- and D-peptide enantiomers were totally inseparable over this temperature range, since each pair of peptides is identical in sequence and must adopt identical conformations on interacting with the reversed-phase matrix, whether in an all-L- or all-D-conformation. RP-HPLC retention behavior has been frequently utilized to represent overall peptide hydrophobicity (53,26). In the present study, the hydrophobicity of the three peptide pairs is in the order $V_{681}/D-V_{681}>NA_L/D-NA_L>NK_L/D-NK_D$ (Table 4), which agrees with the change in hydrophobicity of the substitutions at position 13 in order of the most hydrophobic to the least hydrophobic amino acid residue (Val in $V_{681}$>Ala in NA>Lys in NK) (54). FIG. 8B shows the retention behavior of the peptides after normalization of the retention times to the corresponding retention time at 5° C. in order to highlight differences in the elution behavior of peptides as the temperature is increased from 5° C. to 80° C. For example, the retention times of peptides $V_{681}/D-V_{681}$ increase with increasing temperature (up to ~30° C.) followed by a retention time decrease with a further temperature increase. Such a temperature profile is characteristic of a peptide exhibiting self-association (53, 29, 19). As shown in FIG. 8C, the peptide self-association parameter, $P_A$, represents the maximum change in peptide retention time relative to the random coil peptide C. Since peptide C is a monomeric random coil peptide in both aqueous and hydrophobic media, its retention behavior over the temperature range 5° C. to 80° C. represents only general temperature effects on peptide retention behavior, i.e., a linear decrease in peptide retention time with increasing temperature due to greater solute diffusivity and enhanced mass transfer between the stationary and mobile phases at higher temperatures (55). Thus, after normalization to the retention times of peptide C, the retention behavior of the peptides represents only peptide self-association ability. Note that the higher the $P_A$ value, the greater the self-association ability. The order of peptide self-association ability of the three pairs of peptide enantiomers is identical to the order of peptide hydrophobicity, i.e., $V_{681}/D-V_{681}$ have the highest dimerization ability in solution among the three pairs of peptide enantiomers ($P_A$=7.2, Table 4); in contrast, $NA_D/D-NA_L$ showed a weaker ability to self-associate when compared to $V_{681}/D-V_{681}$ ($P_A$=4.1, Table 4); $NK_L/D-NK_D$ exhibited the lowest dimerization ability ($P_A$=2.1, Table 4). From Table 4, it is also clear that the peptide retention times at 80° C. are dramatically lower than those at 5° C. Apart from the decrease in retention time due to the general temperature effects noted above, unraveling of the α-helix will also occur with increasing temperature, resulting in the loss of the non-polar face of the amphipathic α-helical peptides and, hence, reduced retention times as the peptides become increasingly random coils.

TABLE 5

Relative hydrophobicity and association ability of peptide analogs during RP-HPLC temperature profiling.

| Peptides[a] | $t_R$ (min)[b] | | | | | $P_A$ (min)[d] |
|---|---|---|---|---|---|---|
| | 5° C. | Max | 80° C. | 5° C. | 80° C. | |
| Non-polar[e] | | | | $\Delta t_R$ (X-$NV_L$) (min)[c] | | |
| $NL_L$ | 48.16 | 50.45 | 47.02 | 0.06 | 1.19 | 4.22 |
| $NV_L$[f] | 48.10 | 49.99 | 45.83 | 0 | 0 | 3.63 |
| $NA_L$ | 43.94 | 44.88 | 41.38 | −4.16 | −4.45 | 2.59 |
| $NS_L$ | 40.72 | 41.08 | 37.62 | −7.38 | −8.21 | 1.82 |
| $NK_L$ | 36.85 | 36.91 | 33.22 | −11.25 | −12.61 | 1.10 |
| NG | 39.96 | 40.22 | 36.74 | −8.14 | −9.09 | 1.64 |
| $NL_D$ | 45.10 | 46.37 | 43.03 | −3.00 | −2.80 | 3.02 |
| $NV_D$ | 42.55 | 43.43 | 40.15 | −5.55 | −5.68 | 2.63 |
| $NA_D$ | 40.49 | 41.01 | 38.00 | −7.61 | −7.83 | 2.19 |
| $NS_D$ | 37.02 | 37.12 | 34.08 | −11.08 | −11.75 | 1.46 |
| $NK_D$ | 34.05 | 34.05 | 30.96 | −14.05 | −14.87 | 1.10 |
| Polar[e] | | | | $\Delta t_R$ (X-$PS_L$) (min)[c] | | |
| $PL_L$ | 48.78 | 51.23 | 47.51 | 0.68 | 1.68 | 4.33 |
| $PA_L$ | 48.25 | 50.57 | 46.63 | 0.15 | 0.80 | 4.15 |
| $PS_L$[f] | 48.10 | 49.99 | 45.83 | 0 | 0 | 3.63 |
| $PV_L$ | 47.83 | 49.93 | 46.18 | −0.27 | 0.35 | 3.91 |
| $PK_L$ | 46.38 | 47.90 | 43.89 | −1.72 | −1.94 | 3.17 |
| PG | 45.86 | 47.09 | 43.07 | −2.24 | −2.76 | 2.82 |
| $PS_D$ | 45.47 | 46.60 | 42.59 | −2.63 | −3.24 | 2.73 |
| $PA_D$ | 45.19 | 46.36 | 42.57 | −2.91 | −3.26 | 2.82 |
| $PL_D$ | 44.73 | 45.85 | 42.14 | −3.37 | −3.69 | 2.82 |
| $PV_D$ | 42.96 | 43.83 | 40.51 | −5.14 | −5.32 | 2.54 |
| $PK_D$ | 42.20 | 42.87 | 39.29 | −5.90 | −6.54 | 2.23 |
| C[g] | 22.74 | — | 18.64 | — | — | — |

[a]Peptides are ordered by relative hydrophobicity to the native L-Val substituted analog on the non-polar face and L-Ser substituted analog on the polar face.
[b]denotes the retention times at 5° C., the maximal retention times and the retention times at 80° C. during the temperature profiling.
[c]denotes the difference of retention time relative to that of the native peptide $V_{681}$ ($NV_L$ for the non-polar face substitutions and $PS_L$ for the polar face substitutions), representing the relative hydrophobicity of the peptide analogs.
[d]$P_A$ denotes the association parameter of each peptide during the RP-HPLC temperature profiling, which is the maximal retention time difference of (($t_R^t$-$t_R^5$) for peptide analogs) − ($t_R^t$-$t_R^5$) for control peptide C) within the temperature range, and ($t_R^t$-$t_R^5$) is the retention time difference of a peptide at a specific temperature (t) compared with that at 5° C.
[e]denotes the amino acid substituted on either the non-polar face (N) or the polar face (P) of the amphipathic native peptide $V_{681}$ (see FIG. 1).
[f]$NV_L$ and $PS_L$ are the same peptide, which is the native peptide $V_{681}$.
[g]Peptide C is a random coil control used to calculate $P_A$ values, see footnote d.

Elution times during RP-HPLC have frequently been utilized as a measure of relative hydrophobicity of peptide analogs (26,31). In the current study, peptide analogs differed only by a single amino acid substitution on either the non-polar face or the polar face of $V_{681}$; thus, the retention time data in Table 5 can be considered to reflect the hydrophobicity difference between peptide analogs. In order to more easily visualize the variation in hydrophobicity of the peptide analogs, the retention time data in Table 5 were normalized relative to that of the native peptide $V_{681}$ at 5° C. and 80° C., respectively. Hydrophobicity relative to the native peptide $V_{681}$ indicates an increase or decrease of the apparent peptide hydrophobicity with the different amino acid substitutions on the polar or non-polar face. Again, from Table 5 and FIG. 5, for non-polar face substituted peptides, there was a wide range of peptide hydrophobicity in the order L-Leu>L-Val>L-Ala>L-Ser>Gly>L-Lys at both 5° C. and 80° C. On both the non-polar and polar faces, the relative hydrophobicities of the D-peptides was always less than their L-diastereomers, indicating the helix-disrupting characteristic of D-amino acids also leads to disruption of the preferred binding domain of the helices. On both non-polar and polar faces, peptides exhibited a greater retention time range at 80° C. than at 5° C., also indicating that, due to the unfolding of the helical structures at 80° C., the side-chain hydrophobicity of the substituted amino acids played a more essential role in determining the overall hydrophobicity of the peptide analogs.

The hydrophobicity/hydrophilicity effects of substitutions on the non-polar face relative to the native peptide $V_{681}$ were large. For example, $NV_Q$ to $NA_L$, to $NS_A$, and to $NK_L$ resulted in decreases in hydrophobicity of −4.45, −8.21 and −12.61 min at 80° C., respectively (Table 5). In fact, the same substitutions, i.e., $PV_L$ to $PA_L$, to $PS_L$, and to $PK_L$, resulted in overall hydrophobicity changes of the peptide by +0.45, −0.35 and −2.29 min at 80° C., respectively. This indicates that the polar face substitutions affected overall hydrophobicity of the peptide in a minor way relative to substitutions on the non-polar face. In fact, the effect was of 10 times less for Ala, >20 times less for Ser and >5 times less for Lys.

Since its introduction, the technique of RP-HPLC temperature profiling has been applied on several types of molecules, including cyclic β-sheet peptides (30), monomeric α-helices and α-helices that dimerize (29), as well as α-helices that dimerize to form coiled-coils (42). Although peptides are eluted from a reversed-phase column mainly by an adsorption/desorption mechanism (43), even a peptide strongly bound to a hydrophobic stationary phase will partition between the matrix and the mobile phase when the acetonitrile content becomes high enough during gradient elution. The proposed mechanism of action for temperature profiling of α-helical peptides in RP-HPLC has been explained in detail by Mant, et al. (29). In summary, the mechanism is based on four assumptions: (i) at low temperature, just as an amphipathic α-helical peptide is able to dimerize in aqueous solution (through its hydrophobic, nonpolar face), it will dimerize in solution during partitioning in reversed-phase chromatography; (ii) at higher temperatures, the monomer-dimer equilibrium favors the monomer as the dimer is disrupted; (iii) at sufficiently high temperatures, only monomer is present in solution; and (iv) peptide is always bound in its monomeric helical form to the hydrophobic stationary phase, i.e., the dimer can only be present in solution and disruption of the dimer is required for rebinding to the RP-HPLC matrix.

It is well accepted that the amphipathicity of antimicrobial peptides is necessary for their mechanism of action, since the positively-charged polar face will help the molecules reach the biomembrane through electrostatic interaction with the negatively-charged head groups of phospholipids, and then the nonpolar face of the peptides will allow insertion into the membrane through hydrophobic interactions, causing increased permeability and loss of barrier function of target cells (6,7). Thus, we believe that peptide self-association (i.e., the ability to dimerize) in aqueous solution is a very important parameter to understand antimicrobial activity. If the self-association ability of a peptide in aqueous media is too strong (forming dimers and burying the non-polar face), it could decrease the ability of the peptide to dissociate and penetrate into the biomembrane and to kill target cells.

FIG. 5 shows the temperature profiling of all L-/D-amino acid substituted peptide analogs during RP-HPLC from 5° C. and 80° C. As mentioned above, the dimerization is temperature-dependent. At low temperatures, peptides exist in a dimer-monomer equilibrium during RP-HPLC partitioning, with the dimeric unbound state favored and dissociation required for rebinding; thus, the retention times are relatively low. With the increase of temperature, equilibrium is shifted toward the monomeric form in solution due to the disruption of the dimer. The higher solution concentration of monomer during partitioning increases the on-rate for the bound state, and the retention time therefore increases. It should be noted that the increased temperature also introduces other general effects on retention time because of lower mobile phase viscosity and a significant increase in mass transfer between the stationary phase and mobile phase. These effects decrease retention time with increasing temperature in a linear fashion, as shown for the random coil control peptide C (FIG. 5). Conversely, for the dimerized peptides, at a given temperature dimers are disrupted and converted to monomers and the retention time reaches the maximal value. Above this critical temperature, one will observe a decrease in retention time with increasing temperature because of the low mobile phase viscosity and increase in mass transfer. In addition, the above described temperature-induced conformational changes, as monitored by CD, may also have an impact by decreasing the retention time with increasing temperature, largely due to the destabilization of peptide α-helical structure and loss of preferred binding domain at high temperatures. To eliminate these general effects during RP-HPLC, the data from FIG. 5 were normalized relative to the temperature profile of the random coil peptide standard C, and normalized to the retention time at 5° C., the latter of which is presented as a dotted line in FIG. 6.

It was observed that the peptide analogs in this study showed dramatic varying dimerization ability in solution (FIG. 6). The maximal values of the change of retention times (($t_R^t$-$t_R^5$ for peptide)−($t_R^t$-$t_R^5$ for C)) in FIG. 6 were defined as the peptide association parameter ($P_A$) to quantify the association ability of peptide analogs in solution (Table 5). As seen from the data in Table 5, peptides with higher relative hydrophobicity generally showed stronger self-association ability in solution. The $P_A$ values of the peptide with non-polar face substitutions were of the same order as their relative hydrophobicity, indicating that the hydrophobicity on the hydrophobic face of the amphipathic helix was essential during dimerization, since the dimers are formed by the binding together of the non-polar faces of two amphipathic molecules. In contrast, the different relationship between $P_A$ and the relative hydrophobicity of the peptides with polar face substitutions demonstrated that the hydrophobicity on the polar face of the helices plays a less important role in peptide association. Generally speaking, the $P_A$ values of L-peptides were significantly greater than those of their D-diastereomers, indicating the importance of helical structure during dimerization (Table 5). In Table 5, in most cases, the peptides with polar face substitutions had greater $P_A$ values than the corresponding peptide analogs with the same amino acid substitutions on the non-polar face. This is exactly what one would expect since polar face substitutions have little effect on the preferred dimerization domain, whereas non-polar face substitutions would dramatically affect the hydrophobicity and dimerization ability of the peptide.

Amphipathicity of the L-amino acid substituted peptides was determined by the calculation of hydrophobic moment (32) using the software package Jemboss version 1.2.1 (33), modified to include the hydrophobicity scale determined in our laboratory (see the Examples section for details) (Table 6). Peptide amphipathicity, for the non-polar face substitutions, was directly correlated with side-chain hydrophobicity of the substituted amino acid residue, i.e., the more hydrophobic the residue the higher the amphipathicity (values of 6.70 and 5.60 for $NL_L$ and $NK_L$, respectively); in contrast, on the polar face, peptide amphipathicity was inversely correlated with side-chain hydrophobicity of the substituted amino acid residue, i.e., the more hydrophobic the residue, the lower the amphipathicity (compare $PK_L$ and $PL_L$ with amphipathicity values of 6.62 and 5.45, respectively, Table 6).

The native sequence, $V_{681}$ was very amphipathic with a value of 6.35. To place this value in perspective, the sequence of $V_{681}$ can be shuffled to obtain an amphipathic value of 0.96 (KHAVIKWSIKSSVKFKISTAFKATTI, SEQ ID NO: 41) or a maximum value of 8.10 for the sequence of HWSKLLKS-FTKALKKFAKAITSVVST (SEQ ID NO:42). The range of amphipathicity values achieved by single substitutions on the polar and non-polar faces varied from a low of 5.45 for $PL_L$ to a high of 6.70 for $NL_L$ (Table 6). Even though single substitutions changed the amphipathicity, all the analogs remained very amphipathic, e.g., even with a lysine substitution on the non-polar face, $NK_L$ has a value of 5.60.

TABLE 6

Amphipathicity of peptide analogs.

| Peptide | Amphipathicity[a] | Peptide | Amphipathicity[a] |
|---|---|---|---|
| $NL_L$ | 6.70 | $PL_L$ | 5.45 |
| $NV_L$[b] | 6.35 | $PV_L$ | 5.82 |
| $NA_L$ | 5.98 | $PA_L$ | 6.21 |
| NG | 5.85 | PG | 6.35 |
| $NS_L$ | 5.85 | $PS_L$[b] | 6.35 |
| $NK_L$ | 5.60 | $PK_L$ | 6.62 |

Amphipathicity was determined by the calculation of hydrophobic moment (31) using hydrophobicity coefficients determined by reversed-phase chromatography (see Materials and Methods for details).
Peptides $NV_L$ and $PS_L$ are the same peptide as $V_{681}$.

Concerning the mechanism of action of antimicrobial peptides, many models have been proposed, among which the "barrel-stave" mechanism and the "carpet" model are two (44). In brief, the "barrel-stave" mechanism describes the formation of transmembrane channels/pores by bundles of amphipathic α-helices, as their hydrophobic surfaces interact with the lipid core of the membrane and the hydrophilic surfaces point inward, producing an aqueous pore (45); in contrast, the "carpet" model was proposed for the first time to describe the mechanism of action of dermaseptin S (46), describing the contact of antimicrobial peptides with the phospholipid head group throughout the entire process of membrane permeation which occurs only if there is a high local concentration of membrane-bound peptide. The major difference between the two mechanisms is, in the carpet model, peptides lie at the interface with their hydrophobic surface interacting with the hydrophobic component of the lipids but are not in the hydrophobic core of the membrane, and neither do they assemble the aqueous pore with their hydrophilic faces. A NMR study has shown that the cyclic β-sheet peptide analog of gramicidin S lays in the interface region parallel with the membrane where its hydrophobic surface interacts with the hydrophobic fatty acyl chains and the positively charged residues can still interact with the negatively charged head groups of the phospholipids (47).

Whichever the mechanism, the prerequisite step is the attraction of the peptide molecule to the membrane, followed by insertion into the bilayer. If peptide molecules self-associate in aqueous solution, peptides with lower self-associating ability in an aqueous medium can more easily penetrate into the lipid membrane. From Table 5 and Table 6, peptides with higher relative hydrophobicity on their non-polar face created higher amphipathicity and generally showed stronger self-associating ability in solution; in contrast, for peptides with polar face substitutions, increasing hydrophobicity lowers amphipathicity yet the peptides still strongly self-associate, which indicates that peptide amphipathicity plays a less important role in peptide self-association when changes in amphipathicity are created on the polar face. In addition, self-associating ability is correlated with the secondary structure of peptides, i.e., in this study, disrupting the peptide helical structure by replacing the L-amino acid with its D-amino acid counterpart decreases the $P_A$ values (Table 4 and Table 5).

The hemolytic activity of the peptides against human erythrocytes was determined as a major measure of peptide toxicity toward higher eukaryotic cells. As mentioned before, the native peptide $V_{681}$ (also named as $NV_Q$ or $PS_L$) had strong hemolytic activity, with a minimal hemolytic concentration (MHC value) of 15.6 μg/ml (Table 7). In this study, due to the alteration of hydrophobicity, amphipathicity and stability, the hemolytic activity of the best variants of peptide $V_{681}$ was significantly decreased to no detectable activity, a >32 fold decrease for $NK_L$ (Table 7).

From Table 7, it is clear that, for the non-polar face substituted peptides, hemolytic activity was correlated with the side-chain hydrophobicity of the substituting amino acid residue, i.e., the more hydrophobic the substituting amino acid, the more hemolytic the peptide, consistent with our previous study on the β-sheet antimicrobial peptide gramicidin S (22). For example, the MHC of peptide $NL_L$ was 7.8 μg/ml; in contrast, the MHC was decreased, parallel with the reduction of hydrophobicity, to an undetectable level for peptide $NK_L$. Peptide hydrophobicity and amphipathicity on the non-polar face were also correlated with peptide self-associating ability, thus peptides with less self-association in benign conditions also exhibited less hemolytic activity against eukaryotic cells. In contrast, for polar face substituted peptides, the relationships between self-association, hydrophobicity/amphipathicity and hemolytic activity were less clear. Of course, the hydrophobic non-polar face remained very similar when L-substitutions were made on the polar face; thus, dimerization and hydrophobicity of the non-polar face would be less affected and hemolytic activity would remain relatively strong.

In addition to hydrophobicity/amphipathicity, peptide helicity seemed to have an additional effect on hemolytic activity. In general, on both the non-polar and polar faces, D-amino acid substituted peptides were less hemolytic than their L-diastereomers. For example, $NA_L$ had a MHC value of 31.2 μg/ml compared to $NA_D$ with a value of 250 μg/ml, an 8-fold decrease in hemolytic activity. Similarly, $PV_L$ had a MHC value of 7.8 μg/ml compared to $PV_D$ with a value of 125 μg/ml, a 16-fold decrease in hemolytic activity (Table 7). This phenomenon generally correlated with peptide self-associating ability, since D-diastereomeric analogs exhibited weaker self-associating ability than L-analogs. Additionally, D-substitutions disrupt helicity which, in turn, disrupts hydrophobicity of the non-polar face. This result was also consistent with the data of Shai and coworkers (23,24), who demonstrated that, through multiple D-amino acid substitutions, the helicity of peptides is substantially reduced leading to decreased hemolytic activity. Thus, peptide structure is important in the cytotoxicity towards mammalian cells although these disturbed helices can still maintain antibacterial activity.

As shown in Table 7, peptide analogs with non-polar face substitutions exhibited a greater range of hemolytic activity (7.8 μg/ml to not detectable) than the polar face substitutions (4 to 125 μg/ml), again indicating that the non-polar face of the helix may play a more essential role during the interaction with the biomembrane of normal cells. As expected, the peptides with the polar face substitutions showed stronger hemolytic activity than the peptides with the same amino acid substitutions on the non-polar face, which may be attributed to the different magnitude of the hydrophobicity change by the same amino acid substitutions on different sides of the amphipathic helix. Interestingly, in this study, all polar face substituted peptides except $PL_D$, $PV_D$ and $PK_D$ showed stronger hemolysis of erythrocytes than $V_{681}$; in contrast, on the non-polar face, only peptides $NL_D$ and $NL_L$ were more hemolytic than $V_{681}$.

The antimicrobial activity of the peptides with either non-polar face or polar face amino acid substitutions against a range of gram-negative microorganisms is shown in Table 7. The geometric mean MIC values from 6 microbial strains in this table were calculated to provide an overall evaluation of antimicrobial activity against gram-negative bacteria. It is apparent that many peptide analogs showed considerable improvement in antimicrobial activity against gram-negative bacteria over the native peptide $V_{681}$, e.g., peptides $NK_L$ and $PK_D$ exhibited 2.8-fold and 3.4-fold improvement on the average MIC value compared to $V_{681}$, respectively (geometric mean comparison; Table 7). Generally, the peptide analogs have high activity against bacterial strains of *E. coli* (UB 1005 wt and DC2 abs), *S. typhimurium* C610 abs and *P. aeruginosa* H187 wt in this study (Table 7).

For gram-negative bacteria, disruption of peptide helicity out weighted other factors in the improvement of antimicrobial activity; i.e., in most cases, the peptides with D-amino acid substitutions showed better antimicrobial activity than L-diastereomers. The exceptions were peptides $NS_D$ and $NK_D$. The reason for the low activity of peptides $NS_D$ and $NK_D$ was possibly the combined effects of the destabilization of the helix, the decrease of hydrophobicity on the non-polar face and the disruption of amphipathicity, highlighting the importance of maintaining a certain magnitude of hydrophobicity and amphipathicity on the non-polar face of the helix for biological activity, i.e., perhaps there is a combined threshold of helicity and hydrophobicity/amphipathicity required for biological activity of α-helical antimicrobial peptides. In this study, peptide self-associating ability (relative hydrophobicity) seemed to have no general relationship to MIC; however, interestingly, for peptides with L-hydrophobic amino acid substitutions (Leu, Val and Ala) in the polar and non-polar faces, the less hydrophobic the substituting amino acid, the more active the peptide against gram-negative bacteria.

Table 8 shows the antimicrobial activity of the peptides against gram-positive microorganisms. By introducing D-/L-amino acid substitutions, we improved the antimicrobial activity of peptide $V_{681}$ against gram-positive bacteria by as much as 2.7-fold (geometric mean MIC values for $V_{681}$ were 6.3 µg/ml compared to 2.3 µg/ml for $PS_D$, Table 8). Compared with peptide $V_{681}$, most of the peptide analogs with increased antimicrobial activity against gram-positive microorganisms were D-amino acid substituted peptides (6 D-peptides versus 1 L-peptide). It was surprising to observe that peptides with polar face substitutions showed an overall greater improvement in MIC than those with non-polar face substitutions. Generally speaking, increasing the hydrophobicity of the native peptide $V_{681}$ by amino acid substitutions at either the polar or the non-polar face decreased the antimicrobial activity against Gram-positive bacteria, e.g., peptides $NL_L$, $PL_L$, $PV_L$ and $PA_L$ (Table 8). Amino acid substitutions of D-Ser and D-Lys on the non-polar face significantly weakened the activity, in a similar manner to the anti-Gram-negative activity, indicating again the importance of maintaining a certain magnitude of helicity, hydrophobicity/amphipathicity on the non-polar face of the helix for peptide Gram-positive antimicrobial activity.

Therapeutic index is a widely employed parameter to represent the specificity of antimicrobial reagents. It is calculated by the ratio of MHC (hemolytic activity) and MIC (antimicrobial activity); thus, larger values in therapeutic index indicate greater antimicrobial specificity. As mentioned above, the native peptide $V_{681}$ is a peptide with good antimicrobial activity coupled with strong hemolytic activity; hence, its therapeutic index is low (1.8 and 2.5 for gram-negative and gram-positive bacteria, respectively) and comparable to general toxins like melittin. In this study, by altering peptide hydrophobicity/hydrophilicity, amphipathicity and helicity, we significantly increased the therapeutic index of peptide $V_{681}$ against gram-negative bacteria by 90-fold (Table 7) and Gram-positive bacteria by 23-fold (Table 8). As indicated in Tables 7 and 8, there was a greater range of therapeutic indices for peptides with the non-polar face substitutions compared with the polar face substitutions, which was consistent with peptide self-association studies, indicating that the non-polar face of the helix may play a more important role in the mechanism of action.

Table 9 summarizes the data for these peptide analogs with improved therapeutic index values relative to the native peptide $V_{681}$. From Table 3 and Table 9, it is clear that all peptides with improved therapeutic indices are those showing less stable helical structure in benign medium (either the D-amino acid substituted peptides or the hydrophilic amino acid substituted peptides on the non-polar face). The peptide with the best therapeutic index among all the analogs is $NK_L$ with a 90-fold improvement compared with $V_{681}$ against Gram-negative bacteria; in contrast, peptide $NA_D$ is the analog with the broadest specificity against all the tested gram-negative and gram-positive microorganisms, having a 42-fold improvement in therapeutic index against gram-negative bacteria and a 23-fold improvement against gram-positive bacteria. It is noteworthy that the hemolytic activity of these two peptides was extremely weak; in addition, peptides $NK_L$ and $NA_D$ exhibited improved antimicrobial activity compared to peptide $V_{681}$ against gram-negative bacteria and identical antimicrobial activity against gram-positive bacteria.

In order to evaluate the biological activities of the D-enantiomeric peptides, namely $D-NA_L$ and $D-NK_D$, the hemolytic activity of the peptides against human erythrocytes was determined as the maximal peptide concentration that produces no hemolysis after 18 hours of incubation at 37° C. The parent peptide, $V_{681}$, exhibited the strongest hemolytic activity with a value of 7.8 µg/ml, compared to peptides $NK_L$ and $NA_D$ (250.0 µg/ml and 31.3 µg/ml, respectively) (Table 10). The activity of the D-enantiomers was quantitatively equivalent to that of L-enantiomers.

Figure 9:
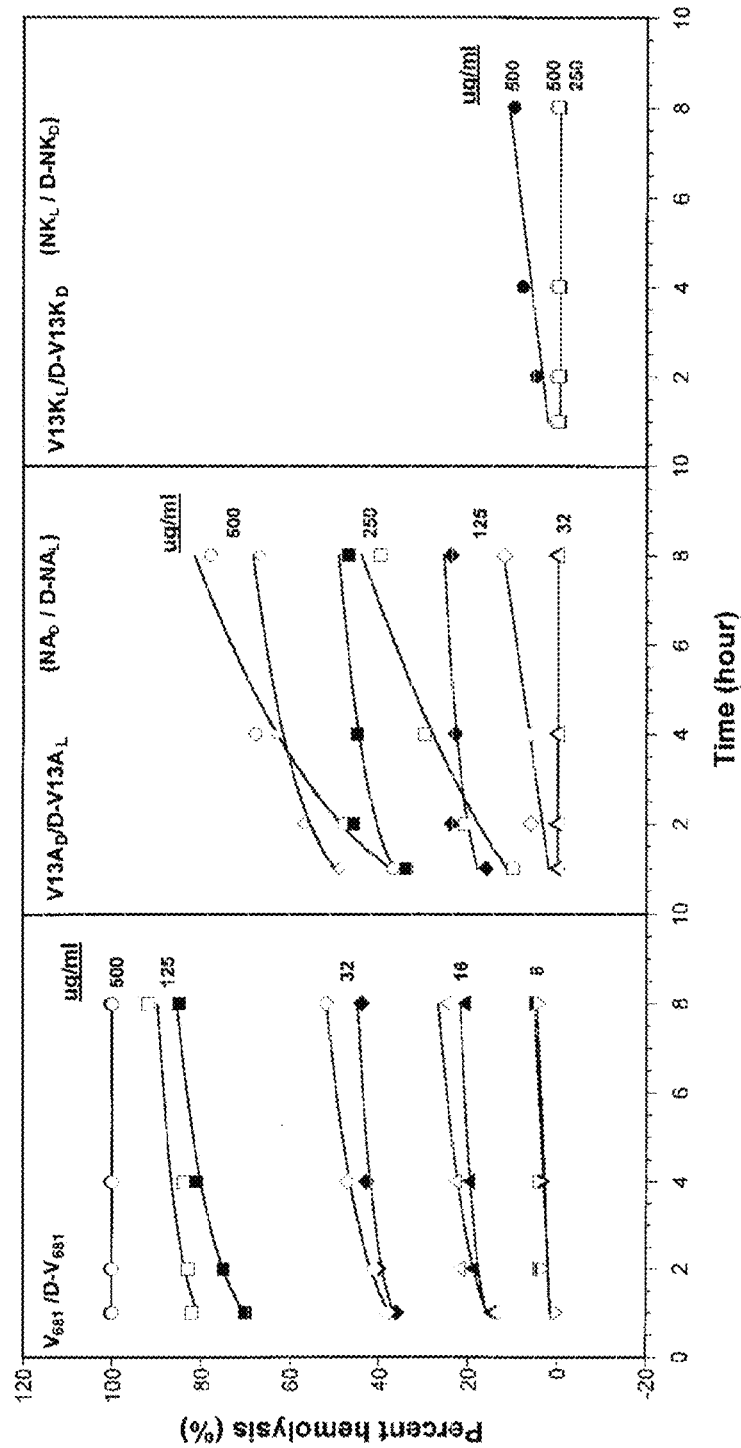
FIG. 9 shows the results of peptide hemolysis of human red blood cells. Closed symbols were used for L-peptides and open symbols were used for D-peptides. Different symbols were used to represent the different concentrations of peptides in the hemolysis study.

In the studies described above (see Tables 5-7), the hemolytic activities of peptides V681, $NA_D$ and $NK_L$ were determined as 15.6 µg/ml, 250.0 µg/ml and greater than 250.0 µg/ml, respectively, following incubation for 12 hours at 37° C. instead of the 18 hours incubation used for the D-enantiomers. Hence, a hemolysis time study was carried out to investigate the extent of hemolysis during different periods of incubation and different peptide concentrations in order to explore the relationship between hemolysis and incubation time. As shown in FIG. 9, a hemolysis time study was carried out over 8 hours at peptide concentrations of 8, 16, 32, 64, 125, 250 and 500 µg/ml. The percent hemolysis of cells was determined spectrophotometrically by comparison with the complete hemolysis of cells in water. From FIG. 9, peptides $V_{681}$, $D-V_{681}$, $NA_D$ and $D-NA_L$ exhibited an increase in erythrocyte hemolysis with increasing incubation time at most peptide concentrations. Significantly, peptides $NK_L$ and $D-NK_D$ showed negligible (less than 10%) or no hemolysis against human red blood cells after 8 hours even at the extremely high peptide concentration of 500 µg/ml. From FIG. 9, it is clear that the enantiomeric peptide pair $V_{681}/D-V_{681}$ exhibit cell lysis to a significantly greater extent than the $NA_D/D-NA_L$ peptide pair. Thus, 100% hemolysis was already apparent after just 1 hour incubation for $V_{681}$ and $D-V_{681}$ at a peptide concentration of 500 µg/ml, whilst this value was approximately 40% for peptides $NA_D$ and $D-NA_L$. In addition, while a small increase in hemolysis was apparent for $V_{681}$ and $D-V_{681}$ at a peptide concentration of just 8 µg/ml, negligible hemolysis was seen for $NA_D$ and $D-NA_L$ at a peptide concentration of 32 µg/ml. It is interesting to note that for our lead compounds, peptides $NA_D$/D-$NA_L$ and $NK_L$/D-$NK_D$, D-enantiomers generally exhibited slightly weaker hemolytic activity compared to L-enantiomers at most peptide concentrations, the only exception being $NA_D$ and D-$NA_L$ at 500 µg/ml, where the activity of the L-peptide is greater at less than 4 hours incubation but weaker from 4 hours onwards.

*Pseudomonas aeruginosa* strains used in this study are a diverse group of clinical isolates from different places in the world. Antibiotic susceptibility tests show that these *Pseudomonas aeruginosa* strains share similar susceptibility to most antibiotics except that there is about a 64-fold difference for the range of ciprofloxacin susceptibility (Vasil, M. L. et al unpublished data). Antimicrobial activities of peptide enantiomers against *Pseudomonas aeruginosa* strains are shown in Table 10. In general, the antimicrobial activity of L- and D-enantiomers against *Pseudomonas aeruginosa* varied within 4-fold. CP204, a *Pseudomonas aeruginosa* strain from cystic fibrosis patients, is apparently the most susceptible strain to these peptides with MIC values from 7.8 to 31.3 µg/ml. The geometric mean MIC values from six *Pseudomonas aeruginosa* strains were calculated to provide an overall evaluation of antimicrobial activity of these peptides against *Pseudomonas aeruginosa*. Fold improvement was calculated by comparing the geometric mean MIC value of each peptide to that of the parent peptide $V_{681}$. It is clear that, in most cases, all-D-peptides exhibited slightly better antimicrobial activity than their L-enantiomers.

The therapeutic indices of the peptides against *Pseudomonas aeruginosa* are shown in Table 10. By replacing L-valine with D-alanine or L-lysine, we significantly increased the therapeutic index against *Pseudomonas aeruginosa* strains by 4.7 fold (peptide $NA_D$) and 16.7 fold (peptide $NK_L$). In addition, by making enantiomeric D-peptides, we further improved the therapeutic index against *Pseudomonas aeruginosa* by 7.3 fold (peptide D-$NA_L$) and 26.7 fold (peptide D-$NK_D$) as measured by the standard microtiter dilution method. Peptide D-$NK_D$ showed no hemolysis at 500 µg/ml after 8 hours in our time study (FIG. 9) which is a more stringent test of hemolytic activity. The hemolytic activities of $V_{681}$ were not different when determined by the standard microtiter dilution method at 18 hours or by the time study at 8 hours using a peptide concentration of 500 µg/ml (Table 10 and FIG. 9). Thus, using a peptide concentration of 500 µg/ml, the MHC value of D-$NK_D$ increased the fold improvement of the therapeutic index compared to $V_{681}$ to 53-fold. Our overall conclusion is that the key differences in biological activities lie in the much more dramatic variations in hemolytic activity (MHC values) since the differences in antimicrobial activity between the six peptides are relatively minor (Table 10). Thus, the dramatic increases in therapeutic indices arise from the difference in hemolytic activity.

Table 11 shows peptide antimicrobial activity and therapeutic indices against six different Gram-negative bacterium strains. It is clear to see that, in general, all-L-peptides have equivalent antimicrobial activity against Gram-negative bacteria compared to their D-enantiomers, since MIC values of L- and D-enantiomers are all within a 2-fold difference. In Table 11, geometric mean MIC was calculated to provide an overall view of antimicrobial activity of the peptides against Gram-negative bacteria and was also used to calculate the therapeutic index. Peptides $NK_L$ and D-$NK_D$ both show a 40-fold improvement in therapeutic index against Gram-negative bacteria compared to peptide $V_{681}$ as measured by the standard microtiter dilution method. For this improvement in the therapeutic index of peptides against Gram-negative bacteria, peptide hemolytic activity is again the key factor. Using our most stringent test of hemolytic activity, the MHC value of 500 µg/ml for peptide D-$NK_D$ showed no hemolysis after 8 hours in our time study (FIG. 9) and the fold improvement of the therapeutic index compared to V681 was 80-fold.

The antimicrobial activity against Gram-positive bacteria and a fungus of L- and D-enantiomeric peptides is compared in Table 12. It is clear that our peptides were effective in killing the Gram-positive bacteria tested. The least sensitive Gram-positive bacterium to the enantiomeric peptides was *E. faecalis*. The effectiveness of the peptides to lyse cells of the fungus *C. albicans* was similar to *E. faecalis*. For Gram-positive bacteria and the fungus, D-peptides again generally showed the same or better antimicrobial activity than L-enantiomers. Although the geometric mean MIC values of peptides $NK_L$/D-$NK_D$ were among the two lowest, due to the high MHC values (poor or no hemolytic activity), the therapeutic indices of $NK_L$ and D-$NK_D$ were the highest against Gram-positive bacteria and the fungus. Similar to that seen against Gram-negative bacteria, the therapeutic index of peptide D-$NK_D$ was increased 34.7-fold and 16.7-fold against Gram-positive bacteria and *C. albicans*, respectively, due to the poor or no hemolytic activity as measured by the standard microtiter dilution method. Using our most stringent test of hemolytic activity, the MHC value of 500 µg/ml for peptide D-$NK_D$ showed no hemolysis after 8 hours in our time study (FIG. 9) and the fold improvement of the therapeutic indices compared to $V_{681}$ were 69- and 33-fold against Gram-negative bacteria and fungus, respectively.

TABLE 7

Antimicrobial (MIC) and hemolytic (MHC) activities of peptide analogs against gram-negative bacteria and human red blood cells.

| | MIC[a] (µg/ml) | | | | | | | MHC[c] (µg/ml) | |
|---|---|---|---|---|---|---|---|---|---|
| Peptides | E. coli UB1005 wt[e] | E. coli DC2 abs[e] | S. typhimurium C587 wt[e] | S. typhimurium C610 abs[e] | P. aeruginosa H187 wt[e] | P. aeruginosa H188 abs[e] | GM[b] | hRBC | Therapeutic index[d] |
| $NL_L$ | 6.4 | 5.0 | 32.0 | 10.1 | 12.7 | 32.0 | 12.7 | 7.8 | 0.6 |
| $NV_L$[f] | 7.1 | 4.5 | 20.2 | 5.7 | 6.4 | 20.2 | 8.8 | 15.6 | 1.8 |
| $NA_L$ | 2.5 | 2.5 | 6.4 | 2.5 | 5.0 | 6.4 | 3.8 | 31.2 | 8.1 |
| NG | 2.5 | 2.5 | 5.0 | 2.5 | 6.4 | 10.1 | 4.1 | 125.0 | 30.2 |
| $NS_L$ | 2.5 | 2.5 | 6.4 | 2.0 | 6.4 | 10.1 | 4.2 | 125.0 | 30.1 |
| $NK_L$[g] | 2.5 | 1.6 | 4.0 | 1.3 | 8.0 | 5.0 | 3.1 | >250.0 | 163.0 |
| $NL_D$ | 3.2 | 2.5 | 16.0 | 3.2 | 6.4 | 10.1 | 5.5 | 7.8 | 1.4 |
| $NV_D$ | 2.5 | 1.6 | 5.0 | 2.0 | 4.0 | 8.0 | 3.3 | 62.5 | 19.0 |
| $NA_D$[g] | 1.6 | 2.0 | 5.0 | 2.0 | 4.0 | 10.1 | 3.3 | 250.0 | 75.7 |
| $NS_D$ | 3.2 | 2.0 | 12.7 | 2.0 | 18.3 | 20.2 | 6.3 | >250.0 | 79.9 |
| $NK_D$ | 3.2 | 2.5 | 32.0 | 1.0 | 32.0 | 25.4 | 7.7 | >250.0 | 65.0 |

TABLE 7-continued

Antimicrobial (MIC) and hemolytic (MHC) activities of peptide analogs against gram-negative bacteria and human red blood cells.

| Peptides | | | | | | | | | |
|---|---|---|---|---|---|---|---|---|---|
| $PL_L$ | 16.0 | 5.0 | 32.0 | 12.7 | 20.2 | 32.0 | 16.6 | 4.0 | 0.2 |
| $PV_L$ | 6.4 | 4.0 | 32.0 | 5.0 | 10.1 | 20.2 | 9.7 | 7.8 | 0.8 |
| $PA_L$ | 6.4 | 4.0 | 20.2 | 4.0 | 10.1 | 16.0 | 8.3 | 15.6 | 1.9 |
| PG | 5.0 | 2.5 | 12.7 | 3.2 | 4.0 | 10.1 | 5.2 | 7.8 | 1.5 |
| $PS_L{}^f$ | 7.1 | 4.5 | 20.2 | 5.7 | 6.4 | 20.2 | 8.8 | 15.6 | 1.8 |
| $PK_L$ | 10.1 | 4.0 | 25.4 | 8.0 | 25.4 | 32.0 | 13.7 | 4.0 | 0.3 |
| $PL_D$ | 5.0 | 2.5 | 10.1 | 3.2 | 4.0 | 10.1 | 5.0 | 31.2 | 6.2 |
| $PV_D$ | 5.0 | 2.5 | 10.1 | 4.0 | 6.4 | 16.0 | 6.1 | 125.0 | 20.5 |
| $PA_D$ | 4.0 | 2.5 | 8.0 | 2.0 | 5.0 | 8.0 | 4.3 | 15.6 | 3.6 |
| $PS_D$ | 2.5 | 1.6 | 5.0 | 1.6 | 2.0 | 10.1 | 2.9 | 15.6 | 5.3 |
| $PK_D$ | 3.2 | 1.6 | 3.2 | 1.6 | 2.0 | 6.4 | 2.6 | 31.2 | 11.8 |

[a] Antimicrobial activity (minimal inhibitory concentration) is given as the geometric mean of three sets of determinations.

[b] GM denotes the geometric mean of MIC values from all 6 microbial strains in this table.

[c] Hemolytic activity (minimal hemolytic concentration) was determined on human red blood cells (hRBC). When no detectable hemolytic activity was observed at 250.0 μg/ml, a value of 500 μg/ml was used for calculation of the therapeutic index.

[d] Therapeutic index = MHC (μg/ml)/geometric mean of MIC (μg/ml). Larger values indicate greater antimicrobial specificity.

[e] wt denotes the wild type strain and abs denotes the antibiotics sensitive strain.

[f] $NV_L$ and $PS_L$ are the same peptide, which is the native peptide $V_{681}$.

[g] The boxed results show the two best peptides with broad spectrum activity in terms of the therapeutic index against both Gram-negative and Gram-positive bacteria.

TABLE 8

Antimicrobial (MIC) and hemolytic (MHC) activities of peptide analogs against gram-positive bacteria and human red blood cells.

| Peptides | MIC$^a$ (μg/ml) | | | | | | | MHC$^c$ (μg/ml) hRBC | Therapeutic index$^d$ |
|---|---|---|---|---|---|---|---|---|---|
| | S. aureus 25923 wt$^e$ | S. aureus SAP0017 methR$^e$ | S. epidermidis C621 wt$^e$ | B. subtilis C971 wt$^e$ | E. faecalis C625 wt$^e$ | C. xerosis C875 wt$^e$ | GM$^b$ | | |
| $NL_L$ | 32.0 | 25.4 | 8.0 | 3.2 | 32.0 | 2.5 | 10.9 | 7.8 | 0.7 |
| $NV_L{}^f$ | 16.0 | 9.0 | 5.0 | 2.2 | 16.0 | 2.5 | 6.3 | 15.6 | 2.5 |
| $NA_L$ | 8.0 | 5.0 | 3.2 | 2.0 | 16.0 | 2.0 | 4.5 | 31.2 | 6.9 |
| NG | 25.4 | 10.1 | 3.2 | 2.0 | 50.8 | 2.0 | 7.4 | 125.0 | 16.8 |
| $NS_L$ | 16.0 | 12.7 | 4.0 | 2.5 | 50.8 | 1.6 | 7.4 | 125.0 | 16.9 |
| $NK_L{}^g$ | 64.0 | 64.0 | 5.0 | 1.6 | 64.0 | 1.3 | 11.8 | >250.0 | 42.3 |
| $NL_D$ | 5.0 | 4.0 | 2.5 | 2.5 | 6.4 | 1.6 | 3.3 | 7.8 | 2.4 |
| $NV_D$ | 4.0 | 3.2 | 1.6 | 1.3 | 12.7 | 1.3 | 2.8 | 62.5 | 22.7 |
| $NA_D{}^g$ | 8.0 | 5.0 | 2.0 | 1.6 | 32.0 | 1.6 | 4.3 | 250.0 | 57.8 |
| $NS_D$ | 64.0 | 64.0 | 12.7 | 2.5 | 64.0 | 2.0 | 16.0 | >250.0 | 31.3 |
| $NK_D$ | 64.0 | 64.0 | 25.4 | 3.2 | 64.0 | 2.0 | 18.7 | >250.0 | 26.8 |
| $PL_L$ | 32.0 | 32.0 | 16.0 | 5.0 | 50.8 | 2.5 | 14.8 | 4.0 | 0.3 |
| $PV_L$ | 16.0 | 12.7 | 8.0 | 2.5 | 20.2 | 1.3 | 6.9 | 7.8 | 1.1 |
| $PA_L$ | 16.0 | 12.7 | 4.0 | 2.5 | 20.2 | 2.0 | 6.6 | 15.6 | 2.4 |
| PG | 8.0 | 5.0 | 4.0 | 2.0 | 12.7 | 2.0 | 4.5 | 7.8 | 1.7 |
| $PS_L{}^f$ | 16.0 | 9.0 | 5.0 | 2.2 | 16.0 | 2.5 | 6.3 | 15.6 | 2.5 |
| $PK_L$ | 32.0 | 16.0 | 6.4 | 3.2 | 32.0 | 4.0 | 10.5 | 4.0 | 0.4 |
| $PL_D$ | 8.0 | 5.0 | 4.0 | 2.0 | 16.0 | 2.0 | 4.7 | 31.2 | 6.7 |
| $PV_D$ | 16.0 | 8.0 | 4.0 | 2.5 | 32.0 | 2.0 | 6.6 | 125.0 | 19.0 |
| $PA_D$ | 6.4 | 5.0 | 2.5 | 2.0 | 12.7 | 1.6 | 3.9 | 15.6 | 4.1 |
| $PS_D$ | 4.0 | 2.5 | 2.0 | 1.3 | 6.4 | 1.0 | 2.3 | 15.6 | 6.7 |
| $PK_D$ | 4.0 | 2.5 | 2.0 | 2.0 | 12.7 | 1.0 | 2.8 | 31.2 | 11.0 |

[a] Antimicrobial activity (minimal inhibitory concentration) is given as the geometric mean of three sets of determinations.

[b] GM denotes the geometric mean of MIC values from all 6 microbial strains in this table.

[c] Hemolytic activity (minimal hemolytic concentration) was determined on human red blood cells (hRBC). When no detectable hemolytic activity was observed at 250.0 μg/ml, a value of 500 μg/ml was used for calculation of the therapeutic index.

[d] Therapeutic index = MHC (μg/ml)/geometric mean of MIC (μg/ml). Larger values indicate greater antimicrobial specificity.

[e] wt denotes the wild type strain and methR denotes the methicillin-resistant strain.

[f] $NV_L$ and $PS_L$ are the same peptide, which is the native peptide $V_{681}$.

[g] The boxed results show the two best peptides with broad spectrum activity in terms of the therapeutic index against both Gram-negative and Gram-positive bacteria.

TABLE 9

Effect of amino acid substitutions on the biological activity of $V_{681}{}^{a}$.

| | Gram-negative | | | | $M

TABLE 11-continued

Antimicrobial (MIC) and hemolytic (MHC) activities of peptide analogs against Gram-negative bacteria and human red blood cells.

| | | | | MHC[b] (μg/ml) | | | | | | Therapeutic index[f] | |
|---|---|---|---|---|---|---|---|---|---|---|---|
| | MHC[a] (μg/ml) | E. coli C498 | E. coli C500 | St C587 | St C610 | Pa H187 | Pa H188 | | | | |
| Peptides | hRBC | wt[c] | abs[c] | wt[c] | abs[c] | wt[c] | abs[c] | GM[d] | Fold[e] | MHC/MIC | Fold[g] |
| NK$_L$ | 250.0 | 3.1 | 3.1 | 6.3 | 3.1 | 6.3 | 3.1 | 3.9 | 1.3 | 64.1 | 40.1 |
| D-NK$_D$ | 250.0[h] | 3.1 | 3.1 | 6.3 | 3.1 | 6.3 | 3.1 | 3.9 | 1.3 | 64.1 | 40.1 (80.2)[h] |

[a]Hemolytic activity (maximal peptide concentration with no hemolysis after 18 hours) was determined on human red blood cells (hRBC).
[b]Antimicrobial activity (minimal inhibitory concentration) is from three sets of determinations.
[c]E. coli denotes *Escherichia coli*, St denotes *Salmonella typhimurium*, Pa denotes *Pseudomonas aeruginosa*, wt denotes the wild-type lab strain and abs denotes an antibiotic sensitive strain.
[d]GM denotes the geometric mean of MIC values from all 6 microbial strains in this table.
[e]Denotes fold improvement in the geometric mean of MIC compared to parent peptide V$_{681}$.
[f]Therapeutic index = MHC (μg/ml)/geometric mean of MIC (μg/ml). Larger values indicate greater antimicrobial specificity.
[g]Denotes fold improvement in the therapeutic index compared to parent peptide V$_{681}$.
[h]In the hemolysis time study, D-V13K$_D$ showed no hemolysis at 500 μg/ml at 8 hours which would increase the fold improvement in the therapeutic index to 80.2 fold.

TABLE 12

Antimicrobial (MIC) and hemolytic (MHC) activities of peptide analogs against Gram-positive bacteria, fungus and human red blood cells.

| | | | | MIC[b] (μg/ml) | | | | | | Therapeutic index[e] | | MIC[b] | Therapeutic index[f] | |
|---|---|---|---|---|---|---|---|---|---|---|---|---|---|---|
| | MHC[a] | S. aureus 622 | S. aureus 623 | S. epidermidis C621 | B. subtilis C971 | E. faecalis C625 | C. xerosis C875 | | | | | | | |
| Peptides | (μg/ml) hRBC | wt[c] | methR[c] | wt[c] | wt[c] | wt[c] | wt[c] | GM[d] | Fold[d] | MHC/ MIC | Fold[g] | (μg/ml) C. albicans | MHC/ MIC | Fold[g] |
| V$_{681}$ | 7.8 | 3.1 | 6.3 | 6.3 | 3.1 | 6.3 | 3.1 | 4.4 | 1.0 | 1.8 | 1.0 | 12.5 | 0.6 | 1.0 |
| D-V$_{681}$ | 7.8 | 6.3 | 6.3 | 1.6 | 1.6 | 6.3 | 3.1 | 3.5 | 1.3 | 2.2 | 1.2 | 6.3 | 1.2 | 2.0 |
| NA$_D$ | 31.3 | 1.6 | 3.1 | 1.6 | 3.1 | 12.5 | 1.6 | 2.8 | 1.6 | 11.2 | 6.2 | 12.5 | 2.5 | 4.2 |
| D-NA$_L$ | 31.3 | 3.1 | 3.1 | 1.6 | 1.6 | 12.5 | 1.6 | 2.8 | 1.6 | 11.2 | 6.2 | 12.5 | 2.5 | 4.2 |
| NK$_L$ | 250.0 | 12.5 | 12.5 | 6.3 | 3.1 | 50.0 | 1.6 | 7.9 | 0.6 | 31.6 | 17.6 | 50.0 | 5.0 | 8.3 |
| D-NK$_D$ | 250.0[h] | 6.3 | 6.3 | 3.1 | 1.6 | 12.5 | 1.6 | 4.0 | 1.1 | 62.5 | 34.7 (69.4)[h] | 25.0 | 10.0 | 16.7 (33.4)[h] |

[a]Hemolytic activity (maximal peptide concentration with no hemolysis after 18 hours) was determined on human red blood cells (hRBC).
[b]Antimicrobial and antifungal activities (minimal inhibitory concentration) are from three sets of determinations.
[c]S. aureus denotes *Staphylococcus aureus*, S. epidermidis denotes *Staphylococcus epidermidis*, B. subtilis denotes *Bacillus subtilis*, E. faecalis denotes *Enterococcus faecalis*, C. xerosis denotes *Corynebacterium xerosis*, C. albicans denotes *Candida albicans*, wt denotes the wild type strain and methR denotes the methicillin-resistant clinical strain.
[d]GM denotes the geometric mean of MIC values from all 6 gram-positive microbial strains in this table. Fold denotes fold improvement in the geometric mean MIC compared to parent peptide V$_{681}$.
[e]Therapeutic index = MHC (μg/ml)/geometric mean MIC (μg/ml). Larger values indicate greater antimicrobial specificity.
[f]Denotes the therapeutic index of the peptides against a fungus C. albicans.
[g]Denotes fold improvement in the therapeutic index compared to parent peptide V$_{681}$.
[h]In the hemolysis time study, D-V13K$_D$ showed no hemolysis at 500 μg/ml at 8 hours which would increase the fold improvement in the therapeutic index to 69.4 fold and 33.4 fold for Gram-positive bacteria and C. albicans, respectively.

Figure 10:
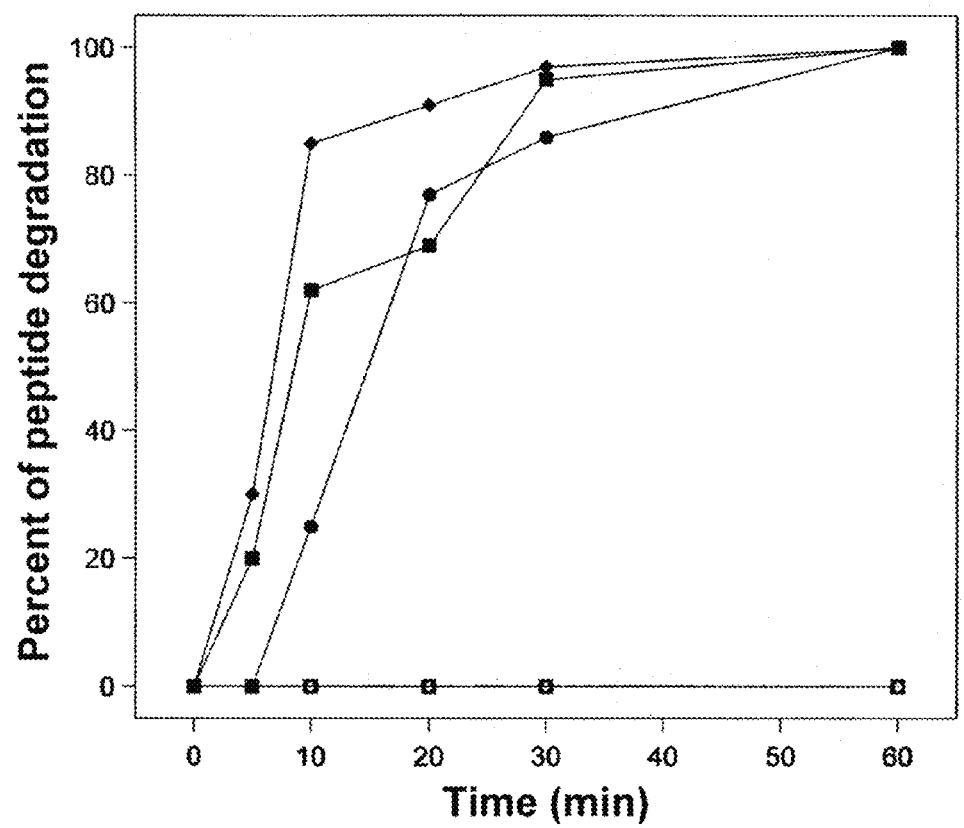
FIG. 10 illustrates the peptide stability to proteolysis by trypsin. Closed symbols were used for L-peptides and open symbols were used for D-peptides. Circles denote $V_{681}$ and D-$V_{681}$, squares denote $NK_L$ and D-$NK_D$, and diamonds denote $NA_D$ and D-$NA_L$.
Figure 11:
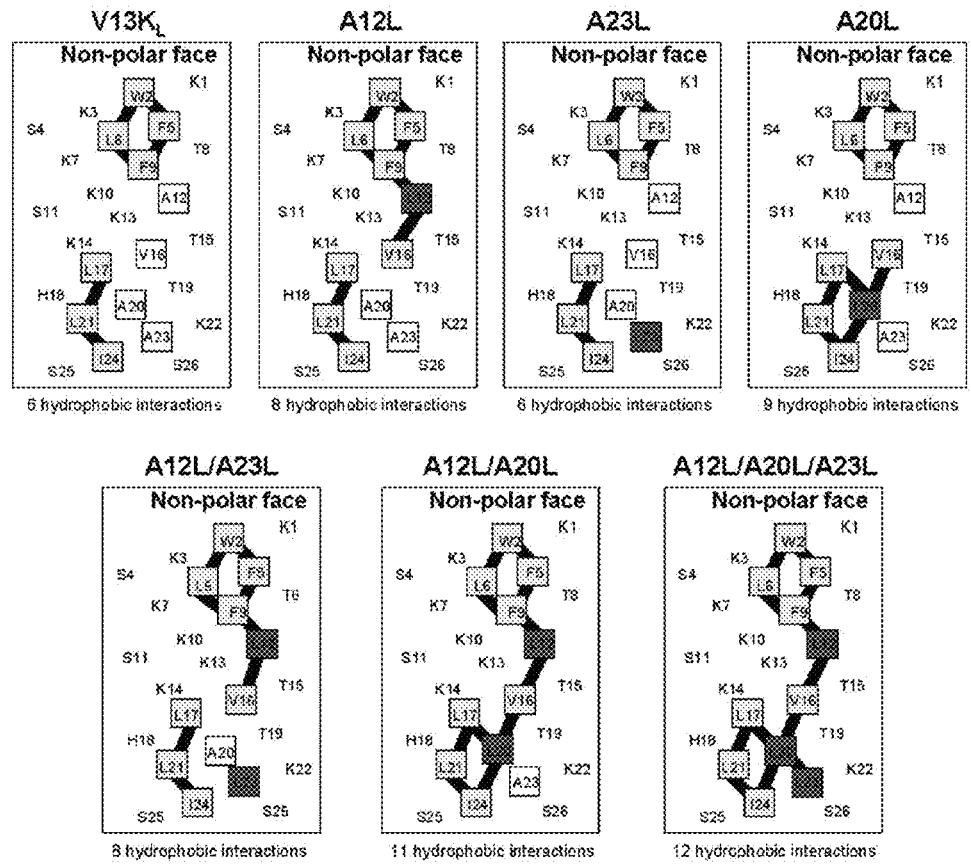
FIG. 11 is a representation of the parent peptide $NK_L$ and analogs (with different leucine substitutions) as helical nets showing the non-polar faces. The hydrophobic amino acid residues on the non-polar faces are boxed. The substituting leucine residues are colored red and the amino acid residues involved in the i→i+3 and i→i+4 hydrophobic interactions are colored yellow. The i→i+3 and i→i+4 hydrophobic interactions are shown as black bars and the numbers of hydrophobic interactions on the non-polar face are indicated. One-letter code is used for the amino acid residues.

FIG. 10 illustrates the stability of L- and D-enantiomeric peptides in the presence of trypsin at a molar ratio of 20,000:1 or 20 mM:1 μM (peptide:trypsin) at 37° C. The assay was carried out for 8 hours; however, only the stability of the peptides in the first 60 minutes is shown in FIG. 10, due to the reason that all three L-peptides were 100% digested by trypsin after 1 hour of incubation at 37° C. It is interesting to see that peptide V$_{681}$ showed a slightly more resistance against trypsin than NK$_L$ and NA$_D$; in contrast, NK$_L$ and NA$_D$ generally showed a similar trend of degradation in the presence of trypsin. All three peptides were 86-97% digested after 30 minutes. In sharp contrast, D-peptides were completely stable (no degradation) to trypsin even at a 10-fold higher molar concentration ratio of trypsin versus peptide (2 mM peptide:1 μM trypsin) for 8 hours.

As mentioned previously, the "barrel-stave" and the "carpet" mechanisms are the two main theories used to explain the mechanism of action of antimicrobial peptides. However, neither mechanism alone can fully explain the data in this study. For example, the hemolytic activity is correlated to the peptide hydrophobicity and amphipathicity on the non-polar face, which may be consistent with the "barrel-stave" mechanism, i.e., peptides interact with the hydrophobic core of the membrane by their non-polar face to form pores/channels. In contrast, the antimicrobial activity is not correlated with peptide hydrophobicity/amphipathicity, showing that the "barrel-stave" mechanism may not be suitable to explain the mechanism of antimicrobial action. Indeed, the "carpet" mechanism may best explain the interaction between the peptides and the bacterial membrane. Based on the above observations, we propose that both mechanisms are in operation for the peptides used in this study, i.e., the mechanism depends upon the difference in membrane composition between prokaryotic and eukaryotic cells. If the peptides form pores/channels in the hydrophobic core of the eukaryotic bilayer, they would cause the hemolysis of human red blood cells; in contrast, for prokaryotic cells, the peptides lyse cells in a detergent-like mechanism as described in the "carpet" mechanism.

Indeed, it is believed that the extent of interaction between peptide and biomembrane is dependent on the composition of lipid bilayer. For example, Liu, et al. (48-50) utilized a polyleucine-based α-helical transmembrane peptide to demonstrate that the peptide reduced the phase transition temperature to a greater extent in phosphatidylethanolamine (PE) bilayers than in phosphatidylcholine (PC) or phosphatidylglycerol (PG) bilayers, indicating a greater disruption of PE organization. The zwitterionic PE is the major lipid component in prokaryotic cell membranes and PC is the major lipid component in eukaryotic cell membranes (51,52). In addition, although PE also exists in eukaryotic membranes, due to the asymmetry in lipid distribution, PE is mainly found in the inner leaflet of the bilayer while PC is mainly found in the outer leaflet of the eukaryotic bilayer. We draw the conclusion that the antimicrobial specificity of the antimicrobial α-helical peptides is a result of the composition differences of the lipid bilayer between eukaryotic and bacterial cells.

In support of this proposal, we have selected two examples from our study. The results for peptide $NK_L$, the peptide with the highest therapeutic index against Gram-negative bacteria, can be explained using our combined model. For example, if hemolysis of eukaryotic cells requires insertion of the peptide into the hydrophobic core of the membrane, which depends on the composition of the bilayer, and interaction of the non-polar face of the amphipathic α-helix with the hydrophobic lipid environment, it seems reasonable to assume that disruption of the hydrophobic surface with the Lys substitution ($NK_L$) would both disrupt dimerization of the peptide and its interaction with the hydrophobic lipid. Thus, the peptide is unable to penetrate the hydrophobic core of the membrane and unable to cause hemolysis. On the other hand, if the mechanism for prokaryotic cells allows the interaction of monomeric peptides with the phospholipid headgroups in the interface region, then no insertion into the hydrophobic core of the membrane is required for antimicrobial activity.

The biological activities of the D-enantiomeric peptides illustrated herein are consistent with the proposed model; each enantiomeric peptide pair has the same activities against prokaryotic and eukaryotic cell membranes supporting the prediction that the sole target for these antimicrobial peptides is the cell membrane. This model predicts that hemolysis of eukaryotic cells requires the peptides to be inserted into the hydrophobic core of the membrane, perpendicular to the membrane surface, and interaction of the non-polar face of the amphipathic α-helix with the hydrophobic lipid core of the bilayer. The peptide may thus form transmembrane channels/pores and the hydrophilic surfaces point inward, producing an aqueous pore ("barrel-stave" mechanism). In contrast, antimicrobial activity in prokaryotic cells, while maintaining specificity, requires the peptide to lie at the membrane interface parallel with the membrane surface and interaction of the non-polar face of the amphipathic α-helix with the hydrophobic component of the lipid and interaction of the positively charged residues with the negatively charged head groups of the phospholipid ("carpet" mechanism). What dictates the two different modes of interaction is the difference in lipid composition of prokaryotic and eukaryotic membranes. We refer to this mode of interaction of antimicrobial peptides which combines the above two mechanisms as a "membrane discrimination mechanism".

Using this model, it is easy to understand why peptide $NK_L$ and $D-NK_D$ of the present study are non-hemolytic but at the same time possess excellent antimicrobial activity compared to the native sequence $V_{681}$ or $D-V_{681}$. Thus, the single substitution of Lys for Val at position 13 ($NK_L$ and $D-NK_D$) in the center of the non-polar face disrupts the hydrophobic surface due to the presence of the positive charge, preventing the peptide from penetrating the bilayer as a transmembrane helix in eukaryotic cells. The peptide is then excluded from the bilayer and, hence, is non-hemolytic. In prokaryotic cells, the peptide is also excluded from penetrating the bilayer as a transmembrane helix but this is not required for excellent antimicrobial activity. Instead, the peptide can enter the interface region of the bilayer where disruption of the peptide hydrophobic surface by Lys can be tolerated and antimicrobial activity maintained.

In contrast, the observation that the antimicrobial activity of peptide $NL_L$ (with Leu at the substitution site) was worse than that of $NK_L$, while its hemolytic activity was stronger (MIC values of 12.7 μg/ml for $NL_L$ versus 3.1 μg/ml for $NK_L$ against Gram-negative bacteria; hemolytic activity of 7.8 μg/ml for $NL_L$ versus no detectable hemolytic activity for $NK_L$) can also be explained by our combined model. Thus, peptide $NL_L$ has a fully accessible non-polar face required for insertion into the bilayer and for interaction with the hydrophobic core of the membrane to form pores/channels ("barrel-stave" mechanism), while the hemolytic activity of peptide $NL_L$ is dramatically stronger than peptide $NK_L$. On the other hand, due to the stronger tendency of peptide $NL_L$ to be inserted into the hydrophobic core of the membrane than peptide $NK_L$, peptide $NL_L$ actually interacts less with the water/lipid interface of the bacterial membrane; hence, the antimicrobial activity is 4-fold weaker than the peptide $NK_L$ against Gram-negative bacteria. This supports the view that the "carpet" mechanism is essential for strong antimicrobial activity and if there is a preference by the peptide for penetration into the hydrophobic core of the bilayer, the antimicrobial activity will actually decrease.

The studies disclosed herein demonstrate that a high ability of a peptide to self-associate in solution correlates with weak antimicrobial activity and strong hemolytic activity of the peptides. Biological studies further show that strong hemolytic activity of the peptides generally correlates with high hydrophobicity, high amphipathicity and high helicity. In most cases, the D-amino acid substituted peptides possessed an enhanced average antimicrobial activity compared with L-diastereomers. The therapeutic index of $V_{681}$ was improved 90-fold and 23-fold against gram-negative and gram-positive bacteria, respectively. Although the antimicrobial peptides exemplified are the analogs having five amino acid (L, V, A, S, K) substitutions at position 11 or 13 in the 26-residue peptide, $V_{681}$, it is predicted that other substitutions such as ornithine, arginine, histidine or other positively charged residues at these sites would also improve antimicrobial activity of the peptides. It is further predicted that similar substitutions at position 16 or 17 of $V_{681}$ would yield peptides with enhanced biological activity. Based on the studies disclosed herein, a person of ordinary skill in the art can design antimicrobial peptides with enhanced activities by simply replacing the central hydrophobic or hydrophilic amino acid residue on the nonpolar or the polar face of an amphipathic molecule with a series of selected D-/L-amino acids.

Significant features of two specific antimicrobial peptides generated from this study in structural terms are as follows. In the case of $NK_L$, a positively-charged residue, lysine, is introduced in the center of the hydrophobic face. This substitution disrupts alpha-helical structure in benign medium, decreases dimerization, decreases toxicity to normal cells as measured by hemolytic activity, enhances antimicrobial activity and provides a 90-fold increase in the therapeutic index compared with the starting sequence against Gram-negative bacteria (substitution of starting material having Val 13 with a change to Lys 13). The therapeutic index is the ratio of hemolytic activity/antimicrobial activity. This same peptide has a 17-fold increase in the therapeutic index for Gram-positive bacteria.

In the case of $NA_D$, a D-Ala residue is introduced into the center of the hydrophobic face. This disrupts alpha-helical structure, decreases dimerization, decreases toxicity to normal cells as measured by hemolytic activity, enhances antimicrobial activity and provides a 42-fold increase in the therapeutic index compared to the starting sequence against Gram-negative bacteria (substitution is Val 13 to D-Ala 13). This same peptide has a 23-fold increase in the therapeutic index for Gram-positive bacteria.

Alpha-helical antimicrobial peptides are amphipathic; If the self-association ability of a peptide (forming dimers by interaction of the two non-polar faces of two molecules) is too strong in aqueous media, it could decrease the ability of the peptide monomers to dissociate, pass through the cell wall of microorganisms and penetrate into the biomembranes to kill target cells. It is clearly demonstrated in the studies using the D-enantiomeric peptides that there is a direct correlation of the ability of peptides to dimerize and specificity is generated, that is, disruption of dimerization generates specificity between eukaryotic and prokaryotic cells. From Table 9, the $P_A$ values of peptides derived from their temperature profiling data (FIG. 8) reflect the ability of the amphipathic α-helices to associate/dimerize. Clearly, $V_{681}$ and $D-V_{681}$, due to their uniform non-polar faces, show the greatest ability to dimerize in aqueous solution and lowest specificity or the strongest ability to lyse human erythrocytes. This is consistent with the view that a peptide with a fully accessible non-polar face tends to form pores/channels in the membranes of eukaryotic cells. In the case of $NA_D$ and $D-NA_L$, the introduction of D-Ala and L-Ala into all-L- and all-D-amino acid peptides, respectively, disrupts α-helical structure and, thus, lowers dimerization ability relative to $V_{681}$ and $D-V_{681}$ and improves specificity. The introduction of Lys into non-polar position 13 of $NK_L$ and $D-NK_D$ lowers this dimerization ability even further and improves specificity. Thus, the lack of ability of a peptide to dimerize, as exemplified by its $P_A$ value, is an excellent measure of the peptide's ability to be non-hemolytic concomitant with maintenance of sufficient hydrophobicity of the non-polar face to ensure antimicrobial activity. It is important to note that D-enantiomeric peptides exhibited the same self-association ability as their corresponding L-enantiomers; thus, similar biological activities can be expected. This is further supported by the fact that the hemolytic activity and antimicrobial activity of D-peptides against human red blood cells and microbial cells, respectively, were indeed quantitatively equivalent to those of the L-enantiomers. These results further demonstrate that there is no chiral selectivity by the membrane or other stereoselective interactions in the cytoplasm with respect to the hemolytic and antimicrobial activities.

Because of the different results on the hemolytic activity of peptide $NA_D$ shown in Tables 7 and 8, and Tables 10 and 11 (250 µg/ml after 12 hours versus 31.3 µg/ml after 18 hours, respectively), albeit using the standard microtiter dilution method (see Methods), it became apparent that an investigation of the relationship between hemolysis and time was required. It is noteworthy that there is no universal protocol of determination of hemolytic activity, which makes it difficult to compare data from different sources. For example, some researchers use 4 hours of incubation and take the minimal concentration of peptide to give 100% hemolysis as peptide hemolytic activity (28, 56); in contrast, some use 12 hours or longer (e.g., 18 hours used herein) of incubation and take the maximal concentration of peptide to give no hemolysis as peptide hemolytic activity (53, 57). Hence, the hemolysis time study is important to understand the process of erythrocyte lysis. It is clear that the degree of cell lysis is correlated with time, which may be the main reason for the different values of hemolytic activity of $NA_D$ in the two studies. Regardless, the hemolytic activity of each test peptide can readily be appreciated by a skilled artisan by comparing the value of the test peptide with that of the control peptide ($V_{681}$) within a given study. Hence, we have established a stringent criterion for toxicity, which is no hemolysis at a peptide concentration of 500 µg/ml after 8 hours. We believe that this time study at this very high peptide concentration gives a much more accurate evaluation of hemolytic activity and this method should be established as the gold standard test.

It is important to note that our lead peptides $NA_D$ and $NK_L$ are effective against a diverse group of *Pseudomonas aeruginosa* clinical isolates. Peptide $D-NA_L$ exhibited the highest antimicrobial activity against *Pseudomonas aeruginosa* strains; in contrast, $D-NK_D$ has the best overall therapeutic index due to its lack of hemolytic activity. As mentioned before, *Pseudomonas aeruginosa* is a family of notorious Gram-negative bacterial strains which are resistant to most of current antibiotics, thus, it is one of the most severe threats to human health (58-60). Only a few antibiotics are effective against *Pseudomonas*, including fluoroquinolones (61), gentamicin (62) and imipenem (63), and even these antibiotics are not effective against all strains. In the studies disclosed herein, MIC values for *Pseudomonas aeruginosa* and other Gram-negative and Gram-positive bacteria were determined in two different collaborating laboratories; in addition to different media used, the inoculum numbers of cells were also different (see details in the Methods Section), which may explain some variations of MIC values of *Pseudomonas aeruginosa* strains when comparing the results reported in Table 10 and Table 11.

As shown herein, in general, there is no significant difference in peptide antimicrobial activities against *Pseudomonas aeruginosa* strains, other Gram-negative and Gram-positive bacteria and a fungus between L- and D-enantiomeric peptides, or among peptides with different amino acid substitutions, i.e., $V_{681}$, $NA_D$ and $NK_L$ (Tables 10-12). This observation provides understanding of the mechanism of action of α-helical antimicrobial enantiomeric peptides as follows: there is a dramatic difference in peptide hydrophobicity at position 13 between Val and Lys. The Lys disrupts the continuous non-polar surface due to the positive charge and causes the peptide to locate in the interface region of the microbial membrane. This supports the view that the "carpet" mechanism is essential for strong antimicrobial activity, i.e., for both L- and D-peptide enantiomers, the peptides kill bacteria by a detergent-like mechanism, without penetrating deeply into the hydrophobic core of membrane.

Based on the peptide degradation study, all-D-peptides were totally resistant to enzymatic digestion; hence, this may explain the slightly higher antimicrobial activity of D-peptides than that of their L-enantiomers against *Pseudomonas aeruginosa* and Gram-positive bacteria. The relatively high susceptibility of L-peptides to trypsin is no doubt due to the presence of multiple lysine residues in sequences, i.e., 6 lysines for $V_{681}$ and $NA_D$, 7 lysines for $NK_L$, resulting in the fast degradation of the L-peptides in 30 minutes even at a molar ratio of 20,000:1 (peptide:trypsin).

In summary, by comparing the biophysical and biological properties of L- and D-enantiomeric peptides, we showed that L- and D-enantiomeric peptide pairs behave the same in self-association ability in solution, had the same hemolytic activity against human red blood cells, and exhibited similar antimicrobial activity against *Pseudomonas aeruginosa* strains, and other Gram-negative and Gram-positive bacteria and a fungus. No chiral selectivity was found in the antimicrobial and hemolytic activities of the peptides. Thus, the results disclosed support the "membrane discrimination" model as the mechanism of action for both L- and D-enantiomeric peptides. It is important to note that peptide D-NK$_D$ showed dramatic improvements in therapeutic indices compared to the parent peptide V$_{681}$ i.e., 53-fold against *Pseudomonas aeruginosa* strains, 80-fold against Gram-negative bacteria, 69-fold against Gram-positive bacteria and 33-fold against *C. albicans*. The proteolytic stability of D-NK$_D$, its broad spectrum of activity and lack of hemolytic activity demonstrate its clinical potential as a new therapeutic.

Methods for Example 1

Peptide Synthesis and Purification—Syntheses of the peptides Ac-KWKSFLKTFKX$_{D/L}$-AVKTVLHTALKAISS-amide (SEQ ID NO:43) and Ac-KWKSFLKTFKSAX$_{D/L}$K-TVLHTALKAISS-amide (SEQ ID NO:44), with substitution sites at positions 11 and 13, respectively were carried out by solid-phase peptide synthesis using t-butyloxycarbonyl chemistry and MBHA (4-methylbenzhydrylamine) resin (0.97 mmol/g), as described previously (26). However, it is understood in the art that there are other suitable peptide synthetic devices or that manual peptide synthesis could be carried out to produce the peptides of the present invention. The crude peptides were purified by preparative reversed-phase chromatography (RP-HPLC) using a Zorbax 300 SB-C$_8$ column (250×9.4 mm I.D.; 6.5 μm particle size, 300 Å pore size; Agilent Technologies) with a linear AB gradient (0.2% acetonitrile/min) at a flow rate of 2 ml/min, where mobile phase A was 0.1% aqueous TFA in water and B was 0.1% TFA in acetonitrile. The purity of peptides was verified by analytical RP-HPLC as described below. The peptides were further characterized by electrospray mass spectrometry and amino acid analysis.

Analytical RP-HPLC of Peptides—Peptides were analyzed on an Agilent 1100 series liquid chromatograph (Little Falls, Del.). Runs were performed on a Zorbax 300 SB-C$_8$ column (150×2.1 mm I.D.; 5 μm particle size, 300 Å pore size) from Agilent Technologies using linear AB gradient (1% acetonitrile/min) and a flow rate of 0.25 ml/min, where solvent A was 0.05% aqueous TFA, pH 2 and solvent B was 0.05% TFA in acetonitrile. Temperature profiling analyses were performed in 3° C. increments, from 5° C. to 80° C.

Characterization of Helical Structure—The mean residue molar ellipticities of peptides were determined by circular dichroism (CD) spectroscopy, using a Jasco J-720 spectropolarimeter (Jasco, Easton, Md.), at 25° C. under benign conditions (50 mM KH$_2$PO$_4$/K$_2$HPO$_4$/100 mM KCl, pH 7), as well as in the presence of an α-helix inducing solvent, 2,2,2-trifluoroethanol (TFE) (50 mM KH$_2$PO$_4$/K$_2$HPO$_4$/100 mM KCl, pH 7 buffer/50% TFE). A 10-fold dilution of a ~500 μM stock solution of the peptide analogs was loaded into a 0.02 cm fused silica cell and its ellipticity scanned from 190 to 250 nm. The values of molar ellipticities of the peptide analogs at a wavelength of 222 nm were used to estimate the relative α-helicity of the peptides.

CD Temperature Denaturation Study of Peptide V$_{681}$—The native peptide V$_{681}$ was dissolved in 0.05% aqueous TFA containing 50% TFE, pH 2, loaded into a 0.02 cm fused silica cell and peptide ellipticity scanned from 190 to 250 nm at temperatures of 5, 15, 25, 35, 45, 55, 65 and 80° C. The spectra at different temperatures were used to mimic the alteration of peptide conformation during temperature profiling analysis in RP-HPLC. The ratio of the molar ellipticity at a particular temperature (t) relative to that at 5° C. $([\theta]_t-[\theta]_u)/([\theta]_5-[\theta]_u)$ was calculated and plotted against temperature in order to obtain the thermal melting profiles, where $[\theta]_5$ and $[\theta]_u$ represent the molar ellipticity values for the fully folded and fully unfolded species, respectively. $[\theta]_u$ was determined in the presence of 8M urea with a value of 1500 deg·cm$^2$·dmol$^{-1}$ to represent a totally random coil state (31). The melting temperature (T$_m$) was calculated as the temperature at which the α-helix was 50% denatured $(([\theta]_t-[\theta]_u)/([\theta]_5-[\theta]_u)=0.5)$ and the values were taken as a measure of α-helix stability.

Determination of Peptide Amphipathicity—Amphipathicity of peptide analogs was determined by the calculation of hydrophobic moment (32) using the software package Jemboss version 1.2.1 (33), modified to include a hydrophobicity scale determined in our laboratory. The hydrophobicity scale used in this study is listed as follows: Trp, 32.31; Phe, 29.11; Leu, 23.42; Ile 21.31; Met, 16.13; Tyr, 15.37; Val, 13.81; Pro, 9.38; Cys, 8.14; Ala, 3.60; Glu, 3.60; Thr, 2.82; Asp, 2.22; Gln, 0.54; Ser, 0.00; Asn, 0.00; Gly, 0.00; Arg, −5.01; His, −7.03; Lys, −7.03 (Hodges, et al. unpublished data). These hydrophobicity coefficients were determined from reversed-phase chromatography at pH 2 of a model random coil peptide with single substitution of all 20 naturally occurring amino acids. In this case, the amphipathicity is valid for neutral and acidic pH since V$_{681}$ and analogs do not have Asp and Glu residues in their sequences. We propose that this HPLC-derived scale reflects the relative differences in hydrophilicity/hydrophobicity of the 20 amino acid side-chains more accurately than previously determined scales.

Measurement of Antimicrobial Activity—Minimal inhibitory concentrations (MICS) were determined using a standard microtiter dilution method in LB (Luria-Bertani) no-salt medium (10 g of tryptone and 5 g of yeast extract per liter). Briefly, cells were grown overnight at 37° C. in LB and diluted in the same medium. Serial dilutions of the peptides were added to the microtiter plates in a volume of 100 μl followed by 10 μl of bacteria to give a final inoculum of 5×10$^5$ colony-forming units/ml. Plates were incubated at 37° C. for 24 hours and MICS determined as the lowest peptide concentration that inhibited growth. Alternatively, minimal inhibitory concentrations were determined using a standard microtiter dilution method in a Mueller-Hinton (MH) medium. Briefly, cells were grown overnight at 37° C. in MH broth and diluted in the same medium. Serial dilutions of the peptides were added to the microtiter plates in a volume of 100 μl followed by 10 μl of bacteria to give a final inoculum of 1×10$^5$ colony-forming units/ml. Plates were incubated at 37° C. for 24 hours and MICS determined as the lowest peptide concentration that inhibited growth. However, for MIC determination of *Pseudomonas aeruginosa* clinical isolates, brain heart infusion (BH1) medium was used instead of MH broth. In addition, the bacteria were diluted to a final inoculum of 1×10$^6$ colony-forming units/ml.

Measurement of Hemolytic Activity—Protocol A: Peptide samples were added to 1% human erythrocytes in phosphate buffered saline (0.08M NaCl; 0.043M Na$_2$PO$_4$; 0.011 M KH$_2$PO$_4$) and reactions were incubated at 37° C. for 12 hours in microtiter plates. Peptide samples were diluted 2 fold in order to determine the concentration that produced no hemolysis. This determination was made by withdrawing aliquots from the hemolysis assays, removing unlysed erythrocytes by centrifugation (800 g) and determining which concentration of peptide failed to cause the release of hemoglobin. Hemoglobin release was determined spectrophotometrically at 562 nm. The hemolytic titer was the highest 2-fold dilution of the peptide that still caused release of hemoglobin from erythrocytes. The control for no release of hemoglobin was a sample of 1% erythrocytes without any peptide added. The results shown in Tables 5-7 were obtained by using Protocol A. Protocol B: Alternatively, peptide samples were added to 1% human erythrocytes in phosphate buffered saline (100 mM NaCl; 80 mM Na$_2$HPO4; mM NaH$_2$PO$_4$, pH 7.4) and reactions were incubated at 37° C. for 18 hours in microtiter plates. Peptide samples were diluted 2 fold in order to determine the concentration that produced no hemolysis. This determination was made by withdrawing aliquots from the hemolysis assays, removing unlysed erythrocytes by centrifugation (800 g) and determining which concentration of peptide failed to cause the release of hemoglobin. Hemoglobin release was determined spectrophotometrically at 570 nm. The hemolytic titer was the highest 2-fold dilution of the peptide that still caused release of hemoglobin from erythrocytes. The control for no release of hemoglobin was a sample of 1% erythrocytes without any peptide added. Since erythrocytes were in an isotonic medium, no detectable release (<1% of that released upon complete hemolysis) of hemoglobin was observed from this control during the course of the assay. For the hemolysis time study, hemolytic activity of peptides at concentrations of 8, 16, 32, 64, 125, 250 and 500 μg/ml was measured at 0, 1, 2, 4, 8 hours at 37° C. The results shown in Tables 10-12 were obtained by using Protocol B.

Calculation of Therapeutic Index (MHC/MIC Ratio)—it should be noted that both MHC and MIC values were determined by serial 2-fold dilutions. Thus, for individual bacteria and individual peptides the therapeutic index (MHC/MIC, "TI") could vary by as much as 4 fold if the peptide is very active in both hemolytic and antimicrobial activities; if a peptide has poor or no hemolytic activity, the major variation in the therapeutic index (MHC/MIC) comes from the variation in the MIC value (as much as 2-fold).

Proteolytic Stability Assay—Proteolytic stability of the peptides was carried out with trypsin in a molar ratio of 1:20,000 (trypsin:peptide=0.1 μM:2 mM). The buffer used was 50 mM NH$_4$HCO$_3$ at pH 7.4 for both peptides and enzyme. The mixtures of peptide and trypsin were incubated at 37° C. Samples were collected at time points of 0, 5 min, 10 min, 20 min, 30 min, 1, 2, 4, 8 hours. Equal volumes of 20% aqueous TFA were added to each sample to stop the reaction and peptide degradation was checked by RP-HPLC. Runs were performed on a Zorbax 300 SB-C$_8$ column (150×2.1 mm I.D.; 5 μm particle size, 300 Å pore size) from Agilent Technologies at room temperature using a linear AB gradient (1% acetonitrile/min) and a flow rate of 0.25 ml/min, where eluent A was 0.2% aqueous TFA, pH 2 and eluent B was 0.2% TFA in acetonitrile. The change in integrated peak area of the peptides was used to monitor the degree of proteolysis during the time study.

EXAMPLE 2

Peptide Analogs with Varied Position of Substitution

Further peptides of the invention are generated by varying the position of a substitution. By denoting the center position as "i", varied positions of substitutions can be generated while retaining a preferred location on the desired face, e.g. the non-polar face. In the relative context of SEQ ID NO:1, for example, the position for substitution is selected from the group consisting of i, i−4, i−8, i+4, and i+8. See FIG. 7A for examples of specific variants achieved by optional positioning of substitutions. Without wishing to be bound by a particular theory, it is hypothesized that a peptide with the substitution at position i of $K_L$ (e.g., in SEQ ID NO:6), in the center position of the non-polar face, can have greater biological activity than a peptide with a substitution at a position further away from the center position. According to such theory, the therapeutic index can decrease in the order of $K_L13>K_L9>K_L5$ (here the numeral indicates the position of the amino acid substitution relative to SEQ ID NO:1). Similarly, the therapeutic index can decrease in the order of $A_D13>A_D9>A_D5$ (here $A_D13$ corresponds to SEQ ID NO:9). Regardless of such theory, such peptides with varied positions of a substitution can have activity and be useful in compositions and methods of the invention. Successful substitutions at position 13 can also work near the center of the hydrophobic face at position 9, 12, 16 and 17 (see helical net diagram in FIG. 1).

In order to evaluate the biological activities of the peptide analogs with varied position of substitution, we used peptide $NK_L$ as a framework to systematically alter the peptide hydrophobicity by replacing alanine residues with hydrophobic leucine residues on the non-polar face of the helix. Peptide sequences are shown in Table 13.

TABLE 13

Sequences of NK$_L$ analog peptides.

| Number | Denotation | Peptide sequences[a] |
|---|---|---|
| 1 | NK$_L$ (SEQ ID NO: 6) | Ac-KWKSFLKTFKSAKKTVLHTA LKAISS-amide |
| 2 | A23L (SEQ ID NO: 45) | Ac-KWKSFLKTFKSAKKTVLHTA LKLISS-amide |
| 3 | A12L (SEQ ID NO: 46) | Ac-KWKSFLKTFKSLKKTVLHTA LKAISS-amide |
| 4 | A20L (SEQ ID NO: 47) | Ac-KWKSFLKTFKSAKKTVLHTL LKAISS-amide |
| 5 | A12L/ A23L (SEQ ID NO: 48) | Ac-KWKSFLKTFKSLKKTVLHTA LKLISS-amide |
| 6 | A12L/ A20L (SEQ ID NO: 49) | Ac-KWKSFLKTFKSLKKTVLHTL LKAISS-amide |
| 7 | A12L/A20L/ A23L (SEQ ID NO: 50) | Ac-KWKSFLKTFKSLKKTVLHTL LKLISS-amide |

[a]Peptide sequences are shown using the one-letter code for amino acid residues; Ac- denotes N$^\alpha$-acetyl and -amide denotes C$^\alpha$-amide; in sequences, bold letters denote the substituting amino acids at the non-polar face of NK$_L$ (see FIG. 1 for details).

Figure 12:
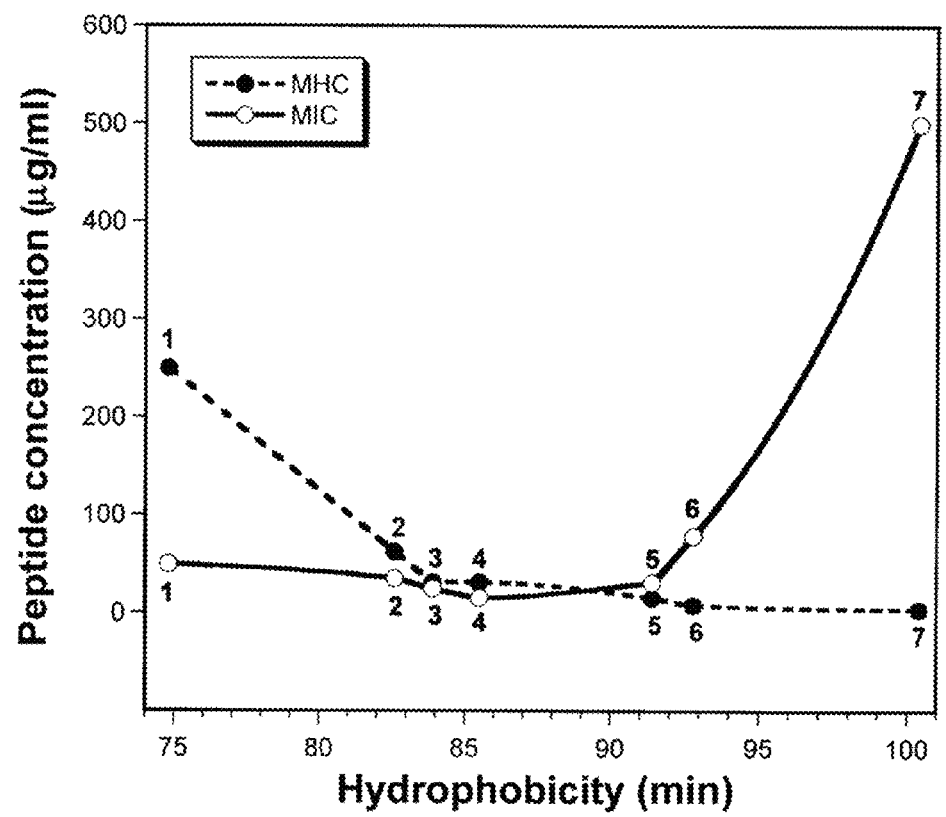
FIG. 12 illustrates the relationship of peptide hydrophobicity and antimicrobial activity (MIC) and hemolytic activity (MHC). Closed symbols and dotted line represent the relationship between hydrophobicity and hemolytic activity; open symbols and solid line represent the relationship between hydrophobicity and antimicrobial activity. Hydrophobicity was shown as the retention time of peptides in RP-HPLC at room temperature. The lines were drawn to guide the eye.

FIG. 12 shows the leucine-substituted peptide analogs represented as helical nets. Since there are three alanine residues on the non-polar face of peptide V13K$_L$, three single Leu-substituted analogs were synthesized with an Ala→Leu substitution at positions 12, 20 and 23; two double Leu-substituted peptides (A12L/A23L and A12L/A20L) and a triple Leu-substituted peptide (A12L/A20L/A23L) were also made to increase hydrophobicity. In FIG. 12, the i→i+3 and i→i+4 hydrophobic interactions are shown as black bars. It is clear that, for single Leu-substituted analogs, the number of hydrophobic interactions created by these substitutions in the three peptides is in the order of A20L>A12L>A23L (9, 8 and 6 hydrophobic interactions, respectively); for peptides with double leucine substitutions, A12L/A20L has more hydrophobic interactions than A12L/A23L (11 versus 8 hydrophobic interactions); peptide A12L/A20L/A23L presented the highest number of i→i+3 and i→i+4 hydrophobic interactions (12 hydrophobic interactions) among all the peptide analogs as expected. In this study, peptides were simply named after the positions of the leucine substitutions.

For the Leu-substituted peptides, the hemolytic activity against human erythrocytes was determined as the maximal peptide concentration that produces no hemolysis after 18 hours of incubation at 37° C. Antimicrobial activity of the peptides was determined on a diverse group of *Pseudomonas aeruginosa* clinical isolates. *Pseudomonas* is a family of strains that has become more and more resistant to various traditional antibiotics since 1990s and it is also known to produce proteolytic enzymes which make it even less susceptible to antimicrobial peptides (58-60). *Pseudomonas aeruginosa* strains used in this study exhibited a wide range of ciprofloxacin susceptibility (a 64-fold difference) (Table 14). The most resistant *Pseudomonas aeruginosa* strain was CP204, a clinical isolate from cystic fibrosis patients, which was, in contrast, the most susceptible strain to our antimicrobial peptides in this study. This indicates that there is no correlation between antibiotic resistance and the ability of antimicrobial peptides to be effective. The geometric mean MIC values from six *Pseudomonas* strains in Table 14 were calculated to provide an overall evaluation of antimicrobial activity of the peptides with different hydrophobicities.

action for antimicrobial peptides whose sole target is the biomembrane. We believe that the mechanism depends upon the compositional difference in the lipids between prokaryotic and eukaryotic membranes. It is well-known that eukaryotic cell membranes are in contrast to prokaryotic membranes generally characterized by zwitterionic phospholipids, a relatively large amount of cholesterol and sphigomyelin, and the absence of a high, inside-negative transmembrane potential presented in prokaryotic membranes (51-52, 66-67). Hence, if the peptides form pores/channels in the hydrophobic core of the eukaryotic bilayer, they would cause the hemolysis of erythrocytes; in contrast, for prokaryotic cells the peptides lyse cells in a detergent-like mechanism as described in the carpet mechanism (46).

The observation that there is a correlation between peptide hydrophobicity and hemolytic activity can be explained by the "membrane discrimination" mechanism. Peptides with higher hydrophobicity will penetrate deeper into the hydrophobic core of red blood cell membrane (67), causing stronger hemolysis by forming pores or channels, i.e., A12L/A23L (peptide 5) and A12L/A20L (peptide 6) exhibited stronger hemolytic activity than single Leu-substituted peptides, and A12L/A20L/A23L (peptide 7) showed the strongest hemolytic activity in this study (Table 14). For peptide anti-

TABLE 14

Biological activities of $NK_L$ analog peptides.

| Peptide | | Hemolytic activity | | Antimicrobial activity | | | | | | | |
|---|---|---|---|---|---|---|---|---|---|---|---|
| | | | | MIC $(\mu g/ml)^b$ | | | | | | | |
| Number | Denotation | MHC $(\mu g/ml)$ | Fold$^a$ | PAO 1 | WR 5 | PAK | PA 14 | M 2 | CP 204 | GM$^c$ | Fold$^d$ |
| 1 | $NK_L$ | 250.0 | 1.0 | 31.3 | 250.0 | 125.0 | 62.5 | 31.3 | 7.8 | 49.6 | 1.0 |
| 2 | A23L | 62.5 | 4.0 | 31.3 | 62.5 | 62.5 | 31.3 | 31.3 | 15.6 | 35.1 | 1.4 |
| 3 | A12L | 31.3 | 8.0 | 15.6 | 62.5 | 31.3 | 31.3 | 15.6 | 15.6 | 24.8 | 2.0 |
| 4 | A20L | 31.3 | 8.0 | 7.8 | 31.3 | 31.3 | 15.6 | 15.6 | 7.8 | 15.6 | 3.2 |
| 5 | A12L/A23L | 15.6 | 16.0 | 15.6 | 250.0 | 15.6 | 62.5 | 31.3 | 7.8 | 31.2 | 1.6 |
| 6 | A12L/A20L | 8.0 | 32.0 | 62.5 | 125.0 | 62.5 | 125.0 | 62.5 | 62.5 | 78.7 | 0.6 |
| 7 | A12L/A20L/A23L | 4.0 | 62.5 | 500.0 | 500.0 | 500.0 | 500.0 | 500.0 | 500.0 | 500.0 | 0.1 |
| | Ciprofloxacin$^e$ | | | 4 | 1 | 4 | 8 | 8 | 64 | | |

$^a$denotes the fold increase in hemolytic activity compared to the parent peptide $NK_L$. Hemolytic activity (MHC, the maximal peptide concentration showing no hemolysis after 18 hours) was determined on human red blood cells (hRBC).
$^b$MIC is minimal inhibitory concentration against 6 *Pseudomonas aeruginosa* clinical isolates.
$^c$denotes the geometric mean of the MIC values for the 6 *Pseudomonas aeruginosa* clinical isolates.
ddenotes the fold improvement in antimicrobial activity (geometric mean data) compared to the parent peptide $NK_L$.
$^e$Relative susceptibility of these *Pseudomonas* strains to ciprofloxacin with the number 1 denoting the most susceptible strain.

Figure 13:
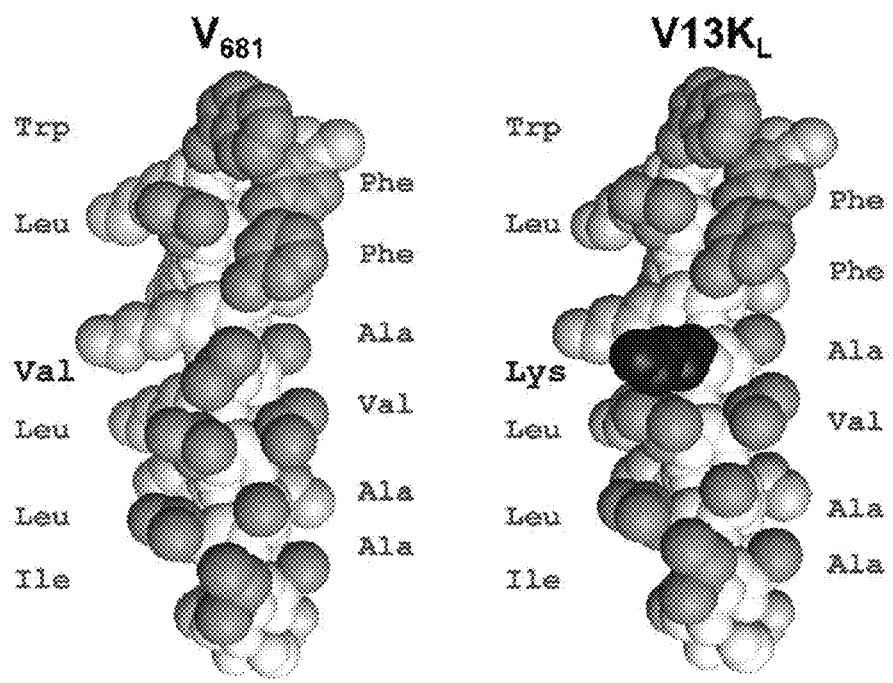
FIG. 13 illustrates a space-filling model of peptides V681 and V13KL. Hydrophobic amino acids on the non-polar face of the helix are green; hydrophilic amino acids on the polar face of the helix are grey; peptide backbone is colored white. The Lys substitution at position 13 (V13KL) on the non-polar face of the helix is blue. The models were created by the PyMOL v0.98.

The influence of peptide hydrophobicity on biological activities is shown in FIG. 13. It was generally accepted that increasing the hydrophobicity of the non-polar face of the amphipathic α-helical peptides would increase both hemolytic and antimicrobial activities (5-8). In the present study, it is clear that peptide hydrophobicity correlated with peptide hemolytic activity in that the more hydrophobic the peptide the stronger the hemolytic activity to erythrocytes, which is consistent with previous results (53, 64-66). The striking result from our antibacterial assay was that hydrophobicity has two effects on peptide antimicrobial activity: at a relative low level of hydrophobicity, increasing peptide hydrophobicity caused an improvement in antimicrobial activity until an optimum hydrophobicity was reached; in contrast, peptide antimicrobial activity was weakened dramatically with further increases of hydrophobicity beyond the optimum, even resulting in the loss of antimicrobial activity of peptide A12L/A20L/A23L (peptide 7) in this study (FIG. 12).

The results of these studies are consistent with our proposed model of "membrane discrimination" mechanism of microbial activity, since the insertion of the molecules into the hydrophobic core is not necessary to lyse bacterial cells during the antibacterial action, peptides only lie at the interface parallel with the membrane allowing their hydrophobic surface to interact with the hydrophobic component of the lipid, and the positive charge residues to interact with the negatively charged head groups of the phospholipids (46,47). Thus, it is reasonable to assume that increasing peptide hydrophobicity to a certain extent will help peptide molecules to reach the interface from aqueous environment and improve antimicrobial activity. In this study, the improvement of antimicrobial activity from peptide $NK_L$ (peptide 1) to peptide A20L (peptide 4) can represent such an advantage of increasing hydrophobicity. In contrast, further increases in hydrophobicity will cause the stronger peptide dimerization in solution which in turn results in the monomer-dimer equilibrium favoring the dimer conformation. Peptide dimers are in their folded α-helical conformation and would be inhibited from passing through the cell wall to reach the target membranes. Hence the antimicrobial activities of peptides A12L/A23L (peptide 5) and A12L/A20L (peptide 6) become weaker with increasing hydrophobicity compared to the single Leu-substituted analogs. We believe that there is a threshold of hydrophobicity controlling peptide antimicrobial activity, that is, one may adjust peptide hydrophobicity to obtain the optimal antimicrobial activity. For the extreme example of the triple-Leu-substituted analog, A12L/A20L/A23L (peptide 7), the loss of antimicrobial activity may be explained as due to its very strong dimerization ability in aqueous environments. Hence, the peptide exists mainly as a dimer in solution and it would not pass through the bacterial cell wall. In contrast, there is no polysaccharide-based cell wall in eukaryotic cells, thus, A12L/A20L/A23L (peptide 7) caused severe hemolysis against human red blood cells where the hydrophobicity of the bilayer causes rapid dissociation of dimers to monomers and entry into the bilayer to form channels/pores.

EXAMPLE 3

Peptide Analogs with Varied Nature of Charge Substitution

Further peptides of the invention are generated by varying the nature of the charged residue selected for the substitution. In the relative context of SEQ ID NO:1, for example, the position for substitution is established as position 13. The amino acid selected for substitution is preferably a charged amino acid and is in particular an amino acid with a net positive charge. Particular examples of charged residues at position 13 are Lys, Arg, Orn, His, diamino butyric acid and diamino propionic acid. We note that Orn has a delta/δ-amino group instead of an epsilon/ε-amino group in Lys, i.e., the side-chain is shorter by one carbon atom; diaminobutanoic acid is one carbon shorter than Orn; i.e., it has a gamma/γ-amino group; diaminopropionic acid is two carbons shorter than Orn, i.e., it has a beta/β-amino group.

Figure 7A:
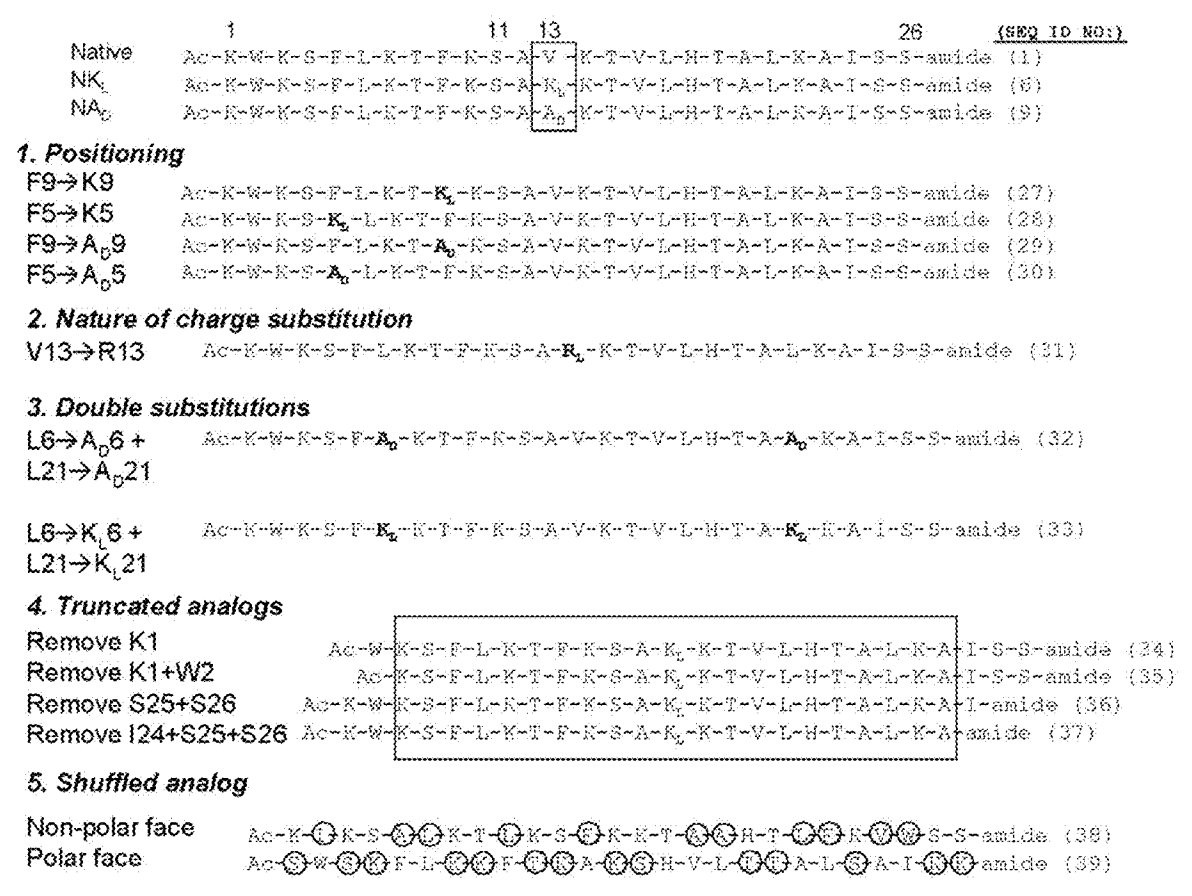

See FIG. 7A for a specific variant peptide achieved by optional selection of charged residues for use in substitutions. A peptide with a charged residue in the center of the non-polar face can be active. Without wishing to be bound by a particular theory, it is hypothesized that the activity of a peptide with such a centrally positioned positively charged residue can be modulated depending on the positively charged residue, although there may be difficulty in predicting the precise effect upon an activity parameter such as the therapeutic index as described herein.

EXAMPLE 4

Peptide Analogs with Multiple Substitutions

Further peptides of the invention are generated by using multiple substitutions relative to a reference sequence such as SEQ ID NO:1. In a preferred embodiment, the multiple substitutions are a double substitution. In the relative context of SEQ ID NO:1, for example, the following peptides are made with double substitutions: a) peptide with substitution combination of L6 to $A_D6$ and L21 to $A_D21$; and b) peptide with substitution combination of L6 to $K_L6$ and L21 to $K_L21$. See FIG. 7A for specific variant peptides achieved by optional multiple substitutions.

Without wishing to be bound by a particular theory, it is hypothesized that the activity of a peptide with multiple substitutions (e.g. two substitutions) not in the center position can still be effective. For a particular peptide generated by multiple substitutions, such multiple substitutions can be at least as effective as a single substitution in the center of the non-polar face. Alternatively, a given multiple substitution such as the specific double substitutions shown may not be as effective as the single substitutions described herein due to the removal of two Leu residues instead of one Val residue. A decrease in hydrophobicity can optionally result in a decrease in the therapeutic index. In addition, the double D-Ala substitutions may be more disruptive of the helical structure; such disruption can also yield a decrease in the therapeutic index. Analogous results can be achieved for the double L-Lys substitutions.

EXAMPLE 5

Truncated Peptide Analogs

Further peptides of the invention are generated by truncation of a reference peptide such as SEQ ID NO:1 or a peptide of the invention such as any of SEQ ID NOS: 2 to 25 (except for those peptides that are exactly equivalent to SEQ ID NO:1 such as SEQ ID NO: 3 and 15), or other peptide of the invention as described herein. In a truncated peptide analog, for example, truncation of the N-terminal residue Lys1 or C-terminal residues Ser25 and Ser26 do not substantially affect the biological properties such as activity of the truncated peptide. See FIG. 7A for specific variant peptides achieved by optional truncations in the relative context of peptide $NK_L$ (SEQ ID NO:6). Without wishing to be bound by a particular theory, it is hypothesized that truncating the N-terminal residue Lys1 or C-terminal residues Ser25 and Ser26 does not substantially affect the biological properties. It is believed, however, that truncation of Lys1 and Trp2 can substantially decrease the therapeutic index due to removal of the large hydrophobe, Trp. Similarly, truncation of Ser26, Ser25 and Ile24 can substantially decrease the therapeutic index due to removal of the large hydrophobe, Ile.

As further alternatives to truncated analog peptides corresponding to SEQ ID 34, 35, 36, and 37, there is a substitution of K13V (the K at position 13 is replaced by V) for each of those respective peptides.

EXAMPLE 6

Shuffled Peptide Analogs

Figure 7B:
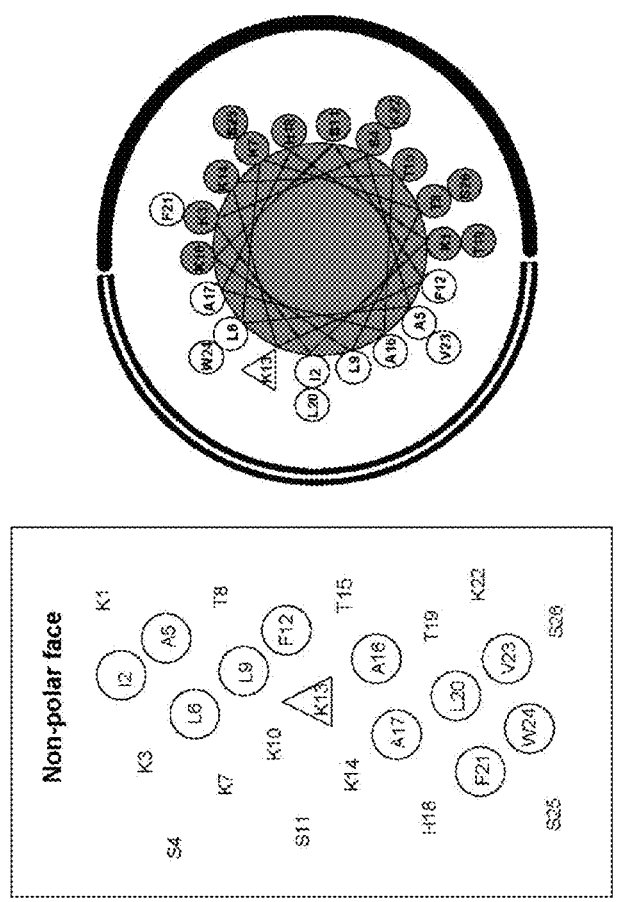
FIG. 7B illustrates variants based on shuffling of the non-polar face residues.

Further peptides of the invention are generated by shuffling various residues. For residues on the non-polar face, shuffling is performed to generate various non-polar face analogs. It is believed that the overall hydrophobicity of the non-polar face is an important factor in biological activity. The hydrophobic residues on the non-polar face are shuffled wherein a resulting peptide is biologically active. As shown in FIG. 7A and FIG. 7B, the circled residues in the sequence are the shuffled residues on the non-polar face.

Figure 7C:
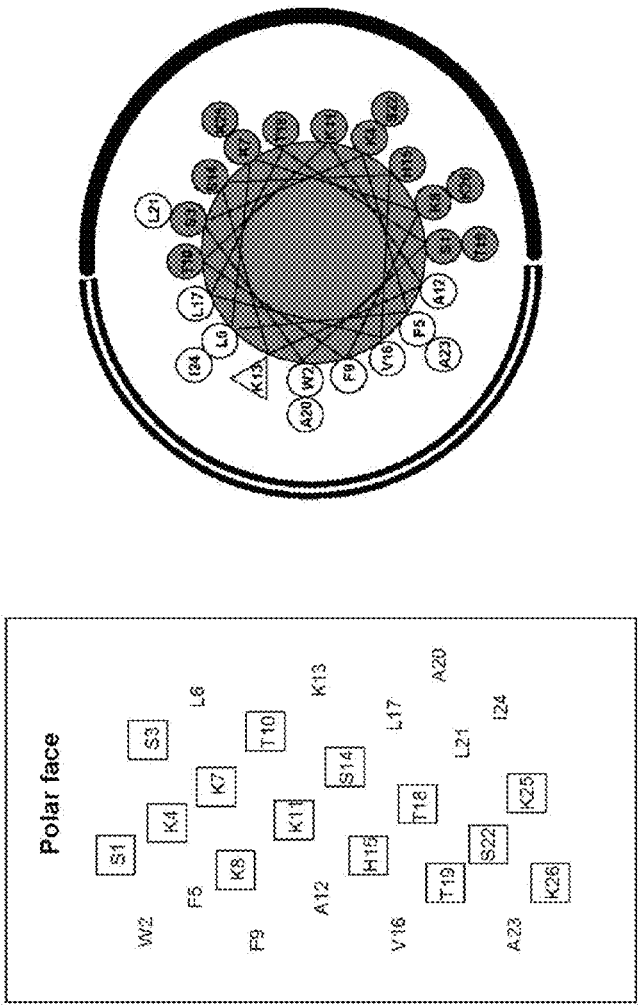
FIG. 7C illustrates variants based on shuffling of the polar face residues.

For residues on the polar face, shuffling is performed to generate various polar face analogs. It is believed that the polar face is an important factor in maintaining the amphipathicity of the molecule and significant properties such as biological activity. The polar residues on the polar face are shuffled wherein a resulting peptide is biologically active. As shown in FIG. 7A and FIG. 7C, the circled residues in the sequence are the shuffled residues on the polar face.

Shuffling of the non-polar face residues or polar face residues does not substantially change the amphipathicity of the molecule, or the overall hydrophobicity of the non-polar face or the overall hydrophilicity of the polar face. Though a particular sequence may be a preferred or the best analog, other analogs can nonetheless have useful biological properties.

In particular peptides, shuffling the 11 residues on the non-polar face is performed, excluding the substitution site (for example so as to preserve β-Lys as in $NK_L$), to any combination of sequences that contain 1 W (one tryptophan residue), 2 F, 3 L, 3 A, 1 V and 1 I residue. Similarly, shuffling the 14 residues on the polar face to any combination of sequences that contains 6 K, 4 S, 3 T, and 1 H residue is performed.

Peptides are generated having a range of overall hydrophobicity of the non-polar face. The hydrophobicity of the non-polar face can be calculated using a sum of the hydrophobicity coefficients listed in the manuscript. For example, a particular hydrophobicity range is of $NK_L$ or $NA_D$±the value of a Leu side-chain. Using our scale, the hydrophobicity of the non-polar face of $NK_L$ sums up the values for W2, F5, L6, F9, A12, K13, V16, L17, A20, L21, A23, I24 getting a value of 199.7. See Table 15.

TABLE 15

Hydrophobicity coefficients.

| Item | Coefficient |
| --- | --- |
| Trp 2 | 32.31 |
| Phe 5 | 29.11 |
| Leu 6 | 23.42 |
| Phe 9 | 29.11 |
| Ala 12 | 3.60 |
| Lys 13 | −7.03 |
| Val 16 | 13.81 |
| Leu 17 | 23.42 |
| Ala 20 | 3.60 |
| Leu 21 | 23.42 |
| Ala 23 | 3.60 |
| Ile 24 | 21.31 |
| SUM | 199.7 ± 23.42 |

Different scales can give different values. For peptides herein, there is significance in the sum of the residues in the hydrophobic surface, using our scale, where the surface hydrophobicity range that generates the desired biological activity is from about 176 to about 224.

The sum of the hydrophobicity coefficients for the polar face should be the value for $NK_L$ peptide±the value of a Lys residue.

TABLE 16

Coefficient values.

| Item | Coefficient |
| --- | --- |
| K1 | −7.03 |
| K3 | −7.03 |
| S4 | 0.00 |
| K7 | −7.03 |
| T6 | +2.82 |
| K10 | −7.03 |
| S11 | 0.00 |
| K14 | −7.03 |
| T15 | +2.82 |
| H18 | −7.03 |
| T19 | +2.82 |
| K22 | −7.03 |
| S25 | 0.00 |
| S26 | 0.00 |
| SUM | −40.75 ± 7.03 |

Using our scale, the hydrophobicity of the polar face of $NK_L$ sums up the values K1, K3, S4, K7, T6, K10, S11, K14, T15, H18, T19, K22, S25 and S26. The range of surface hydrophilicity that generates the desired biological activity is from about −33 to about −48.

EXAMPLE 7

Peptide Analogs with Similar Single Hydrophobicity Substitutions

Further peptides of the invention are generated by making single substitutions of amino acid residues with relatively similar hydrophobicity. Single hydrophobicity substitutions with side-chains of similar hydrophobicity are generated and have biological activity. For example, possible substitutions for each residue in the non-polar face are listed below in Table 17 in the context of peptides $NK_L$ and $NA_D$ (SEQ ID NOS:6 and 9, respectively).

TABLE 17

Residues for single substitutions.

| Residue in $NK_L$ or $NA_D$ | Substituting residues |
| --- | --- |
| Leu | Ile, Val, norleucine, norvaline |
| Ile | Leu, Val, norleucine, norvaline |
| Val | Leu, Ile, norleucine, norvaline |
| Phe | Leu, Ile, Val, norleucine, norvaline |
| Trp | Phe, Leu, Ile, Val, norleucine, norvaline |

EXAMPLE 8

Peptide Analogs of $NA_D$ and $D$-$NA_L$

Further compositions and methods are provided where the hemolytic activity of $NA_D$ or $D$-$NA_L$ is further decreased by decreasing the overall hydrophobicity of the non-polar face. See Kondejewski, L. H., et al. 2002, J. Biol. Chem. 277:67-74. For example, V16 is substituted to A16; or L17 to A17; or both V16, L17 to A16, A17. A decreased hydrophobicity can decrease hemolytic activity as shown for substitutions herein at position 13. The hydrophobicity can decrease approximately in the order $NL_L > NV_Q > NA_L > NG > NS_L > NK_L$ which correlates with the weakening of hemolytic activity (µg/ml) where $NL_L$ (7.8), $NV_Q$ (15.6), $NA_L$ (31.2), NG (125), $NS_A$ (125) and $NK_L$ (no measurable activity). It is recognized that there can be a threshold of hydrophobicity which when excessively decreased can result in peptides where the biological property of antimicrobial activity is substantially reduced.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Any appendix or appendices hereto are incorporated by reference as part of the specification and/or drawings.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof.

The invention has been described with reference to various specific and preferred embodiments and techniques. However, it should be understood that many variations and modifications may be made while remaining within the true spirit and scope of the invention. It will be apparent to one of ordinary skill in the art that compositions, methods, devices, device elements, materials, procedures and techniques other than those specifically described herein can be applied to the practice of the invention as broadly disclosed herein without resort to undue experimentation. All art-known functional equivalents of compositions, methods, devices, device elements, materials, procedures and techniques described herein are intended to be encompassed by this invention. It is not intended, however, for any claim herein to specifically encompass any precise embodiment existing and legally qualifying in the relevant jurisdiction as prior art for novelty; a claim purportedly encompassing such an embodiment is intended to be of scope so as to just exclude any such precise embodiment.

Whenever a range is disclosed, all subranges and individual values are intended to be encompassed. This invention is not to be limited by the embodiments disclosed, including any shown in the drawings or exemplified in the specification, which are given by way of example or illustration and not of limitation.

REFERENCES

1. Neu, H. C. (1992) *Science* 257, 1064-1073
2. Travis, J. (1994) *Science* 264, 360-362
3. Hancock, R. E. (1997) *Lancet* 349, 418-422
4. Andreu, D., and Rivas, L. (1998) *Biopolymers* 47, 415-433
5. Sitaram, N., and Nagaraj, R. (2002) *Curr Pharm Des* 8, 727-742
6. Hancock, R. E., and Lehrer, R. (1998) *Trends Biotechnol* 16, 82-88
7. Duclohier, H., Molle, G., and Spach, G. (1989) *Biophys J* 56, 1017-1021
8. van't H of, W., Veerman, E. C., Helmerhorst, E. J., and Amerongen, A. V. (2001) *Biol Chem* 382, 597-619
9. Devine, D. A., and Hancock, R. E. (2002) *Curr Pharm Des* 8, 703-714
10. Ganz, T., and Lehrer, R. I. (1994) *Curr Opin Immunol* 6, 584-589
11. Steinberg, D. A., Hurst, M. A., Fujii, C. A., Kung, A. H., Ho, J. F., Cheng, F. C., Loury, D. J., and Fiddes, J. C. (1997) *Antimicrob Agents Chemother* 41, 1738-1742
12. Khaled, M. A., Urry, D. W., Sugano, H., Miyoshi, M., and Izumiya, N. (1978) *Biochemistry* 17, 2490-2494
13. Mootz, H. D., and Marahiel, M. A. (1997) *J Bacteriol* 179, 6843-6850
14. Christensen, B., Fink, J., Merrifield, R. B., and Mauzerall, D. (1988) *Proc Natl Acad Sci USA* 85, 5072-5076
15. Zasloff, M. (1987) *Proc Natl Acad Sci USA* 84, 5449-5453
16. Andreu, D., Ubach, J., Boman, A., Wahlin, B., Wade, D., Merrifield, R. B., and Boman, H. G. (1992) *FEBS Lett* 296, 190-194
17. Dathe, M., Wieprecht, T., Nikolenko, H., Handel, L., Maloy, W. L., MacDonald, D. L., Beyermann, M., and Bienert, M. (1997) *FEBS Lett* 403, 208-212
18. Blondelle, S. E., and Houghten, R. A. (1992) *Biochemistry* 31, 12688-12694
19. Lee, D. L., and Hodges, R. S. (2003) *Biopolymers* 71, 28-48
20. Kondejewski, L. H., Jelokhani-Niaraki, M., Farmer, S. W., Lix, B., Kay, C. M., Sykes, B. D., Hancock, R. E., and Hodges, R. S. (1999) *J Biol Chem* 274, 13181-13192
21. Oren, Z., Hong, J., and Shai, Y. (1997) *J Biol Chem* 272, 14643-14649
22. Kondejewski, L. H., Lee, D. L., Jelokhani-Niaraki, M., Farmer, S. W., Hancock, R. E., and Hodges, R. S. (2002) *J Biol Chem* 277, 67-74
23. Shai, Y., and Oren, Z. (1996) *J Biol Chem* 271, 7305-7308
24. Oren, Z., and Shai, Y. (1997) *Biochemistry* 36, 1826-1835
25. Lee, D. L., Powers, J. P., Pflegerl, K., Vasil, M. L., Hancock, R. E., and Hodges, R. S. (2004) *J Pept Res* 63, 69-84
26. Chen, Y., Mant, C. T., and Hodges, R. S. (2002) *J Pept Res* 59, 18-33
27. Zhang, L., Falla, T., Wu, M., Fidai, S., Burian, J., Kay, W., and Hancock, R. E. (1998) *Biochem Biophys Res Commun* 247, 674-680
28. Zhang, L., Benz, R., and Hancock, R. E. (1999) *Biochemistry* 38, 8102-8111
29. Mant, C. T., Chen, Y., and Hodges, R. S. (2003) *J Chromatogr A* 1009, 29-43
30. Lee, D. L., Mant, C. T., and Hodges, R. S. (2003) *J Biol Chem* 278, 22918-22927
31. Monera, O. D., Sereda, T. J., Zhou, N. E., Kay, C. M., and Hodges, R. S. (1995) *Journal of peptide science* 1, 319-329
32. Eisenberg, D., Weiss, R. M., and Terwilliger, T. C. (1982) *Nature* 299, 371-374
33. Carver, T., and Bleasby, A. (2003) *Bioinformatics* 19, 1837-1843
34. Zhou, N. E., Monera, O. D., Kay, C. M., and Hodges, R. S. (1994) *Protein Peptide Lett.* 1, 114-119
35. McInnes, C., Kondejewski, L. H., Hodges, R. S., and Sykes, B. D. (2000) *J Biol Chem* 275, 14287-14294
36. Mant, C. T., Zhou, N. E., and Hodges, R. S. (1993) in *The Amphipathic Helix* (Epand, R. M., ed), pp. 39-64, CRC Press, Boca Raton
37. Mant, C. T., and Hodges, R. S. (2002) *J Chromatogr A* 972, 61-75
38. Mant, C. T., and Hodges, R. S. (2002) *J Chromatogr A* 972, 45-60
39. Zhou, N. E., Mant, C. T., and Hodges, R. S. (1990) *Pept Res* 3, 8-20
40. Blondelle, S. E., Ostresh, J. M., Houghten, R. A., and Perez-Paya, E. (1995) *Biophys J* 68, 351-359
41. Purcell, A. W., Aguilar, M. I., Wettenhall, R. E., and Hearn, M. T. (1995) *Pept Res* 8, 160-170
42. Mant, C. T., Tripet, B., and Hodges, R. S. (2003) *J Chromatogr A* 1009, 45-59
43. Mant, C. T., and Hodges, R. S. (eds) (1991) *HPLC of peptides and proteins: separation, analysis and conformation*, CRC Press, Boca Raton, Fla.
44. Shai, Y. (1999) *Biochim Biophys Acta* 1462, 55-70
45. Ehrenstein, G., and Lecar, H. (1977) *Q Rev Biophys* 10, 1-34
46. Pouny, Y., Rapaport, D., Mor, A., Nicolas, P., and Shai, Y. (1992) *Biochemistry* 31, 12416-12423
47. Salgado, J., Grage, S. L., Kondejewski, L. H., Hodges, R. S., McElhaney, R. N., and Ulrich, A. S. (2001) *J Biomol NMR* 21, 191-208
48. Liu, F., Lewis, R. N., Hodges, R. S., and McElhaney, R. N. (2004) *Biophysical Journal*, in press
49. Liu, F., Lewis, R. N., Hodges, R. S., and McElhaney, R. N. (2004) *Biochemistry* 43, 3679-368
50. Liu, F., Lewis, R. N., Hodges, R. S., and McElhaney, R. N. (2002) *Biochemistry* 41, 9197-9207

51. Daum, G. (1985) *Biochim Biophys Acta* 822, 1-42
52. Devaux, P. F., and Seigneuret, M. (1985) *Biochim Biophys Acta* 822, 63-125
53. Chen, Y., Mant, C. T., Farmer, S. W., Hancock, R. E., Vasil, M. L. and Hodges, R. S. (2005) Rational design of alpha-helical antimicrobial peptides with enhanced activities and specificity/therapeutic index. *J Biol Chem* 280: 12316-12329
54. Kovacs, J. M., Mant, C. T. and Hodges, R. S. (2006) Determination of intrinsic hydrophilicity/hydrophobicity of amino acid side-chains in peptides in the absence of nearest-neighbor or conformational effects. *Biopolymers (Peptide science)* in press
55. Dolan, J. W. (2002) Temperature selectivity in reversed-phase high performance liquid chromatography. *J Chromatogr A* 965: 195-205
56. Powers, J. P., Rozek, A. and Hancock, R. E. (2004) Structure-activity relationships for the beta-hairpin cationic antimicrobial peptide polyphemusin i. *Biochim Biophys Acta* 1698: 239-250
57. Wade, D., Boman, A., Wahlin, B., Drain, C. M., Andreu, D., Boman, H. G. and Merrifield, R. B. (1990) All-d amino acid-containing channel-forming antibiotic peptides. *Proc Natl Acad Sci USA* 87: 4761-4765
58. Hoiby, N. and Koch, C. (1990) Cystic fibrosis. 1. *Pseudomonas aeruginosa* infection in cystic fibrosis and its management. *Thorax* 45: 881-884
59. Elkin, S, and Geddes, D. (2003) Pseudomonal infection in cystic fibrosis: The battle continues. *Expert Rev Anti Infect Ther* 1: 609-618
60. Pierce, G. E. (2005) *Pseudomonas aeruginosa, candida albicans*, and device-related nosocomial infections: Implications, trends, and potential approaches for control. *J Ind Microbiol Biotechnol* 32: 309-318
61. Obritsch, M.D., Fish, D. N., Maclaren, R. and Jung, R. (2005) Nosocomial infections due to multidrug-resistant *pseudomonas aeruginosa*: Epidemiology and treatment options. *Pharmacotherapy* 25: 1353-1364
62. Al-Bakri, A. G., Gilbert, P. and Allison, D. G. (2005) Influence of gentamicin and tobramycin on binary biofilm formation by co-cultures of *Burkholderia cepacia* and *Pseudomonas aeruginosa*. *J Basic Microbiol* 45: 392-396
63. Bodmann, K. F. (2005) Current guidelines for the treatment of severe pneumonia and sepsis. *Chemotherapy* 51: 227-233
64. Avrahami, D. and Shai, Y. (2002) Conjugation of a magainin analogue with lipophilic acids controls hydrophobicity, solution assembly, and cell selectivity. *Biochemistry* 41: 2254-2263
65. Wieprecht, T., Dathe, M., Beyermann, M., Krause, E., Maloy, W. L., MacDonald, D. L. and Bienert, M. (1997) Peptide hydrophobicity controls the activity and selectivity of magainin 2 amide in interaction with membranes. *Biochemistry* 36: 6124-6132
66. Kustanovich, I., Shalev, D. E., Mikhlin, M., Gaidukov, L. and Mor, A. (2002) Structural requirements for potent versus selective cytotoxicity for antimicrobial dermaseptin s4 derivatives. *J Biol Chem* 277: 16941-16951
67. Tachi, T., Epand, R. F., Epand, R. M. and Matsuzaki, K. (2002) Position-dependent hydrophobicity of the antimicrobial magainin peptide affects the mode of peptide-lipid interactions and selective toxicity. *Biochemistry* 41: 10723-10731
68. Lugtenberg, B. and Van Alphen, L. (1983) Molecular architecture and functioning of the outer membrane of *escherichia coli* and other gram-negative bacteria. *Biochim Biophys Acta* 737: 51-115
69. Zilberstein, D., Schuldiner, S, and Padan, E. (1979) Proton electrochemical gradient in *Escherichia coli* cells and its relation to active transport of lactose. *Biochemistry* 18: 669-673
70. Boman, H. G. (2003) Antibacterial peptides: Basic facts and emerging concepts. *J Intern Med* 254: 197-215
71. Dathe, M., Schumann, M., Wieprecht, T., Winkler, A., Beyermann, M., Krause, E., Matsuzaki, K., Murase, O. and Bienert, M. (1996) Peptide helicity and membrane surface charge modulate the balance of electrostatic and hydrophobic interactions with lipid bilayers and biological membranes. *Biochemistry* 35: 12612-12622
72. Wieprecht, T., Dathe, M., Krause, E., Beyermann, M., Maloy, W. L., MacDonald, D. L. and Bienert, M. (1997) Modulation of membrane activity of amphipathic, antibacterial peptides by slight modifications of the hydrophobic moment. *FEBS Lett* 417: 135-140
73. Blondelle, S. E. and Houghten, R. A. (1991) Hemolytic and antimicrobial activities of the twenty-four individual omission analogues of melittin. *Biochemistry* 30: 4671-4678
74. Kiyota, T., Lee, S, and Sugihara, G. (1996) Design and synthesis of amphiphilic alpha-helical model peptides with systematically varied hydrophobic-hydrophilic balance and their interaction with lipid- and bio-membranes. *Biochemistry* 35: 13196-13204
75. Blondelle, S. E., Lohner, K. and Aguilar, M. (1999) Lipid-induced conformation and lipid-binding properties of cytolytic and antimicrobial peptides: Determination and biological specificity. *Biochim Biophys Acta* 1462: 89-108
76. Hancock, R. E. and Rozek, A. (2002) Role of membranes in the activities of antimicrobial cationic peptides. *FEMS Microbiol Lett* 206: 143-149
77. Sitaram, N. and Nagaraj, R. (1999) Interaction of antimicrobial peptides with biological and model membranes: Structural and charge requirements for activity. *Biochim Biophys Acta* 1462: 29-54
78. Shai, Y. (1999) Mechanism of the binding, insertion and destabilization of phospholipid bilayer membranes by alpha-helical antimicrobial and cell non-selective membrane-lytic peptides. *Biochim Biophys Acta* 1462: 55-70
79. Matsuzaki, K. (1999) Why and how are peptide-lipid interactions utilized for self-defense? Magainins and tachyplesins as archetypes. *Biochim Biophys Acta* 1462: 1-10
80. Chen, Y., Mehok, A. R., Mant, C. T. and Hodges, R. S. (2004) Optimum concentration of trifluoroacetic acid for reversed-phase liquid chromatography of peptides revisited. *J Chromatogr A* 1043: 9-18
81. Reddy, K. V., Yedery, R. D. and Aranha, C. (2004) Antimicrobial peptides: Premises and promises. *Int J Antimicrob Agents* 24: 536-547
82. Brogden, K. A. (2005) Antimicrobial peptides: Pore formers or metabolic inhibitors in bacteria? *Nat Rev Microbiol* 3: 238-250
83. Bland, J. M., De Lucca, A. J., Jacks, T. J. and Vigo, C. B. (2001) All-D-cecropin b: Synthesis, conformation, lipopolysaccharide binding, and antibacterial activity. *Mol Cell Biochem* 218: 105-111
84. De Lucca, A. J., Bland, J. M., Vigo, C. B., Jacks, T. J., Peter, J. and Walsh, T. J. (2000) D-cecropin b: Proteolytic resistance, lethality for pathogenic fungi and binding properties. *Med Mycol* 38: 301-308
85. Cribbs, D. H., Pike, C. J., Weinstein, S. L., Velazquez, P. and Cotman, C. W. (1997) All-D-enantiomers of beta-amyloid exhibit similar biological properties to all-L-beta-amyloids. *J Biol Chem* 272: 7431-7436

86. Hamamoto, K., Kida, Y., Zhang, Y., Shimizu, T. and Kuwano, K. (2002) Antimicrobial activity and stability to proteolysis of small linear cationic peptides with D-amino acid substitutions. *Microbiol. Immunol* 46: 741-749
87. Elmquist, A. and Langel, U. (2003) In vitro uptake and stability study of pVEC and its all-D analog. *Biol Chem* 384: 387-393
88. Hong, S. Y., Oh, J. E. and Lee, K. H. (1999) Effect of D-amino acid substitution on the stability, the secondary structure, and the activity of membrane-active peptide. *Biochem Pharmacol* 58: 1775-1780
89. Wakabayashi, H., Matsumoto, H., Hashimoto, K., Teraguchi, S., Takase, M. and Hayasawa, H. (1999) N-acylated and D enantiomer derivatives of a nonamer core peptide of lactoferricin B showing improved antimicrobial activity. *Antimicrob Agents Chemother* 43: 1267-1269
90. Guo, D., Mant, C. T., Taneja, A. K., Parker, J. M. R. and Hodges, R. S. (1986) Prediction of peptide retention times in reversed-phase high-performance liquid chromatography. I. Determination of retention coefficients of amino acid residues using model synthetic peptides. *J Chromatogr* 359: 499-518

Zhang L, Rozek A, Hancock RE. Interaction of cationic antimicrobial peptides with model membranes. *J Biol. Chem.* 2001 Sep. 21; 276(38):35714-22.

U.S. Patent Documents: U.S. Pat. Nos. 6,906,035, 6,818,407, 6,747,007, 6,465,429, 6,358,921, 6,337,317, 6,297,215, 6,288,212, 6,191,254, 6,172,185, 6,057,291, 6,040,435, 5,877,274, 5,789,377, 5,707,855, 5,688,767, 5,593,866, 20030228324, 20030021795, U.S. Pat. No. 6,872,806.

The Sequence Listing is incorporated by reference herein.

What is claimed is:

1. A method of increasing antimicrobial activity or decreasing hemolytic activity of an antimicrobial peptide comprising
producing a modified antimicrobial peptide by replacing at least one hydrophobic amino acid residue in a hydrophobic face of the antimicrobial peptide of SEQ ID NO:1 with at least one hydrophilic amino acid residue, wherein the modified antimicrobial peptide produced is helical in a hydrophobic environment, and disordered in aqueous media.

2. The method of claim 1, wherein the at least one hydrophilic amino acid residue is an amino acid residue having a negatively-charged side chain.

3. The method of claim 1, wherein the at least one hydrophilic amino acid residue is an amino acid residue having a positively-charged side chain.

4. The method of claim 3, wherein the at least one hydrophilic amino acid residue is a lysine amino acid residue.

5. The method of claim 1, wherein the at least one hydrophilic amino acid residue is selected from the group consisting of D-lysine and D-alanine, and wherein all other amino acids residues in the modified antimicrobial peptide are in the L-enantiomeric form.

6. The method of claim 1, wherein the modified antimicrobial peptide produced is selected from the group consisting of SEQ ID NO:24 and SEQ ID NO:25.

7. The method of claim 1, wherein the modified antimicrobial peptide produced is selected from the group consisting of SEQ ID NO:6 and SEQ ID NO:9.

8. The method of claim 1, wherein the modified antimicrobial peptide produced is selected from the group consisting of SEQ ID NO:10 and SEQ ID NO:11.

9. The method of claim 1, wherein the producing step further comprises truncating one residue from an end of the antimicrobial peptide of SEQ ID NO:1.

10. The method of claim 1, wherein the producing step further comprises truncating two residues from an end of the antimicrobial peptide of SEQ ID NO:1.

* * * * *

```
                        SEQUENCE LISTING

<160> NUMBER OF SEQ ID NOS: 52

<210> SEQ ID NO 1
<211> LENGTH: 26
<212> TYPE: PRT
<213> ORGANISM: Artificial sequence
<220> FEATURE:
<223> OTHER INFORMATION: Synthetic peptide

<400> SEQUENCE: 1

Lys Trp Lys Ser Phe Leu Lys Thr Phe Lys Ser Ala Val Lys Thr Val
1               5                   10                  15

Leu His Thr Ala Leu Lys Ala Ile Ser Ser
            20                  25

<210> SEQ ID NO 2
<211> LENGTH: 26
<212> TYPE: PRT
<213> ORGANISM: Artificial sequence
<220> FEATURE:
<223> OTHER INFORMATION: Synthetic peptide

<400> SEQUENCE: 2

Lys Trp Lys Ser Phe Leu Lys Thr Phe Lys Ser Ala Leu Lys Thr Val
1               5                   10                  15

Leu His Thr Ala Leu Lys Ala Ile Ser Ser
            20                  25

<210> SEQ ID NO 3
<211> LENGTH: 26
<212> TYPE: PRT
<213> ORGANISM: Artificial sequence
<220> FEATURE:
<223> OTHER INFORMATION: Synthetic peptide

<400> SEQUENCE: 3

Lys Trp Lys Ser Phe Leu Lys Thr Phe Lys Ser Ala Val Lys Thr Val
1               5                   10                  15

Leu His Thr Ala Leu Lys Ala Ile Ser Ser
            20                  25

<210> SEQ ID NO 4
<211> LENGTH: 26
<212> TYPE: PRT
<213> ORGANISM: Artificial sequence
<220> FEATURE:
<223> OTHER INFORMATION: Synthetic peptide
```

```
<400> SEQUENCE: 4

Lys Trp Lys Ser Phe Leu Lys Thr Phe Lys Ser Ala Ala Lys Thr Val
1               5                   10                  15

Leu His Thr Ala Leu Lys Ala Ile Ser Ser
            20                  25

<210> SEQ ID NO 5
<211> LENGTH: 26
<212> TYPE: PRT
<213> ORGANISM: Artificial sequence
<220> FEATURE:
<223> OTHER INFORMATION: Synthetic peptide

<400> SEQUENCE: 5

Lys Trp Lys Ser Phe Leu Lys Thr Phe Lys Ser Ala Ser Lys Thr Val
1               5                   10                  15

Leu His Thr Ala Leu Lys Ala Ile Ser Ser
            20                  25

<210> SEQ ID NO 6
<211> LENGTH: 26
<212> TYPE: PRT
<213> ORGANISM: Artificial sequence
<220> FEATURE:
<223> OTHER INFORMATION: Synthetic peptide

<400> SEQUENCE: 6

Lys Trp Lys Ser Phe Leu Lys Thr Phe Lys Ser Ala Lys Lys Thr Val
1               5                   10                  15

Leu His Thr Ala Leu Lys Ala Ile Ser Ser
            20                  25

<210> SEQ ID NO 7
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (13)..(13)
<223> OTHER INFORMATION: L at position 13 is D-Leu.

<400> SEQUENCE: 7

Lys Trp Lys Ser Phe Leu Lys Thr Phe Lys Ser Ala Leu Lys Thr Val
1               5                   10                  15

Leu His Thr Ala Leu Lys Ala Ile Ser Ser
            20                  25

<210> SEQ ID NO 8
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (13)..(13)
<223> OTHER INFORMATION: V at position 13 is D-Val.

<400> SEQUENCE: 8

Lys Trp Lys Ser Phe Leu Lys Thr Phe Lys Ser Ala Val Lys Thr Val
1               5                   10                  15

Leu His Thr Ala Leu Lys Ala Ile Ser Ser
            20                  25
```

<210> SEQ ID NO 9
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (13)..(13)
<223> OTHER INFORMATION: A at position 13 is D-Ala.

<400> SEQUENCE: 9

Lys Trp Lys Ser Phe Leu Lys Thr Phe Lys Ser Ala Ala Lys Thr Val
1               5                   10                  15

Leu His Thr Ala Leu Lys Ala Ile Ser Ser
            20                  25

<210> SEQ ID NO 10
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (13)..(13)
<223> OTHER INFORMATION: S at position 13 is D-Ser.

<400> SEQUENCE: 10

Lys Trp Lys Ser Phe Leu Lys Thr Phe Lys Ser Ala Ser Lys Thr Val
1               5                   10                  15

Leu His Thr Ala Leu Lys Ala Ile Ser Ser
            20                  25

<210> SEQ ID NO 11
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (13)..(13)
<223> OTHER INFORMATION: K at position 13 is D-Lys.

<400> SEQUENCE: 11

Lys Trp Lys Ser Phe Leu Lys Thr Phe Lys Ser Ala Lys Lys Thr Val
1               5                   10                  15

Leu His Thr Ala Leu Lys Ala Ile Ser Ser
            20                  25

<210> SEQ ID NO 12
<211> LENGTH: 26
<212> TYPE: PRT
<213> ORGANISM: Artificial sequence
<220> FEATURE:
<223> OTHER INFORMATION: Synthetic peptide

<400> SEQUENCE: 12

Lys Trp Lys Ser Phe Leu Lys Thr Phe Lys Ser Ala Gly Lys Thr Val
1               5                   10                  15

Leu His Thr Ala Leu Lys Ala Ile Ser Ser
            20                  25

<210> SEQ ID NO 13

```
<211> LENGTH: 26
<212> TYPE: PRT
<213> ORGANISM: Artificial sequence
<220> FEATURE:
<223> OTHER INFORMATION: Synthetic peptide

<400> SEQUENCE: 13

Lys Trp Lys Ser Phe Leu Lys Thr Phe Lys Leu Ala Val Lys Thr Val
1               5                   10                  15

Leu His Thr Ala Leu Lys Ala Ile Ser Ser
            20                  25

<210> SEQ ID NO 14
<211> LENGTH: 26
<212> TYPE: PRT
<213> ORGANISM: Artificial sequence
<220> FEATURE:
<223> OTHER INFORMATION: Synthetic peptide

<400> SEQUENCE: 14

Lys Trp Lys Ser Phe Leu Lys Thr Phe Lys Ala Ala Val Lys Thr Val
1               5                   10                  15

Leu His Thr Ala Leu Lys Ala Ile Ser Ser
            20                  25

<210> SEQ ID NO 15
<211> LENGTH: 26
<212> TYPE: PRT
<213> ORGANISM: Artificial sequence
<220> FEATURE:
<223> OTHER INFORMATION: Synthetic peptide

<400> SEQUENCE: 15

Lys Trp Lys Ser Phe Leu Lys Thr Phe Lys Ser Ala Val Lys Thr Val
1               5                   10                  15

Leu His Thr Ala Leu Lys Ala Ile Ser Ser
            20                  25

<210> SEQ ID NO 16
<211> LENGTH: 26
<212> TYPE: PRT
<213> ORGANISM: Artificial sequence
<220> FEATURE:
<223> OTHER INFORMATION: Synthetic peptide

<400> SEQUENCE: 16

Lys Trp Lys Ser Phe Leu Lys Thr Phe Lys Val Ala Val Lys Thr Val
1               5                   10                  15

Leu His Thr Ala Leu Lys Ala Ile Ser Ser
            20                  25

<210> SEQ ID NO 17
<211> LENGTH: 26
<212> TYPE: PRT
<213> ORGANISM: Artificial sequence
<220> FEATURE:
<223> OTHER INFORMATION: Synthetic peptide

<400> SEQUENCE: 17

Lys Trp Lys Ser Phe Leu Lys Thr Phe Lys Lys Ala Val Lys Thr Val
1               5                   10                  15

Leu His Thr Ala Leu Lys Ala Ile Ser Ser
            20                  25
```

```
<210> SEQ ID NO 18
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: L at position 11 is D-Leu.

<400> SEQUENCE: 18

Lys Trp Lys Ser Phe Leu Lys Thr Phe Lys Leu Ala Val Lys Thr Val
1               5                   10                  15

Leu His Thr Ala Leu Lys Ala Ile Ser Ser
            20                  25

<210> SEQ ID NO 19
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: A at position 11 is D-Ala.

<400> SEQUENCE: 19

Lys Trp Lys Ser Phe Leu Lys Thr Phe Lys Ala Ala Val Lys Thr Val
1               5                   10                  15

Leu His Thr Ala Leu Lys Ala Ile Ser Ser
            20                  25

<210> SEQ ID NO 20
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: S at position 11 is D-Ser.

<400> SEQUENCE: 20

Lys Trp Lys Ser Phe Leu Lys Thr Phe Lys Ser Ala Val Lys Thr Val
1               5                   10                  15

Leu His Thr Ala Leu Lys Ala Ile Ser Ser
            20                  25

<210> SEQ ID NO 21
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: V at position 11 is D-Val.

<400> SEQUENCE: 21

Lys Trp Lys Ser Phe Leu Lys Thr Phe Lys Val Ala Val Lys Thr Val
1               5                   10                  15

Leu His Thr Ala Leu Lys Ala Ile Ser Ser
            20                  25
```

-continued

```
<210> SEQ ID NO 22
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: K at position 11 is D-Lys.

<400> SEQUENCE: 22

Lys Trp Lys Ser Phe Leu Lys Thr Phe Lys Lys Ala Val Lys Thr Val
1               5                   10                  15

Leu His Thr Ala Leu Lys Ala Ile Ser Ser
            20                  25

<210> SEQ ID NO 23
<211> LENGTH: 26
<212> TYPE: PRT
<213> ORGANISM: Artificial sequence
<220> FEATURE:
<223> OTHER INFORMATION: Synthetic peptide

<400> SEQUENCE: 23

Lys Trp Lys Ser Phe Leu Lys Thr Phe Lys Gly Ala Val Lys Thr Val
1               5                   10                  15

Leu His Thr Ala Leu Lys Ala Ile Ser Ser
            20                  25

<210> SEQ ID NO 24
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(26)
<223> OTHER INFORMATION: All amino acids are in D-conformation.

<400> SEQUENCE: 24

Lys Trp Lys Ser Phe Leu Lys Thr Phe Lys Ser Ala Lys Lys Thr Val
1               5                   10                  15

Leu His Thr Ala Leu Lys Ala Ile Ser Ser
            20                  25

<210> SEQ ID NO 25
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(26)
<223> OTHER INFORMATION: Each amino acid except A at position 13 is in
      D-conformation.

<400> SEQUENCE: 25

Lys Trp Lys Ser Phe Leu Lys Thr Phe Lys Ser Ala Ala Lys Thr Val
1               5                   10                  15

Leu His Thr Ala Leu Lys Ala Ile Ser Ser
            20                  25

<210> SEQ ID NO 26
```

```
<211> LENGTH: 18
<212> TYPE: PRT
<213> ORGANISM: Artificial sequence
<220> FEATURE:
<223> OTHER INFORMATION: Synthetic peptide

<400> SEQUENCE: 26

Glu Leu Glu Lys Gly Gly Leu Glu Gly Glu Lys Gly Gly Lys Glu Leu
1               5                   10                  15

Glu Lys

<210> SEQ ID NO 27
<211> LENGTH: 26
<212> TYPE: PRT
<213> ORGANISM: Artificial sequence
<220> FEATURE:
<223> OTHER INFORMATION: Synthetic peptide

<400> SEQUENCE: 27

Lys Trp Lys Ser Phe Leu Lys Thr Lys Lys Ser Ala Val Lys Thr Val
1               5                   10                  15

Leu His Thr Ala Leu Lys Ala Ile Ser Ser
            20                  25

<210> SEQ ID NO 28
<211> LENGTH: 26
<212> TYPE: PRT
<213> ORGANISM: Artificial sequence
<220> FEATURE:
<223> OTHER INFORMATION: Synthetic peptide

<400> SEQUENCE: 28

Lys Trp Lys Ser Lys Leu Lys Thr Phe Lys Ser Ala Val Lys Thr Val
1               5                   10                  15

Leu His Thr Ala Leu Lys Ala Ile Ser Ser
            20                  25

<210> SEQ ID NO 29
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: A at position 9 is D-Ala.

<400> SEQUENCE: 29

Lys Trp Lys Ser Phe Leu Lys Thr Ala Lys Ser Ala Val Lys Thr Val
1               5                   10                  15

Leu His Thr Ala Leu Lys Ala Ile Ser Ser
            20                  25

<210> SEQ ID NO 30
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: A at position 5 is D-Ala.

<400> SEQUENCE: 30
```

```
Lys Trp Lys Ser Ala Leu Lys Thr Phe Lys Ser Ala Val Lys Thr Val
1               5                   10                  15

Leu His Thr Ala Leu Lys Ala Ile Ser Ser
            20                  25
```

<210> SEQ ID NO 31
<211> LENGTH: 26
<212> TYPE: PRT
<213> ORGANISM: Artificial sequence
<220> FEATURE:
<223> OTHER INFORMATION: Synthetic peptide

<400> SEQUENCE: 31

```
Lys Trp Lys Ser Phe Leu Lys Thr Phe Lys Ser Ala Arg Lys Thr Val
1               5                   10                  15

Leu His Thr Ala Leu Lys Ala Ile Ser Ser
            20                  25
```

<210> SEQ ID NO 32
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(26)
<223> OTHER INFORMATION: A at positions 6 and 21 is D-Ala.

<400> SEQUENCE: 32

```
Lys Trp Lys Ser Phe Ala Lys Thr Phe Lys Ser Ala Val Lys Thr Val
1               5                   10                  15

Leu His Thr Ala Ala Lys Ala Ile Ser Ser
            20                  25
```

<210> SEQ ID NO 33
<211> LENGTH: 26
<212> TYPE: PRT
<213> ORGANISM: Artificial sequence
<220> FEATURE:
<223> OTHER INFORMATION: Synthetic peptide

<400> SEQUENCE: 33

```
Lys Trp Lys Ser Phe Lys Lys Thr Phe Lys Ser Ala Val Lys Thr Val
1               5                   10                  15

Leu His Thr Ala Lys Lys Ala Ile Ser Ser
            20                  25
```

<210> SEQ ID NO 34
<211> LENGTH: 25
<212> TYPE: PRT
<213> ORGANISM: Artificial sequence
<220> FEATURE:
<223> OTHER INFORMATION: Synthetic peptide

<400> SEQUENCE: 34

```
Trp Lys Ser Phe Leu Lys Thr Phe Lys Ser Ala Lys Lys Thr Val Leu
1               5                   10                  15

His Thr Ala Leu Lys Ala Ile Ser Ser
            20                  25
```

<210> SEQ ID NO 35
<211> LENGTH: 24
<212> TYPE: PRT
<213> ORGANISM: Artificial sequence

```
<220> FEATURE:
<223> OTHER INFORMATION: Synthetic peptide

<400> SEQUENCE: 35

Lys Ser Phe Leu Lys Thr Phe Lys Ser Ala Lys Lys Thr Val Leu His
1               5                   10                  15

Thr Ala Leu Lys Ala Ile Ser Ser
            20

<210> SEQ ID NO 36
<211> LENGTH: 24
<212> TYPE: PRT
<213> ORGANISM: Artificial sequence
<220> FEATURE:
<223> OTHER INFORMATION: Synthetic peptide

<400> SEQUENCE: 36

Lys Trp Lys Ser Phe Leu Lys Thr Phe Lys Ser Ala Lys Lys Thr Val
1               5                   10                  15

Leu His Thr Ala Leu Lys Ala Ile
            20

<210> SEQ ID NO 37
<211> LENGTH: 23
<212> TYPE: PRT
<213> ORGANISM: Artificial sequence
<220> FEATURE:
<223> OTHER INFORMATION: Synthetic peptide

<400> SEQUENCE: 37

Lys Trp Lys Ser Phe Leu Lys Thr Phe Lys Ser Ala Lys Lys Thr Val
1               5                   10                  15

Leu His Thr Ala Leu Lys Ala
            20

<210> SEQ ID NO 38
<211> LENGTH: 26
<212> TYPE: PRT
<213> ORGANISM: Artificial sequence
<220> FEATURE:
<223> OTHER INFORMATION: Synthetic peptide

<400> SEQUENCE: 38

Lys Ile Lys Ser Ala Leu Lys Thr Leu Lys Ser Phe Lys Lys Thr Ala
1               5                   10                  15

Ala His Thr Leu Phe Lys Val Trp Ser Ser
            20                  25

<210> SEQ ID NO 39
<211> LENGTH: 26
<212> TYPE: PRT
<213> ORGANISM: Artificial sequence
<220> FEATURE:
<223> OTHER INFORMATION: Synthetic peptide

<400> SEQUENCE: 39

Ser Trp Ser Lys Phe Leu Lys Lys Phe Thr Lys Ala Lys Ser His Val
1               5                   10                  15

Leu Thr Thr Ala Leu Ser Ala Ile Lys Lys
            20                  25

<210> SEQ ID NO 40
<211> LENGTH: 26
<212> TYPE: PRT
```

```
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(13)
<223> OTHER INFORMATION: X at positions 11 and 13 is Gly, L- or D-Leu,
      L- or D-Val, L- or D-Ser, L- or D-Ala, L- or D-Lys.

<400> SEQUENCE: 40

Lys Trp Lys Ser Phe Leu Lys Thr Phe Lys Xaa Ala Xaa Lys Thr Val
1               5                   10                  15

Leu His Thr Ala Leu Lys Ala Ile Ser Ser
            20                  25

<210> SEQ ID NO 41
<211> LENGTH: 26
<212> TYPE: PRT
<213> ORGANISM: Artificial sequence
<220> FEATURE:
<223> OTHER INFORMATION: Synthetic peptide

<400> SEQUENCE: 41

Lys His Ala Val Ile Lys Trp Ser Ile Lys Ser Ser Val Lys Phe Lys
1               5                   10                  15

Ile Ser Thr Ala Phe Lys Ala Thr Thr Ile
            20                  25

<210> SEQ ID NO 42
<211> LENGTH: 26
<212> TYPE: PRT
<213> ORGANISM: Artificial sequence
<220> FEATURE:
<223> OTHER INFORMATION: Synthetic peptide

<400> SEQUENCE: 42

His Trp Ser Lys Leu Leu Lys Ser Phe Thr Lys Ala Leu Lys Lys Phe
1               5                   10                  15

Ala Lys Ala Ile Thr Ser Val Val Ser Thr
            20                  25

<210> SEQ ID NO 43
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: X at position 11 is any amino acid in L- or
      D-conformation.

<400> SEQUENCE: 43

Lys Trp Lys Ser Phe Leu Lys Thr Phe Lys Xaa Ala Val Lys Thr Val
1               5                   10                  15

Leu His Thr Ala Leu Lys Ala Ile Ser Ser
            20                  25

<210> SEQ ID NO 44
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
```

```
<222> LOCATION: (13)..(13)
<223> OTHER INFORMATION: X at position 13 is any amino acid in L- or
      D-conformation.

<400> SEQUENCE: 44

Lys Trp Lys Ser Phe Leu Lys Thr Phe Lys Ser Ala Xaa Lys Thr Val
1               5                   10                  15

Leu His Thr Ala Leu Lys Ala Ile Ser Ser
            20                  25

<210> SEQ ID NO 45
<211> LENGTH: 26
<212> TYPE: PRT
<213> ORGANISM: Artificial sequence
<220> FEATURE:
<223> OTHER INFORMATION: Synthetic peptide

<400> SEQUENCE: 45

Lys Trp Lys Ser Phe Leu Lys Thr Phe Lys Ser Ala Lys Lys Thr Val
1               5                   10                  15

Leu His Thr Ala Leu Lys Leu Ile Ser Ser
            20                  25

<210> SEQ ID NO 46
<211> LENGTH: 26
<212> TYPE: PRT
<213> ORGANISM: Artificial sequence
<220> FEATURE:
<223> OTHER INFORMATION: Synthetic peptide

<400> SEQUENCE: 46

Lys Trp Lys Ser Phe Leu Lys Thr Phe Lys Ser Leu Lys Lys Thr Val
1               5                   10                  15

Leu His Thr Ala Leu Lys Ala Ile Ser Ser
            20                  25

<210> SEQ ID NO 47
<211> LENGTH: 26
<212> TYPE: PRT
<213> ORGANISM: Artificial sequence
<220> FEATURE:
<223> OTHER INFORMATION: Synthetic peptide

<400> SEQUENCE: 47

Lys Trp Lys Ser Phe Leu Lys Thr Phe Lys Ser Ala Lys Lys Thr Val
1               5                   10                  15

Leu His Thr Leu Leu Lys Ala Ile Ser Ser
            20                  25

<210> SEQ ID NO 48
<211> LENGTH: 26
<212> TYPE: PRT
<213> ORGANISM: Artificial sequence
<220> FEATURE:
<223> OTHER INFORMATION: Synthetic peptide

<400> SEQUENCE: 48

Lys Trp Lys Ser Phe Leu Lys Thr Phe Lys Ser Leu Lys Lys Thr Val
1               5                   10                  15

Leu His Thr Ala Leu Lys Leu Ile Ser Ser
            20                  25

<210> SEQ ID NO 49
<211> LENGTH: 26
```

```
<212> TYPE: PRT
<213> ORGANISM: Artificial sequence
<220> FEATURE:
<223> OTHER INFORMATION: Synthetic peptide

<400> SEQUENCE: 49

Lys Trp Lys Ser Phe Leu Lys Thr Phe Lys Ser Leu Lys Lys Thr Val
1               5                   10                  15

Leu His Thr Leu Leu Lys Ala Ile Ser Ser
            20                  25

<210> SEQ ID NO 50
<211> LENGTH: 26
<212> TYPE: PRT
<213> ORGANISM: Artificial sequence
<220> FEATURE:
<223> OTHER INFORMATION: Synthetic peptide

<400> SEQUENCE: 50

Lys Trp Lys Ser Phe Leu Lys Thr Phe Lys Ser Leu Lys Lys Thr Val
1               5                   10                  15

Leu His Thr Leu Leu Lys Leu Ile Ser Ser
            20                  25

<210> SEQ ID NO 51
<211> LENGTH: 22
<212> TYPE: PRT
<213> ORGANISM: Artificial sequence
<220> FEATURE:
<223> OTHER INFORMATION: Synthetic peptide

<400> SEQUENCE: 51

Lys Ser Phe Leu Lys Thr Phe Lys Ser Ala Lys Leu Lys Thr Val Leu
1               5                   10                  15

His Thr Ala Leu Lys Ala
            20

<210> SEQ ID NO 52
<211> LENGTH: 22
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: K at position 11 is D-lysine.

<400> SEQUENCE: 52

Lys Ser Phe Leu Lys Thr Phe Lys Ser Ala Lys Leu Lys Thr Val Leu
1               5                   10                  15

His Thr Ala Leu Lys Ala
            20
```